United States Patent [19]

Springer et al.

[11] Patent Number: 5,391,817
[45] Date of Patent: Feb. 21, 1995

[54] BIARYL PHOSPHOLIPASE $A_2$ INHIBITORS

[75] Inventors: Dane Springer, Madison; Bing-Yu Luh, Killingworth, both of Conn.; Katharine M. Greene, Eatontown, N.J.; Joanne J. Bronson, Madison; Muzammil M. Mansuri, Cheshire, both of Conn.

[73] Assignee: Bristol-Myers Squibb, New York, N.Y.

[21] Appl. No.: 171,038

[22] Filed: Dec. 21, 1993

[51] Int. Cl.⁶ ............................................. C07C 59/40
[52] U.S. Cl. ........................... 562/469; 562/429; 562/435; 562/438; 562/451; 562/465; 562/473; 562/492; 560/14; 560/21; 560/37; 560/42; 560/51; 560/53; 560/59; 560/81; 560/102; 514/171
[58] Field of Search ............... 562/469, 465, 473, 492, 562/429, 435, 438, 451; 560/102, 51, 53, 59, 81; 544/171; 514/532, 533, 534, 539, 561, 564, 567, 570

[56] References Cited

U.S. PATENT DOCUMENTS

| 3,969,419 | 7/1976 | Engel | 560/102 |
| 4,257,911 | 3/1981 | Gray | 560/102 |
| 4,828,754 | 5/1989 | Takehara | 252/299.65 |
| 5,235,100 | 8/1993 | Chaudhuray et al. | 562/401 |

FOREIGN PATENT DOCUMENTS 2341505 2/1975 Germany .

OTHER PUBLICATIONS

Van Den Bosch, "Intracellular Phospholipases A", *Biochim. Biophys. Acta* 604 (1980) pp. 191–246.
Davies et al, "Prostaglandins and Inflammation", *Inflammation: Basic Principles and Clinical Correlates*, 2nd ed., Chapter 7, (1992) pp. 123–138.
Lam et al., "Leukotrienes", *Inflammation: Basic Principles and Clinical Correlates*, 2nd ed., Chapter 8, (1992) pp. 139–147.
Zimmerman et al., "Platelet–Activating Factor", *Inflammation: Basic Principles and Clinical Correlates*, 2nd ed., Chapter 9, (1992) pp. 149–176.
Vadas et al., "Biology of Disease", *Laboratory Investigation*, vol. 55, No. 4, (1986) pp. 391–404.
Stroebel et al., "Sacral Insufficiency Fractures", *Journal of Rheumatology*, 18:1, (1991), pp. 117–119.
Pruzanski et al., "Enzymatic Activity and Immunoreactivity of Extracellular Phospholipase $A_2$ in Inflammatory Snyovial Fluids", *Inflammation*, vol. 16, No. 5, (1992) pp. 451–457.
Pruzanski et al, "Hyperphospholipasemia $A_2$ in Human Intravenous Endotoxin", *Inflammation*, vol. 16, No. 5, (1992) pp. 561–570.
Gronroos et al, "Increased Concentrations of Synovial–Type Phospholipase $A_2$ in Serum and Pulmonary and Renal Complications in Acute Pancreatis", *Digestion*, 52, (1992) pp. 232–236.

*Primary Examiner*—Paul J. Killos
*Attorney, Agent, or Firm*—Sandra M. Nolan

[57] ABSTRACT

Certain novel biaryl compounds are effective phospholipase $A_2$ ($PLA_2$) inhibitors.

26 Claims, No Drawings

BIARYL PHOSPHOLIPASE A₂ INHIBITORS

BACKGROUND OF THE INVENTION

The invention deals with compounds having activity as phospholipase $A_2$ ($PLA_2$) inhibitors. $PLA_2$ is a calcium-dependent enzyme which cleaves the sn-2 acyl bond of phospholipids to yield arachidonic acid and a lysophospholipid (H. Van den Bosch et al in Biochim. Biophys. Acta 1980, 604, 191). Both products of this reaction can serve as starting points for the biosynthesis of inflammatory mediators. Once released, arachidonic acid is rapidly metabolized by enzymes such as cyclooxygenase and lipoxgenases to give prostaglandins and leukotrienes, well-known mediators of inflammation (P. Davies and D. E. MacIntyre in "Inflammation: Basic Principles and Clinical Correlates," 2nd Ed., J. I. Gallin, I. M. Goldstein, and R. Snyderman, Eds., Raven Press, Ltd.: New York, 1992; Chapter 7; B. K. Lam and K. F. Austen in "Inflammation: Basic Principles and Clinical Correlates," 2nd Ed., J. I. Gallin, I. M. Goldstein, and R. Snyderman, Eds., Raven Press, Ltd.: New York, 1992; Chapter 8). Lysophospholipids can be utilized by certain cell types to produce platelet-activating factor (PAF), another potent inflammatory mediator (G. A. Zimmerman, S. M. Prescott, and T. M. Mcintyre in "Inflammation: Basic Principles and Clinical Correlates," 2nd Ed., J. I. Gallin, I. M. Goldstein, and R. Snyderman, Eds., Raven Press, Ltd.: New York, 1992; Chapter 9). The role of $PLA_2$ in inflammatory diseases has been described (P. Vadas and W. Pruzanski in Laboratory Investigation, 1986, 55, 391–404; R. Stroetel W. Ginsburg and R. McLeod, in Journal of Rheumatology, 1991, 18, 117–119; W. Pruzanski, K. Scott, G. Smith, I. Rajkovic, E. Stefanski, and P. Vadas in Inflammation, 1992, 16, 451–457; W. Pruzanski, D. W. Wilmore, A. Suffredini, G. D. Martich, A. G. D. Hoffman, J. L. Browning, E. Stefanski, B. Sternby, and P. Vadas in Inflammation, 1992, 16, 561–570; J. M. Gronroos and T. J. Nevalainen in Digestion, 1992, 52, 232–236). Since $PLA_2$ is the critical enzyme in the pathway leading to release of prostaglandins, and leukotrienes and PAF, inhibition of this enzyme is a rational approach to prevention, elimination, or amelioration of inflammation.

SUMMARY OF THE INVENTION

Applicants have discovered novel compounds of Formulas I and II:

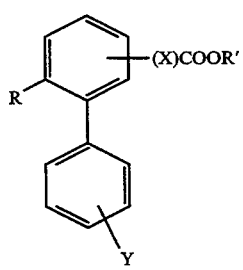

(I)

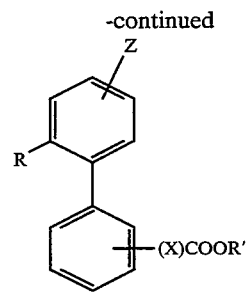

(II)

wherein:
Y=COOH, $CH_2CO_2H$, H, F, Cl, Br, I, COOR′, $CH_2CO_2R′$, $CONH_2$, COR″, CHO, $CH_2OH$, $CH_2OR″$, OH, OR″, $CF_3$, $C_{1-6}$ alkyl, $C_{1-6}$ alkenyl, $C_{1-6}$ haloalkyl, $NO_2$, P(O)(OH)$_2$, $SO_2H$, or $SO_3H$;
Z=H, F, Cl, Br, I, $CONH_2$, COR″, CHO, $CH_2OH$, $CH_2OR″$, OH, OR″, $CF_3$, $C_{1-6}$ alkyl, $C_{1-6}$ alkenyl, $C_{1-6}$ haloalkyl, $NO_2$, P(O)(OH)$_2$, $SO_2H$, or $SO_3H$;
X=$(CH_2)_n$, n=0, 1, or 2; or a cis or trans CH=CH;
R=substituted or unsubstituted alkyl, aryl, arylalkyl, alkyloxy, arylalkyloxy, alkenyl, or arylalkenyl groups with the proviso that R must have 8 or more carbons;
R′=H, $C_{1-6}$ alkyl, $C(R^1)_2OC(O)R^2$, $CH_2CH_2NR^3R^4$, $CH_2CH_2CH_2NR^3R^4$, or other groups yielding physiologically hydrolyzable esters;
R″=$C_{1-6}$ alkyl;
$R^1$=H, $CH_3$, $C_2H_5$, $CH_2CH_2CH_3$;
$R^2$=$C_{6-12}$ aryl, $C_{1-7}$ linear, branched or cyclic alkyl, or $C_{1-7}$ linear branched or cyclic alkoxy;
$R^3$=$R^4$, or, it may be linked with $R^4$, to form a $C_3-C_6$ cycloalkyl or a —$CH_2CH_2OCH_2CH_2$— group; and
$R^4$=$C_{1-3}$ alkyl; or salts thereof.

These compounds, their geometric isomers and their pharmaceutical salts, exhibit $PLA_2$ inhibition with significant anti-inflammatory effects.

The novel compounds, as well as isomers and derivatives thereof, are useful in combination with pharmaceutical carriers and other excipients in formulations to be administered by, preferably, topical or oral routes.

DESCRIPTION OF THE INVENTION

The invention is concerned with novel compounds and the use of those compounds, their isomers or other pharmaceutically acceptable derivatives, e.g., salts, thereof, in processes and compositions to be used to treat inflammation. Unless otherwise indicated, all percentages recited herein are weight percents, based upon total composition weight.

The compounds of the invention generally conform to either Formulae I or II:

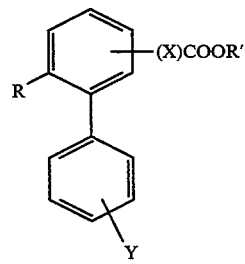

(I)

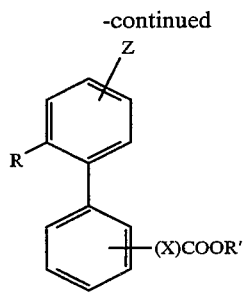

wherein:

Y=COOH, CH$_2$CO$_2$H, H, F, Cl, Br, I, COOR', CH$_2$CO$_2$R', CONH$_2$, COR", CHO, CH$_2$OH, CH$_2$OR", OH, OR", CF$_3$, C$_{1-6}$ alkyl, C$_{1-6}$ alkenyl, C$_{1-6}$ haloalkyl, NO$_2$, P(O)(OH)$_2$, SO$_2$H, or SO$_3$H;

Z=H, F, Cl, Br, I, CONH$_2$, COR", CHO, CH$_2$OH, CH$_2$OR", OH, OR", CF$_3$, C$_{1-6}$ alkyl, C$_{1-6}$ alkenyl, C$_{1-6}$ haloalkyl, NO$_2$, P(O)(OH)$_2$, SO$_2$H, or SO$_3$H;

X=(CH$_2$)$_n$, n=0, 1, or 2; or a cis or trans CH=CH;

R=substituted or unsubstituted alkyl, aryl, arylalkyl, alkyloxy, arylalkyloxy, alkenyl, or arylalkenyl groups with the proviso that R must have 8 or more carbons;

R'=H, C$_{1-6}$ alkyl, C(R$^1$)$_2$OC(O)R$^2$, CH$_2$CH$_2$NR$^3$R$^4$, CH$_2$CH$_2$CH$_2$NR$^3$R$^4$, or other groups yielding physiologically hydrolyzable esters;

R"=C$_{1-6}$ alkyl;

R$^1$=H, CH$_3$, C$_2$H$_5$, CH$_2$CH$_2$CH$_3$;

R$^2$=C$_{6-12}$ aryl, C$_{1-7}$ linear, branched or cyclic alkyl, or C$_{1-7}$ linear branched or cyclic alkoxy;

R$^3$=R$^4$, or, it may be linked with R$^4$, to form a C$_3$-C$_6$ cycloalkyl or a —CH$_2$CH$_2$OCH$_2$CH$_2$— group; and R$^4$=C$_{1-3}$ alkyl; or are salts thereof.

Y is preferably H, COOH, F, CF$_3$, COOR', or CONH$_2$. X is preferably 0 to 2 CH$_2$ groups or a CH=CH of cis or trans configuration. Z is preferably H.

In preferred embodiments, the substituent Y in structure I is in the meta position, while in structure II, Z is preferred to be in the ortho or meta position relative to the aryl substituent.

R may be optionally substituted groups of the types recited above which contain 7 or more carbons. When R is substituted, the substituents may be OH, C$_{1-12}$ alkyloxy, C$_{1-12}$ alkenyloxy, C$_{1-12}$ cycloalkyl, C$_{1-12}$ hydroxyalkyl or adamantyl. R may have from one to six substituents, with "substituents" meaning groups other than hydrogen. Preferred R groups are set out in Tables 1-6.

By "8 or more" carbons, applicants mean 8 to 30, and preferably 14 to 30, carbon atoms.

R' is preferably H.

By "halo" applicants mean F, Cl, Br, or I. "Haloalkyl" groups contain at least one halogen substituent.

R$^1$, R$^3$ and R$^4$, when independent moieties (i.e., not linked to others), may be the same or different.

Compounds of the invention generally conform to formula types IA, IB, IC, ID, IE, or II as follows:

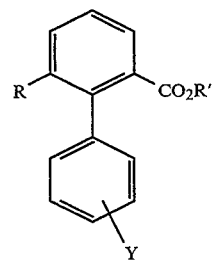

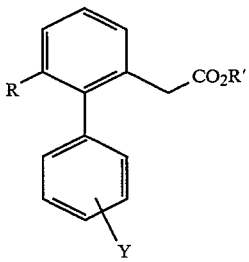

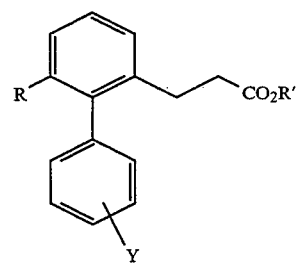

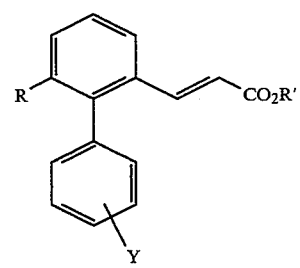

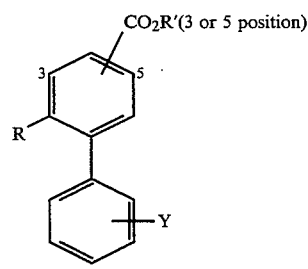

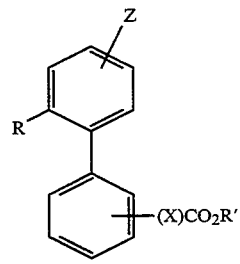

wherein the substituents are as defined above.

Compounds of structure types 11 and 14 conform to IA, 28 and 30 to IB, 37 to IC, 39 to ID, 44 and 48 to IE, 52 and 57 to II.
PREPARATION
The compounds of the invention are typically prepared using one or more of the steps shown below.
In these schemes, the following abbreviations are use: Bu=butyl, DIAD—diisopropylazodicarboxylate, Et-=ethyl, Me=methyl, Ph=phenyl, Tf=trifluoromethyl.
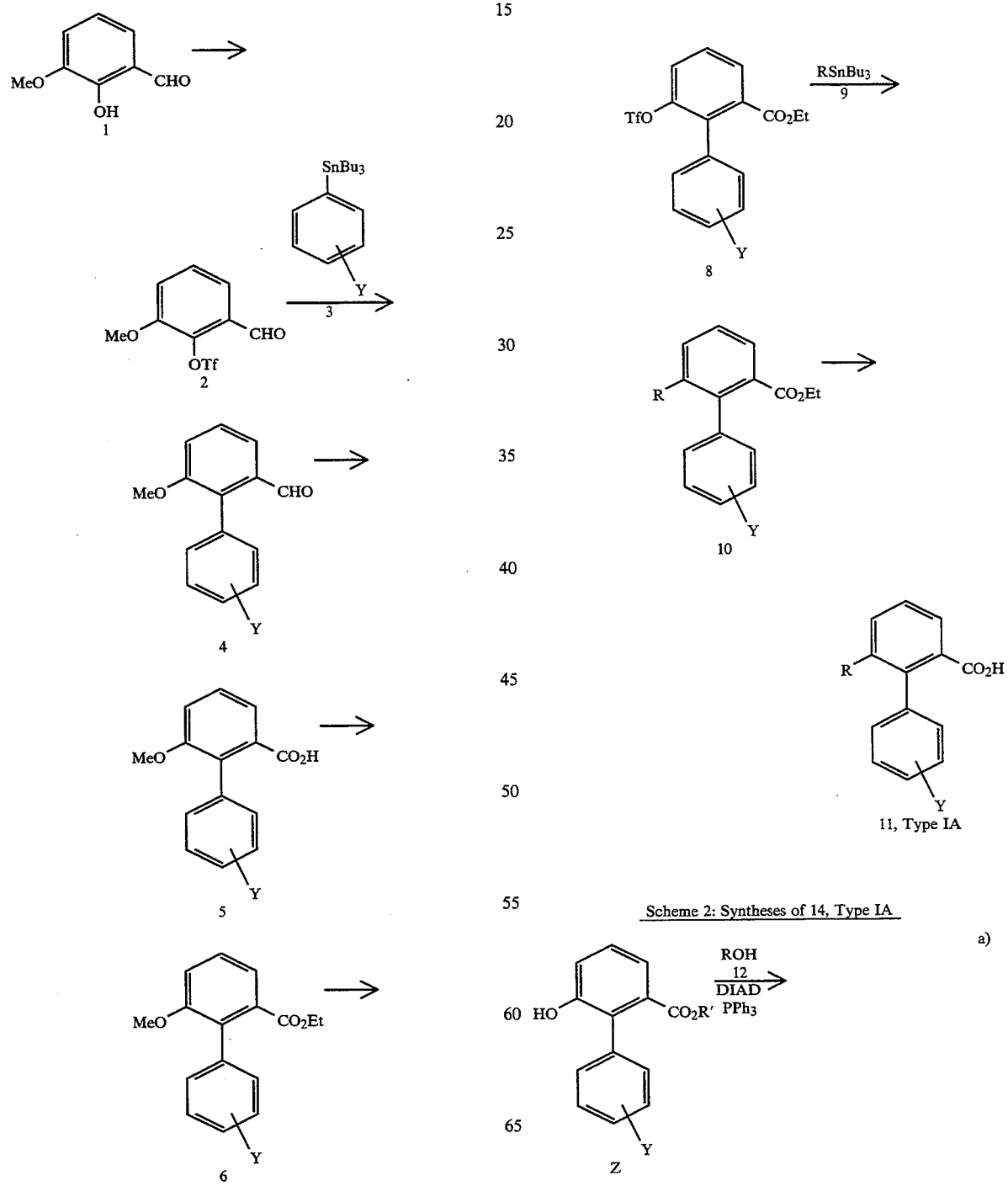

-continued
Scheme 2: Syntheses of 14, Type IA
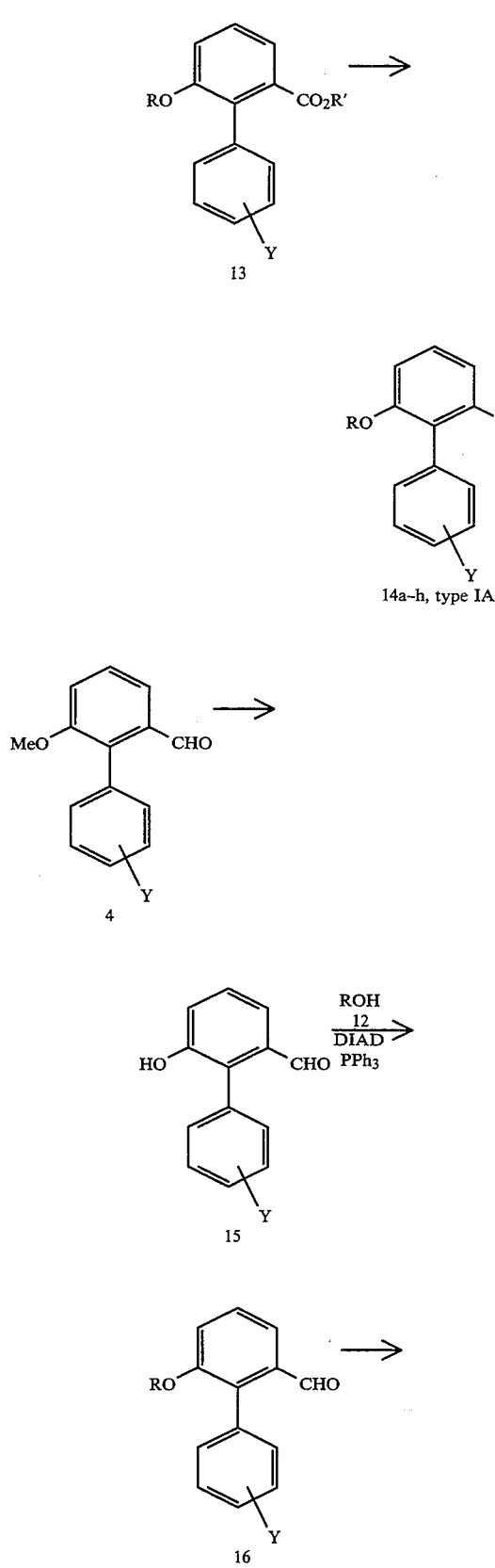
-continued
Scheme 2: Syntheses of 14, Type IA
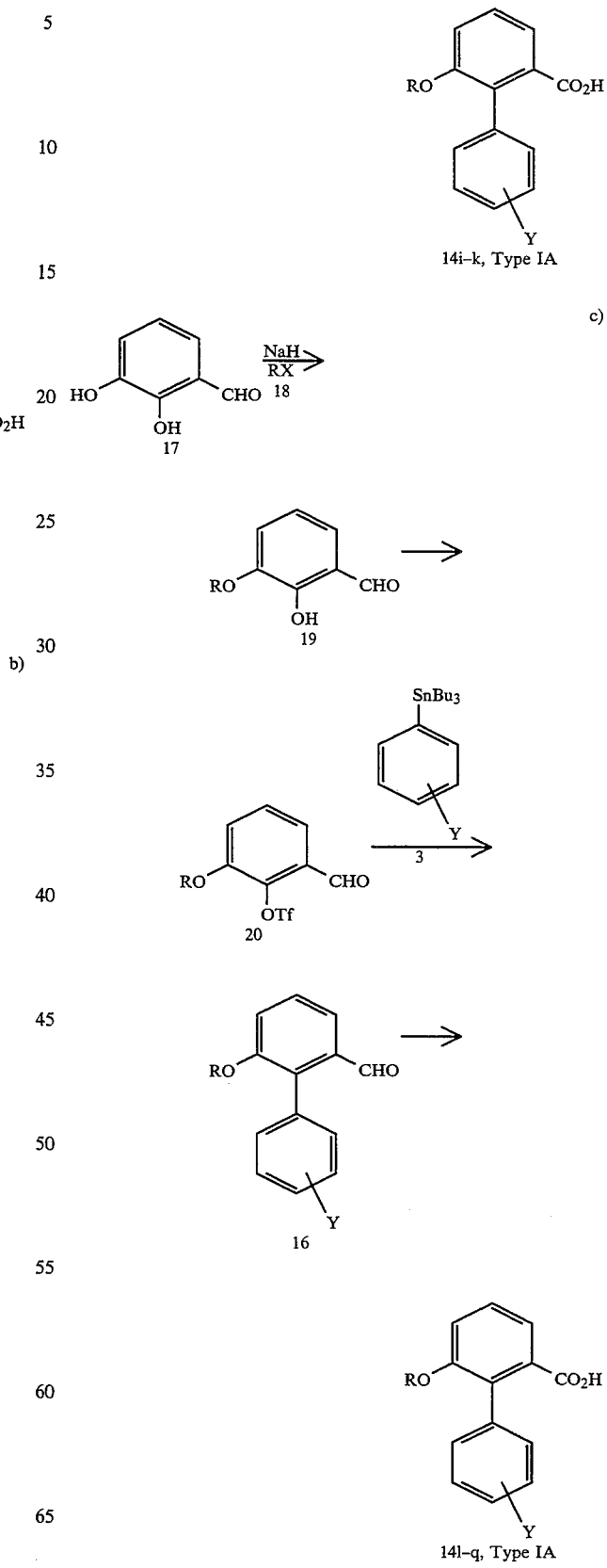

Synthesis of 28, Type IB
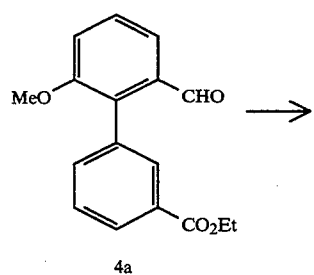
4a
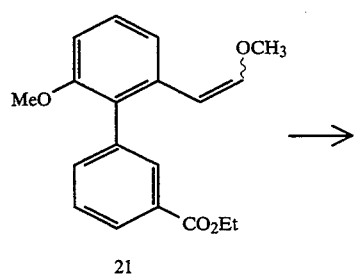
21
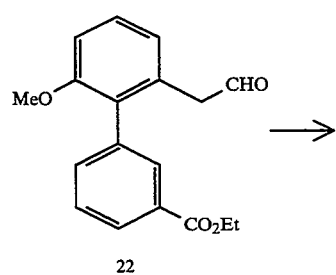
22
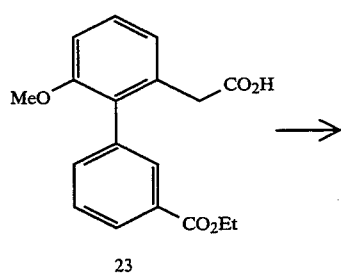
23
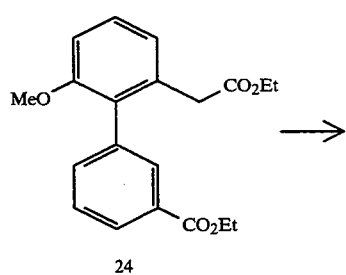
24
-continued
Synthesis of 28, Type IB
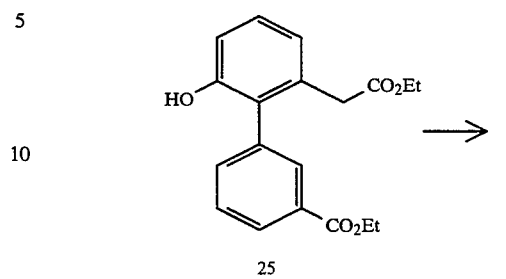
25
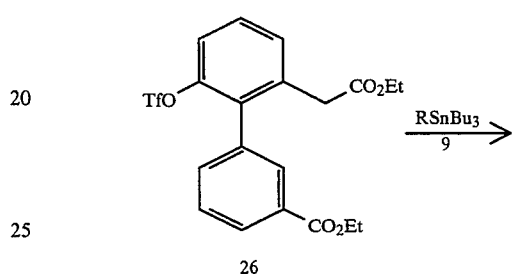
26
→ RSnBu₃ / 9
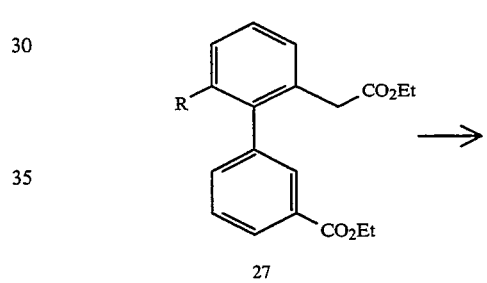
27
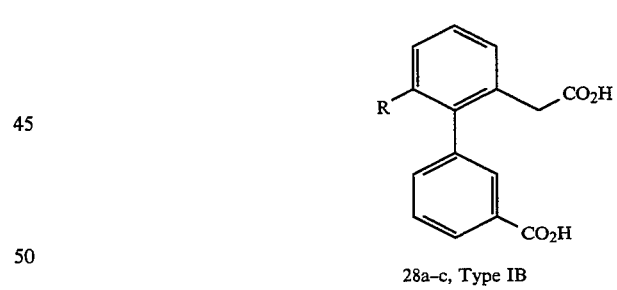
28a–c, Type IB
Scheme 4:
Syntheses of 30, Type IB
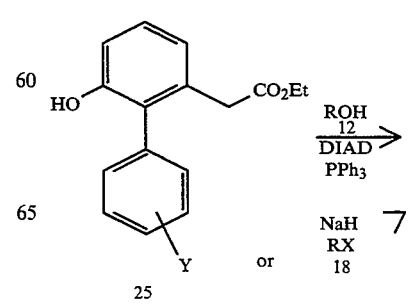
25
a) ROH 12 / DIAD / PPh₃
or NaH / RX 18

Scheme 4:
Syntheses of 30, Type IB
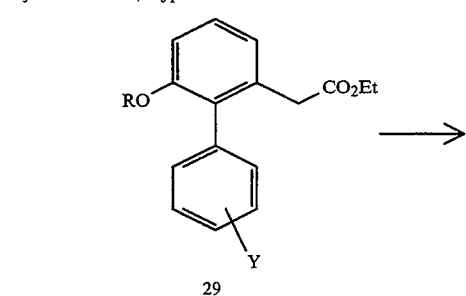
29
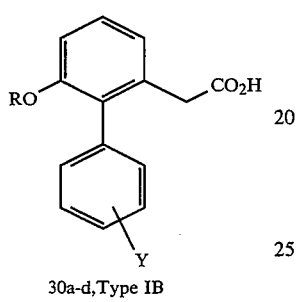
30a-d, Type IB
b)
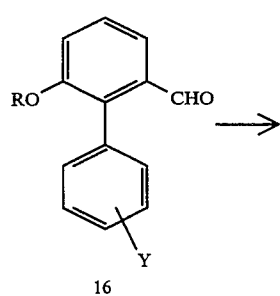
16
Scheme 4:
Syntheses of 30, Type IB
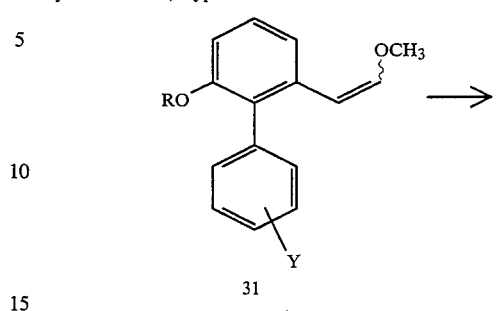
31
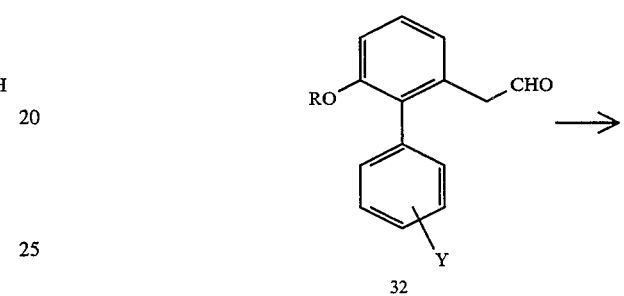
32
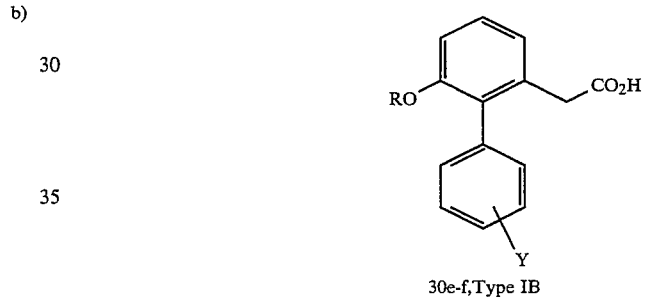
30e-f, Type IB
Scheme 5:
Synthesis of 37, Type IC, and 39, Type ID
a)
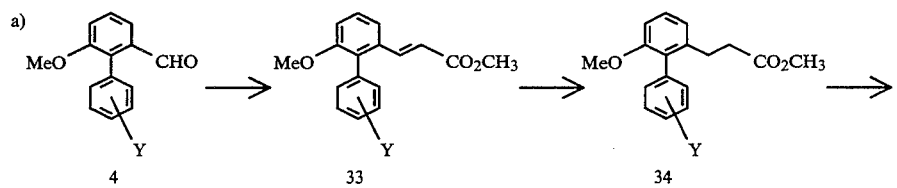
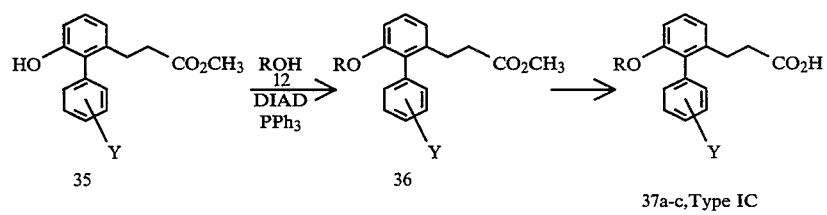

Scheme 5:
Synthesis of 37, Type IC, and 39, Type ID
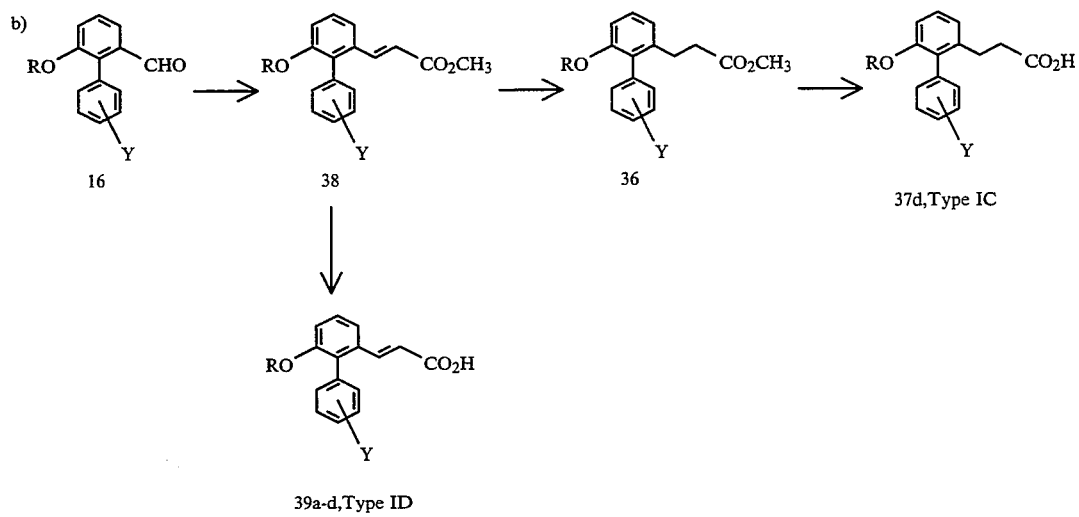
Scheme 6:
Syntheses of 44 and 48, Type IE
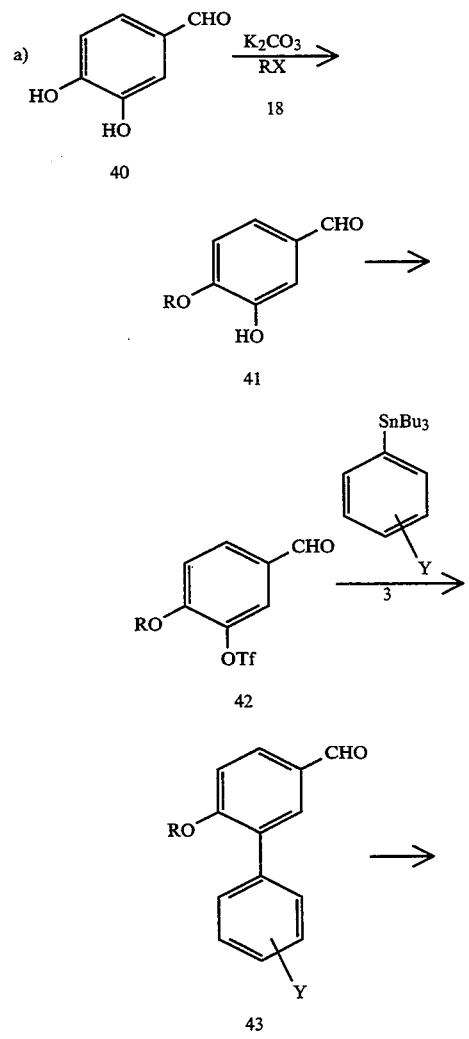
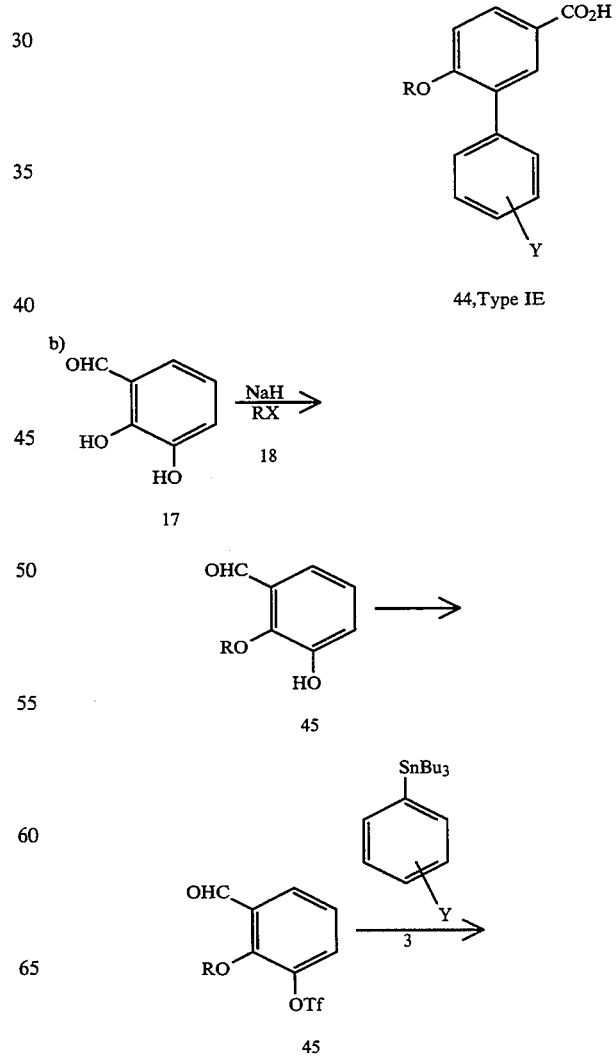

-continued
Scheme 6:
Syntheses of 44 and 48, Type IE
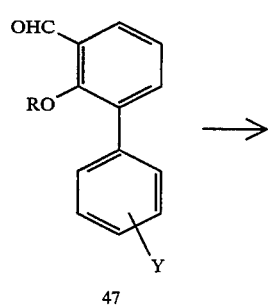
47
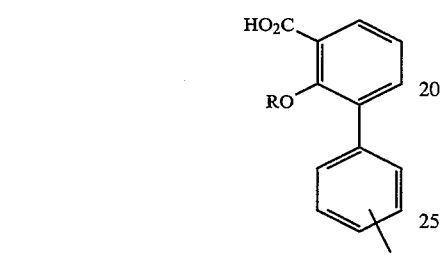
48, Type IE
Scheme 7:
Syntheses of 52, Type II
a) For meta and para acids
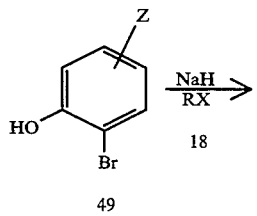
49
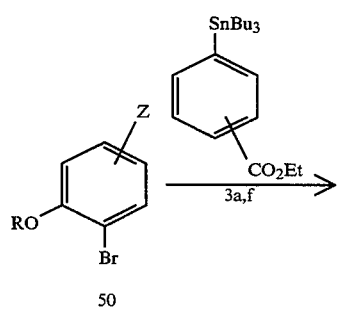
50
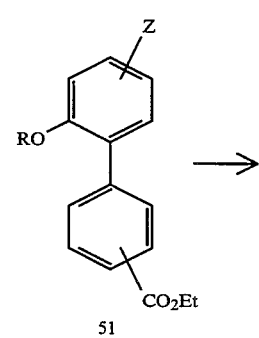
51
Scheme 7:
Syntheses of 52, Type II
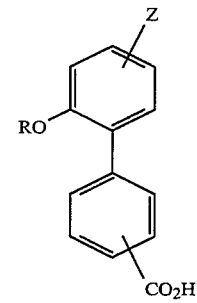
52a-b, Type II
b) For ortho acids
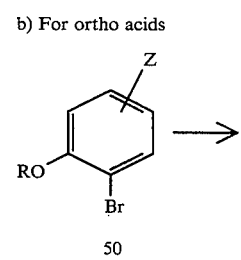
50
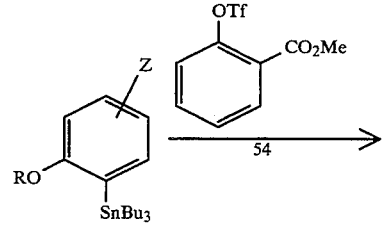
53
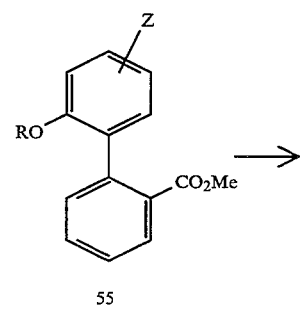
55
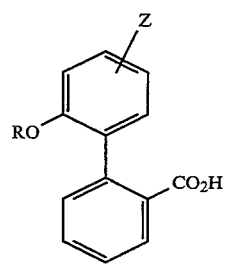
52c, Type II
Scheme 8:
Syntheses of 57, Type II

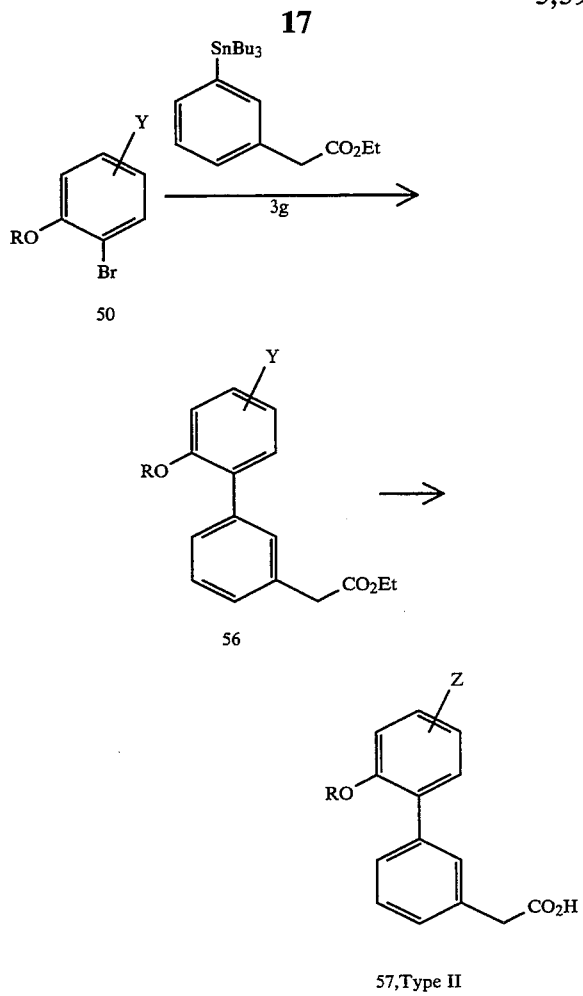

*Biophys. Acta* 575: 467–470 (1979); Franson, R. C., Patriarca, P., and Elsback, P., *J. Lipid Res.* 15: 380–388 (1974)]. The enzyme is isolated from human platelets. The substrate used consists of $^{14}$C-oleate labeled *Escherichia coli* membranes. *E. coli* cells are grown in the presence of $^{14}$C-oleic acid and then autoclaved to prepare the membranes.

Various concentrations of test compounds are preincubated with PLA$_2$ (3.6 mg/mL in a buffer consisting of 25 mM HEPES (pH 7)), 150 mM NaCl, 5.0 mM CaCl$_2$, and 10% DMSO (v/v, test compound solvent) at 37° C. for 7 minutes. The *E. coli* substrate is then added (0.1 mM phospholipid, 0,005 mCi $^{14}$C) and the reaction is then incubated at 37° C. for 30 minutes. The reaction is then terminated by the addition of 1.9 mL tetrahydrofuran (THF), and the entire solution is applied to a solid-phase extraction column (aminopropyl resin, Analytichem). The column is rinsed with an additional 1 mL of THF. The free fatty acid product of the reaction is then eluted from the column with 1 mL 2% acetic acid in THF and collected in a scintillation vial. The amount of free fatty acid product is determined by liquid scintillation counting. The amount of inhibition produced by the test compound is calculated by comparing the counts obtained in the presence of the compound to those obtained in its absence (solvent only). Background counts were determined by performing incubations in the absence of enzyme.

Percent inhibition is determined by the equation:

$$\% \text{ Inhibition} = \left(1 - \frac{(CPM \text{ with test compound}) - (\text{background})}{(CPM \text{ without test compound}) - (\text{background})}\right)$$

The biological activities of compounds of Types IAE and II are given in Tables 1-6. The compounds are effective inhibitors of PLA$_2$ in this assay.

PLA$_2$ Inhibition Assay

The method used is similar to that reported by Franson, et al. [Jesse, R. L. and Franson R. C., *Biochim.*

TABLE 1

Biological Data for Compounds of Structure 11 and 14 (Type IA):

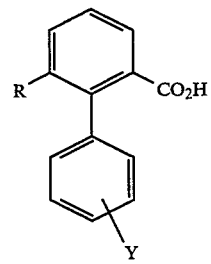

| R | Y | Structure Number | % Inhibition of PLA$_2$ at 100 μM |
|---|---|---|---|
| ![structure] | m-CO$_2$H | 11 | 80% |
| C$_{10}$H$_{21}$O-/C$_{10}$H$_{21}$O- benzyl ether | m-CO$_2$H | 14a | 99% |

TABLE 1-continued

Biological Data for Compounds of Structure 11 and 14 (Type IA):

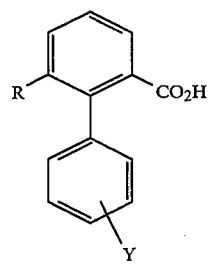

| R | Y | Structure Number | % Inhibition of PLA$_2$ at 100 μM |
|---|---|---|---|
| [3,4-bis(3-methyl-2-butenyloxy)benzyloxy] | m-CO$_2$H | 14b | 20% |
| [3,4-bis(pentyloxy)benzyloxy], C$_5$H$_{11}$O- / C$_5$H$_{11}$O- | m-CO$_2$H | 14c | 53% |
| [3,4-bis(cyclopentyloxy)benzyloxy] | m-CO$_2$H | 14d | 73% |
| [3-hydroxy-4-pentyloxybenzyloxy], HO- / C$_5$H$_{11}$O- | H | 14e | 34% |
| [3-acetoxy-4-pentyloxybenzyloxy] | H | 14f | 30% |
| [3-(1-adamantyl)-4-methoxybenzyloxy] | H | 14g | 44% |
| [3-(1-adamantyl)-4-methoxybenzyloxy] | m-CO$_2$H | 14h | 62% |
| [3,4-bis(pentyloxy)benzyloxy] | H | 14i | 99% |
| [3,4-bis(pentyloxy)benzyloxy] | m-CF$_3$ | 14j | 98% |

TABLE 1-continued
Biological Data for Compounds of Structure 11 and 14 (Type IA):
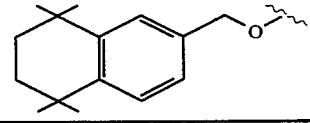
| R | Y | Structure Number | % Inhibition of PLA$_2$ at 100 μM |
|---|---|---|---|
| 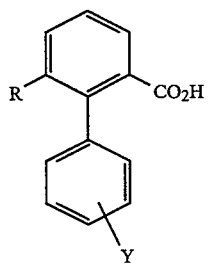 | H | 14k | 99% |
| 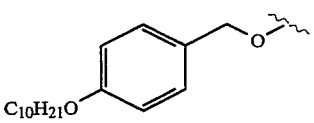 | m-CO$_2$Et | 14l | 54% |
| 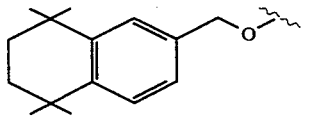 | m-CO$_2$H | 14m | 54% |
| 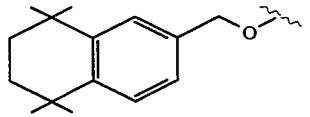 | H | 14n | 90% |
| 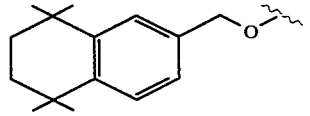 | p-C(CH$_3$)$_3$ | 14o | 99% |
| 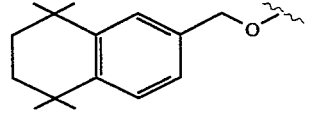 | p-(CH$_2$)$_2$OH | 14b | 88% |
| 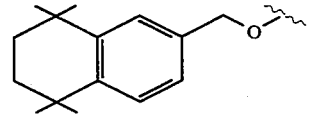 | m-CH$_2$CO$_2$H | 14q | 72% |

TABLE 2

Biological Data for Compounds of Structure 28 and 30 (Type IB):

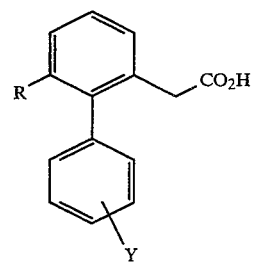

| R | Y | Structure Number | % Inhibition of PLA$_2$ at 100 μM |
|---|---|---|---|
| (styryl group) | m-CO$_2$H | 28a | 28% |
| (1,1,4,4-tetramethyltetralinyl propenyl) | m-CO$_2$H | 28b | 96% |
| (tetramethyl-tetrahydroanthracenyl) | m-CO$_2$H | 28c | 93% |
| 3,4-bis(pentyloxy)benzyloxy (C$_5$H$_{11}$O-) | m-CO$_2$H | 30a | 96% |
| 3,4-bis(cyclopentyloxy)benzyloxy | m-CO$_2$H | 30b | 79% |
| 4-(decyloxy)benzyloxy (C$_{10}$H$_{21}$O-) | m-CO$_2$H | 30c | 99% |
| (adamantyl, methoxy benzyloxy, CH$_3$O-) | m-CO$_2$H | 30d | 97% |
| (tetramethyltetralinyl methyleneoxy) | H | 30e | 59% |
| (tetramethyltetralinyl methyleneoxy) | m-CO$_2$H | 30f | 80% |

TABLE 3
Biological Data for Compounds of Structure 37 (Type IC):
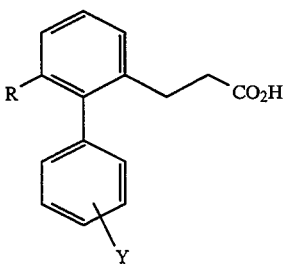
| R | Y | Structure Number | % Inhibition of PLA$_2$ at 100 μM |
|---|---|---|---|
| 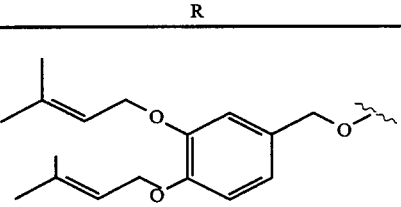 | m-CO$_2$H | 37a | 55% |
| 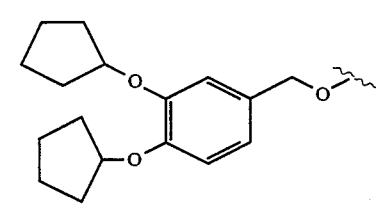 | m-CO$_2$H | 37b | 51% |
| 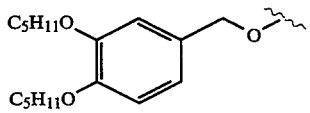 | m-CO$_2$H | 37c | 59% |
| 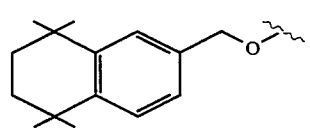 | m-CO$_2$H | 37d | 54% |
TABLE 4
Biological Data for Compounds of Structure 39 (Type ID):
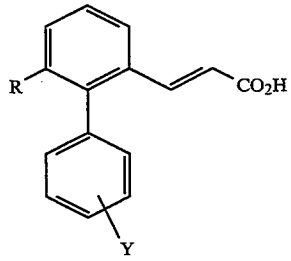
| R | Y | Structure Number | % Inhibition of PLA$_2$ at 100 μM |
|---|---|---|---|
| 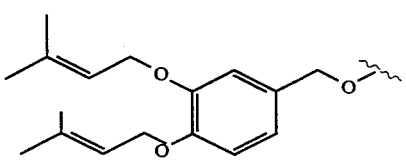 | m-CO$_2$H | 39a | 73% |

TABLE 4-continued
Biological Data for Compounds of Structure 39 (Type ID):
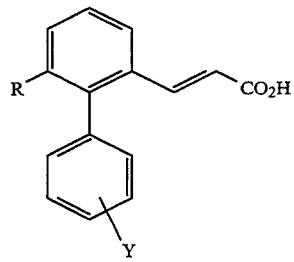
| R | Y | Structure Number | % Inhibition of PLA$_2$ at 100 µM |
|---|---|---|---|
| 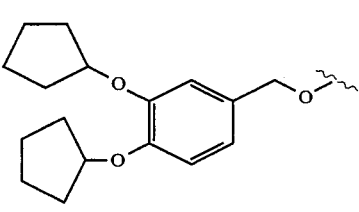 | m-CO$_2$H | 39b | 86% |
| 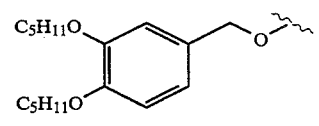 | m-CO$_2$H | 39c | 59% |
| 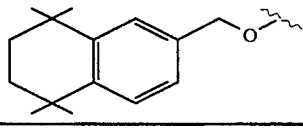 | m-CO$_2$H | 39d | 72% |
TABLE 5
Biological Data for Compounds of Structure 44 and 48 (Type IE):
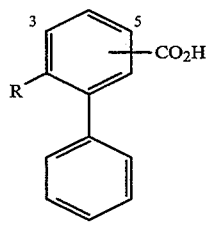
| R | Y | Structure Number | % Inhibition of PLA$_2$ at 100 µM |
|---|---|---|---|
| 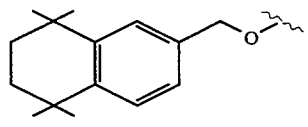 | 5-CO$_2$H | 44 | 70% |
| 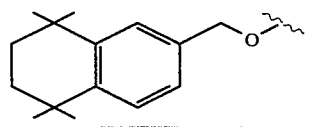 | 3-CO$_2$H | 48 | 88% |
Compounds of Type IE preferably conform to one of the following structures:

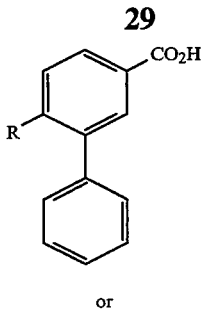

or

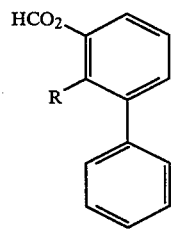

(IE₁)

(IE₂)

salts include salts derived from triethanolamine, N-methylglucamine, tris(hydroxymethyl)aminomethane, and L-lysine.

The concentration of active ingredient(s), or compound(s) of the invention, in such formulations will generally be from about 0.005 to about 10.0 wt %, with quantities of about 0.01 to about 5 wt % preferred.

Additives such as carriers, colorants, perfumes, vehicles, stabilizers, flow control agents and other pharmaceutically acceptable excipients can be used. Additionally, one or more other active ingredient(s) may be included.

The concentration of additives, i.e., ingredients other than the compound(s) of the invention, will generally be from about 90 to 99.995 wt %.

ADMINISTRATION

The compounds of the invention, their isomers and pharmaceutically acceptable derivatives or analogs thereof, may be administered to any subjects in need of treatment for inflammatory conditions, e.g., psoriasis, arthritis, and the like. While human subjects are preferred, the subjects may also be mice or other mammalian species.

The formulations discussed above may be adapted for administration via nasal, intravenous, intramuscular, opthalmic, buccal, oral or topical routes. Transdermal, i.e., topical, and oral administration are the preferred routes.

TABLE 6

Biological Data for Compounds of Structure 52 and 57 (Type II):

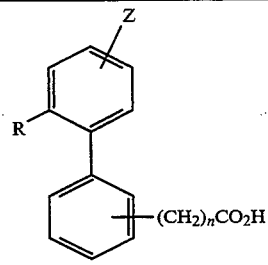

Z = H

| R | n | position | Structure Number | % Inhibition of PLA$_2$ at 100 ∞M |
|---|---|---|---|---|
| (tetrahydronaphthyl-CH₂O-) | 0 | meta | 52a | 83% |
| (tetrahydronaphthyl-CH₂O-) | 0 | para | 52b | 66% |
| (tetrahydronaphthyl-CH₂O-) | 0 | ortho | 52c | 72% |
| (tetrahydronaphthyl-CH₂O-) | 1 | meta | 57 | 92% |

Formulations

Compositions or formulations may contain one or more of the compounds themselves. They may also contain isomers and/or pharmaceutically acceptable derivatives or analogs, such as salts, e.g., succinates, acetates, hydrochlorides, alkali metal salts, ammonium salts, or alkylammonium salts. Examples of alkali metal salts are sodium and potassium salts. Alkylammonium Suitable dosage forms for administration include pills, tablets, capsules, liquid compositions (administrable by injection, ingestion, or application to the surface of the skin or to other body parts), creams, gels, lotions, ointments and the like.

DESCRIPTION OF SPECIFIC EMBODIMENTS

In the following examples, all temperatures are given in degrees Centigrade. Melting points were determined on an electrothermal apparatus and are not corrected. Proton and carbon-13 nuclear magnetic resonance ($^1$H and $^{13}$C NMR) spectra were recorded on a Bruker AM-300 or a Varian Gemini 300 spectrometer. All spectra were determined in $CDCl_3$, DMSO-$d_6$, $CD_3OD$, or $D_2O$ unless otherwise indicated. Chemical shifts are reported in $\delta$ units relative to tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublets; ddd doublet of doublet of doublet; and dt, doublet of triplets. Infrared spectra were determined on a Perkin-Elmer 1800 FT-IR spectrometer from 4000 cm$^{-1}$ to 400 cm$^{-1}$, calibrated to the 1601 cm$^{-1}$ absorption of a polystyrene film, and are reported in reciprocal centimeters (cm$^{-1}$). Mass spectra were recorded on a Kratos MS-50 or a Finnegan 4500 instrument utilizing direct chemical ionization (DCI, isobutene) or fast atom bombardment (FAB). Ultraviolet spectra were determined on a Hewlett Packard 8452 diode array spectrophotometer in the solvent indicated.

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure with the indicated solvents. Reversed-phase analytical thin-layer chromatography was carried out on precoated reverse-phase plates and visualized using UV light or iodine vapors. Reversed-phase column chromatography was performed in a glass column using Baker Octadecyl ($C_{18}$), 40 $\mu$m.

All evaporations of solvent were performed under reduced pressure. Celite is a registered trademark of the Johns-Manville Products Corporation for diatomaceous earth. Florisil is a registered trademark of US Silica.

EXAMPLES

The following examples illustrate the preparation of compounds conforming to Formula I and Formula II.

Experimental Procedures for Biaryl Phosoholipase A2 Inhibitors: Type IA

Example 1: General Procdure for Synthesis of Triflates

The synthesis of 2-trifluoromethylsulphonyloxy-3methoxybenzaldehyde (2) is illustrative of the procedure:

o-Vanillin (4.00 g., 26.3 mmol, 1 equiv.) is dissolved in 115 mL of dry methylene chloride. 4-Dimethylaminopyridine (11.7 g., 95.8 mmol, 3.64 equiv.) is added, and the flask cooled to 0° C. Trifluoromethanesulfonylanhydride (5.09 mL, 30.3 mmol, 1.15 equiv.) is added dropwise via syringe over 5 min. The mixture is stirred for 30 min. at 0° C., and then poured into 1N HCl. The organic layer is washed twice with 1N HCl, once with water, and then brine. The organic phase is dried ($MgSO_4$), and then concentrated in vacuo, yielding a crude solid. Chromatography on silica gel using 25% then 50% methylene chloride/hexane affords 2-trifluoromethylsulphonyloxy-3-methoxybenzaldehyde (2) (5.52 g., 19.4 mmol, 74% yield) as a white crystalline solid, analytically identical to the known material (see: Saa, J. M.; et al. *J. Org. Chem.* 1992, 57, 678): mp=29.5–31.5° C.; UV$_{max}$ ($CHCl_3$) 244 nm ($\epsilon$=8641) , 314 nm ($\epsilon$=3139); $^1$H NMR (300 MHz, $CDCl_3$) $\delta$10.23 (s, 1H, CHO), 7.51 (dd, J=2, 8 Hz, 1H, ArH), 7.44 (dd, J=8, 8 Hz, 1H, ArH), 7.28 (dd, J=2, 8 Hz, 1H, ArH), 3.95 (s, 3H, $OCH_3$); $^{13}$C NMR (75 MHz, $CDCl_3$) $\delta$186.69 (C=O), 151.68, 129.53, 129.08, 121.13, 120.79, 118.59, 116.54, 56.58, ($OCH_3$); IR (KBr) 1706, 1608, 1580, 1482, 1422, 1294, 1230, 1210, 1132, 946, 888 cm$^{-1}$; MS (DCI)m/e 285 (MH+). Anal. Calcd for $C_9H_7F_3O_5S$: C, 38.04; H, 2.48. Found: C, 37.99; H, 2.43.

For 3'-carboethoxy-6-carboethoxy [1, 1'-biphenyl]2-trifluoromethane-sulphonate (8a): scale=0.982 mmol, yield =83%; chromatographed on silica using $CH_2Cl_2$/hexane; $^1$H NMR (300 MHz, $CDCl_3$) $\epsilon$8.09 (ddd, J=2, 2, 7 Hz, 1H, ArH), 7.92 (m, 2H, ArH), 7.57–7.43 (m, 4H, ArH), 4.35 (q, J=7 Hz, 2H, $CO_2CH_2$), 4.03 (q, J=7 Hz, 2H, $CO_2CH_2$), 1.03 (t, J=7 Hz, 3H, $CO_2CH_2CH_3$), 0.94 (t, J=7 Hz, 3H, $CO_2CH_2CH_3$); $^{13}$C NMR (75 MHz, $CDCl_3$) $\delta$166.18 (C=O), 166.09 (C=O), 147.21, 135.05, 134.36, 134.05, 133.82, 130.54, 130.37, 129.77, 129.52, 129.40, 128.07, 124.67, 120.29, 61.51, 61.13, 14.27, 13.61; IR (film) 3074, 2986, 1722, 1426, 1368, 1296, 1240, 1214, 1140, 950, 850 cm$^{-1}$; (DCI) m/e 447 (MH+), 401 ($MC_2H_{5O}$) . Anal. Calcd for $C_{19}H_{17}F_3O_7S$: C, 51.12; H, 3.84. Found: C, 51.30; H, 3.93.

Example 2: General Procedures for the Synthesis of Stannanes

Procedure A: Palladium-catalyzed Stannylation of Aryl Halides

The synthesis of 3-carboethoxyphenyltributyl-stannane (3a) is illustrative:

Ethyl 3-bromobenzoate (13.8 mL, 86.2 mmol, 1 equiv.) and bis(tributyl)tin (100 g., 172 mmol, 2 equiv.) are dissolved under argon in 380 mL of toluene. Tetrakis (triphenytphosphine)-palladium(0) (5.00 g. , 4.33 mmol, 0.15 equiv. ) is added, and the mixture heated to reflux overnight (ca. 16 h. ). The reaction is allowed to cool to room temperature, and is then filtered through celite. The liltrate is concentrated in vacuo, and the residue is chromatographed on silica gel using hexane, then 10% methylene chloride/hexane as the eluent. 3 -Carboethoxyphenyltributyl-stannane (3a) is obtained as a clear oil (21.1 g., 48.1 mmol, 56%, 95% purity): $^1$H NMR (300 MHz, $CDCl_3$) $\delta$8.15 (s, 1H, ArH), 7.97 (ddd, J=2, 2, 8 Hz, 1H, ArH), 7.62 (ddd, J=2, 2, 8 Hz, 1H, ArJ), 7.39 (dd, J=8, 8 Hz, 1H, ArH), 4.37 (q, J=8 Hz, 2H, $CO_2CH_2$), 1.54 (m, 6H, 3×$SnCH_2$), 1.37 (m, 9H, 3×$SnCH_2CH_2$ and $CO_2CH_2CH_3$), 1.10 (m, 6H, 3×$SnCH_2CH_2CH_2$), 0.94 (t, J=8 Hz, 9H, 3×$CH_3$) .

For 3-(trifluoromethyl)phenyl-tributylstannane (3d): scale =13.3 mmol, yield =52%; chromatographed on silica gel using pentane; $^1$H NMR (300 MHz, $CDCl_3$) $\delta$7.85 (s, 1H, ArH), 7.75 (m, 1H, ArH), 7.60 (m, 1H, ArH), 1.65 (m, 6H, 3×$SnCH_2$), 1.47 ,(m, 12H, 3×$SnCH_2CH_2CH_2CH_3$), 0.91 (t, J=8 Hz, 9H, 3×$CH_3$ ) .

For 4-carbomethoxyphenyltributylstannane (3f): see Hylarides, et al., *J. Organomet. Chem.* 1989, 367, 259–265.

Procedure B: Trapping of Anions by Tri (n-butyl) stannyl chloride

The synthesis of (E)-2-[(5,5,8,8-tetramethyl-5,6,7,8-tetrahydro)-7-naphthalenyl]-1-propenyltributylstannane (9) is illustrative Bromomethyltriphenylphosphonium bromide (6.07 g., 13.9 mmol, 1.05 equiv.) is suspended in 28 mL of dry toluene. The suspension is cooled to −40° C. Potassium tert-butoxide (95%, 1.57 g., 13.3 mmol, 1 equiv.) is added and the flask allowed to warm to −20° C. over 30 min. The mixture is re-cooled to −40° C., and 7-acetyl (5,5,8,8-tetramethyl-5,6,7,8-tetrahydronaphthalene) (3.05 g., 13.3 mmol, 1 equiv.) dissolved in 10 mL of toluene is added dropwise. The flask is allowed to warm to −30° C. and stir for 2 hours. The mixture is poured into half-saturated ammonium chloride solution, and extracted with EtOAc and ether. The organic phase is washed with brine, dried (MgSO4) and then concentrated in vacuo. Chromatography on silica gel using hexane as the eluent affords (E)-2-[(5,5,8,8-tetramethyl-5,6,7,8-tetrahydro)-2-naphthalenyl]-1-bromopropene (1.70 g., 5.54 mmol, 42%) as a 17:1 mixture of E:Z olefin isomers: Data for E isomer: $^1$H NMR (300 MHz, CDCl3) δ7.29 (d, J=8 Hz, 1H, ArH), 7.27 (d, J=2 Hz, 1H, ArH), 7.11 (dd, J=2, 8 Hz, 1H, ArH), 6.40 (q, J =1 Hz, 1H, C=CHBr), 2.23 (d, J=1 Hz, 3H, C=CCH3), 1.70 (s, 4H, CH2CH2), 1.31 ( s, 6H, 2×CH3), 1.29 (s, 6H, 2×CH3).

(E)-2-[(5,5,8,8-tetramethyl-5,6,7,8-tetrahydro)-2-naphthalenyl]-1-bromopropene (0.680 g., 2.20 mmol, 1 equiv.) is dissolved in 6.8 mL of dry THF. The solution is cooled to −78° C. and t-BuLi (1.7M in hexane, 2.74 mL, 4.62 mmol, 2.1 equiv.) is added dropwise. After stirring for 30 min. at −78° C., tri(n-butyl)tin chloride (0.60 mL, 2.2 mmol, 1 equiv.) is added. The mixture is stirred at −78° C. for 15 min. and the cooling bath is removed. After 15 min., the solution is poured into water, and extracted with ether. The ether extracts are washed with brine, dried (MgSO4) and then concentrated in vacuo. The yield of crude (E)-2-[(5,5,8,8-tetramethyl-5,6,7,8-tetrahydro)-2-naphthalenyl]-1-propenyltributylstannane (9) is 1.50 g. This material is suitable for use in subsequent reactions without purification: $^1$H NMR (300 MHz, CDCl3) δ7.40 (bs, 1H, ArH), 7.28 (m, 2H, ArH), 6.23 (m, 1H, C=CH), 2.21 (s, 3H, C=CCH3), 1.69 (s, 4H, CH2CH2), 1.60 (m, 6H, 3×SnCH2), 1.35 (m, 12H, 3×SnCH2CH2CH2), 1.32 (s, 6H, 2×CH3) , 1.30 (s, 6H, 2×CH3), 0.95 (m, 9H, 3×CH3) .

For 4-(1,1-dimethylethyl)phenyl-tributylstannane (3c): From 4-tertbutylbromobenzene; scale=18.7 mmol, yield =100%; $^1$H NMR (300 MHz, CDCl3) δ7.39 (m, 4H, ArH), 1.54 (m, 6H, 3×SnCH2), 1.36 (m, 6H, 3×SnCH2CH2CH2), 1.34 (s, 9H, C(CH3)3), 1.08 (m, 6H, 3×SnCH2CH2CH2), 0.90 (m, 9H, CH3).

For 4-(2-tertbutyldimethylsilyloxy-1-ethyl))phenyl-tributyl-stannane (3e): From 4-bromophenethyl alcohol by silylation using tertbutytdimethylsilyl chloride, triethylamine, N'N-dimethylaminopyridine in methylene chloride, followed by anion trapping; scale=5.24 mmol, yield =41%; chromatographed on silica gel using hexane; $^1$H NMR (300 MHz, CDCl3) δ7.36 (d, J=8 Hz, 2H, ArH), 7.16 (d, J=8 Hz, 2H, ArH), 3.79 (t, J=7 Hz, 2H, CH2O), 2.79 (t, J=7 Hz, 2H, ArCH2), 1.50 (m, 6H, 3×SnCH2), 1.30 (m, 6H, 3×SnCH2CH2CH2) , 1.02 (m, 6H, 3×SnCH2CH2CH2), 0.87 (m, 9H, CH3), 0.86 (s, 9H, SiC(CH3)3), −0.03 (s, 6H, 2×CH3); $^{13}$C NMR (75 MHz, CDCl3) δ138.95, 138.74, 136.40, 128.88, 64.67, 39.62, 29.10, 27.41, 20.87, 13.71, 9.51; IR (film) 2956, 2928, 2856, 1464, 1254, 1098, 834 cm$^{-1}$; MS (DCI) m/e 527 (MH+), 469 (M-C4H9), 395 (M-C6H15SiO).

For (3-carboethoxymethyl)phenyl-tributylstannane (3g): Obtained from ethyl (4-bromophenyl)acetate via treatment with lithium diisopropylamide (1.1 equiv.) in THF at −78° C. (20 min.), followed by t-butyllithium (2 equiv., 55 min. at −78° C.), and then trapping with n-Bu3SnCl as above; scale =6.38 mmol, yield =42%; chromatographed on silica gel using EtOAc/hexane; $^1$H NMR (300 MHz, CDCl3) δ7.36 (s, 1H, ArH), 7.31-7.20 (m, 3H, ArH), 4.16 (q, J=7 Hz, 2H, CO2CH2), 3.59 (s, 2H, ArCH2CO2), 1.72-1.44 (m, 6H, 3×SnCH2), 1.42-1.22 (m, 15H, 3×SnCH2CH2CH2and CO2CH2CH3), 0.94 (m, 9H, 3×CH3).

Example 3: General Procedure for the Synthesis of Biaryls via Palladium-catalyzed Coupling of Triflates and Stannanes The synthesis of 2-methoxy-3'-carboethoxy-[1,1'-biphenyl]-6-carboxaldehyde (4a) is illustrative:

Stannane 3a (4.25 g., 9.68 mmol, 1.5 equiv.) and triflate 2 (1.80 g., 6.44 mmol, 1 equiv.) are suspended in 17 mL of DMF. Bis(triphenylphosphine)palladium dichloride (0.68 g., 0.969 mmol, 0.15 equiv.) and LiCl (0.82 g., 19.3 mmol, 3 equiv.) are added and the mixture is heated to 150° C. After 45 min., more bis(triphenylphospine)palladium dichloride (0.2 g., 0.285 mmol, 0.04 equiv.), more LiCl (0.4 g., 9.42 mmol, 1.46 equiv.), and more stannane 3a (0.8 g., 1.82 mmol, 0.28 equiv.) is added, and heating is continued for 2 hours. (The reaction generally turns from yellow-brown to black when complete.) The mixture is allowed to cool to room temperature, and 15 mL of aqueous saturated KF and 10 mL of ether are added. The mixture is stirred for 30 min., and then filtered through celite to remove the tin salts. The filter cake is washed with EtOAc and ether, and the combined filtrates are washed with water, followed by 3% aqueous ammonia solution and then brine. The organic phase is dried (MgSO4) and then concentrated in vacuo. Chromatography on silica gel using 25%, 50% then 75% methylene chloride/hexane affords 2-methoxy-3'-carboethoxy-[1,1'-biphenyl]-6-carboxaldehyde (4a) (1.72 g., 6.06 mmol, 94%) as a slightly yellow oil which crystallizes on standing: mp=67°-69° C.; UV$_{max}$ (CHCl3) 242 nm (ε=15819), 324 nm (ε=3953); $^1$H NMR (300 MHz, CDCl3) δ9.70 (s, 1H, CHO), 8.09 (ddd, J=2, 2, 7 Hz, 1H, ArH), 7.99 (s, 1H, ArH), 7.62 (dd, J=2, 8 Hz, 1H, ArH), 7.49 (m, 3H, ArH), 7.19 (dd, J=2, 8 Hz, 1H, ArH), 4.37 (q, J=7 Hz, 2H, CO2CH2), 3.76 (s, 3H, OCH3), 1.34 (t, J=7 Hz, 3H, CO2CH2CH3); $^{13}$C NMR (75 MHz, CDCl3 ) δ191.93 (C=O), 166.31 (C=O), 156.98, 135.27, 133.73, 133.57, 131.92, 130.42, 129.17, 129.09, 128.09,119.30, 115.95, 61.14, 56.06, 14.32; IR (film) 2980, 2940, 2838, 1718, 1694, 1468, 1294, 1260, 1234, 1110, 794 cm$^{-1}$; MS (DCI) m/e 285 (MH+), 239 (M—C2H5O). Anal. Calcd for C17H16O4.0.25 H2O: C, 70.69; H, 5.76. Found: C, 70.64; H, 5.59.

For 6-carboethoxy-2-[(E)-2-[(5,5,8,8-tetramethyl-5,6,7,8-tetrahydro)-2-naphthalenyl]-1-propenyl]-3'-carboethoxy-[1,1'-biphenyl](10a): From stannane 9a and triflate 8a; temperature=130° C., scale=0.445 mmol, yield=84%; chromatographed on silica gel using EtOAc/hexane; UVmax (EtOH) 212 nm (ε=30865), 278 nm (ε=11586 ); $^1$H NMR (300 MHz, CDCl3) δ8.03 (ddd, J=2, 2, 8 Hz, 1H, ArH), 7.90 (s, 1H, ArH), 7.78 (dd, J=2, 8 Hz, 1H, ArH), 7.52 (dd, J=2, 8 Hz, 1H, ArH), 7.44 (dd, J=8, 8 Hz, 1H, ArH), 7.39 (m, 2H, ArH), 7.16 (d, J=8 Hz, 1H, ArH), 7.00 (d, J=2 Hz, 1H, ArH), 6.95 (dd, J=2, 8 Hz, 1H, ArH), 6.28 (s, 1H, C=CH), 4.31 (q, J=7 Hz, 2H, $CO_2CH_2$), 4.01 (q, J=7 Hz, 2H, $CO_2CH_2$), 2.08 (s, 3H, C=$CCH_3$), 1.62 (s, 4H, $CH_2CH_2$), 1.32 (t, J=7 Hz, 3H, $CH_2CH_3$), 1.22 (s, 6H, 2×$CH_3$), 1.16 (s, 6H, 2×$CH_3$), 0.94 (t, J=7 Hz, 3H, $CH_2CH_3$); $^{13}C$ NMR (75 MHz, $CDCl_3$) δ168.20 (C=O), 166.47 (C=O), 144.46, 144.06, 140.44, 140.37, 140.26, 138.53, 137.53, 133.82, 132.92, 131.82, 130.32, 130.02, 128.24, 128.04, 127.75, 127.21, 126.30, 125.73, 123.91, 123.11, 60.91, 60.85, 35.11, 34.99, 34.20, 34.04, 31.73, 17.23, 14.27, 13.70; IR (film) 2960, 2926, 1722, 1292, 1234, 1136 $cm^{-1}$; MS (DCI) m/e 525 (MH+), 479 (M—$C_2H_5O$). Anal. Calcd for $C_{35}H_{40}O_4$ .0.4 $H_2O$: C, 79.03; H, 7.73. Found: C, 79.09; H, 7.62.

For 2-methoxy- [1, 1'-biphenyl]-6-carboxaldehyde (4b): From phenyltributylstannane (3b) and triflate 2; scale =6.34 mmol, yield =54%; chromatographed on silica gel using $CH_2Cl_2$ hexane; mp=42°-43° C.; $UV_{max}$ (EtOH) 224 nm (ε=22349), 322 nm (ε=3702); $^1H$ NMR (300 MHz, $CDCl_3$) δ9.74 (s, 1H, CHO), 7.65 (d, J=8 Hz, 1H, ArH), 7.49-7.32 (m, 6H, ArH), 7.19 (d, J=8 Hz, 1H, ArH), 3.80 (s, 3H, $OCH_3$); $^{13}C$ NMR (75 MHz, $CDCl_3$) δ192.46 (C=O), 157.00, 135.40, 134.92, 133.16, 131.09, 128.78, 128.00, 127.94, 119.05, 115.92, 56.03; IR (KBr) 2840, 1680, 1590, 1570, 1255, 1235 $cm^{-1}$; MS (DCI) m/e 213 (MH+), 195 (M—OH). Anal. Calcd for $C_{14}H_{12}O_2$.0.1 $H_2O$: C, 78.57; H, 5.55. Found: C, 78.24; H, 5.76.

For 2 -methoxy - 3'-trifluoromethyl-[1,1'- biphenyl]-6-carboxaldehyde (4c): From triflate 2 and 3-trifluoromethylphenyl-tributylstannane (3d); scale=6.34 mmol, yield =51%; chromatographed on silica gel using $CH_2Cl_2$/hexane; mp=98°-99° C.; $UV_{max}$ (EtOH) 218 nm (ε=21188), 322 nm (ε=3809); $^1H$ NMR (300 MHz, $CDCl_3$) δ6 9.73 (s, 1H, CHO), 7.70-7.48 (m, 6H, ArH), 7.21 (d, J=8 Hz, 1H, ArH), 3.80 (s, 3H, $OCH_3$); $^{13}C$ NMR (75 MHz, $CDCl_3$) δ191.66 (C=O), 156.87, 135.24, 134.38, 134.15, 132.95, 130.50 (d, $J^2_{c\text{-}f}$=32 Hz), 129.47, 128.49, 127.70 (d, $J^3_{c\text{-}f}$=4 Hz) 124 75 (d, $J^3_{c\text{-}f}$=4 Hz), 123.61 (q, $J^1_{3c\text{-}f}$=271 Hz), 119.49, 116.00, 56.04; IR (KBr) 2840, 1687, 1590, 1340, 1267, 1242, 1110 $cm^{-1}$; MS (DCI) m/e 281 (MH+). Anal. Calcd for $C_{15}H_{11}F_3O_2$: C, 64.29; H, 3.95. Found: C, 64.35; H, 3.93.

Example 4: General Procedure for the Oxidation of Aldehydes to Acids

The synthesis of 2-methoxy-3'-carboethoxy-[1,1'-biphenyl]-6-carboxylic acid (5a) is illustrative:

Aldehyde 4a (0.512 g., 1.80 mmol, 1 equiv.) is dissolved in 17 mL of THF and 13 mL of $H_2O$. The solution is cooled to 0° C. Sulfamic acid (0.525 g., 5.41 mmol, 3 equiv. ) is then added, followed by a solution of sodium chlorite (80% tech., 0.612 g., 5.41 mmol, 3 equiv. ) in 4 mL of $H_2O$. The mixture is stirred for 15 min. at 0° C., and then poured into EtOAc and water. The aqueous layer is extracted thrice with EtOAc, and the combined organic-phase is washed with brine. The organic phase is dried ($MgSO_4$) and then concentrated in vacuo to afford 2-methoxy-3'-carboethoxy-[1,1'-biphenyl]-6-carboxylic acid (5a) as a pale yellow oil (0.583 g., 1.80 mmol, 100%): $^1H$ NMR (300 MHz, $CDCl_3$) δ 10.17 (br, 1H, $C_2H$), 8.02 (ddd, J=2, 2, 8 Hz, 1H, ArH), 7.94 (s, 1H, ArH), 7.56 (d, J=8 Hz, 1H, ArH), 7.41 (m, 3H, ArH), 7.15 (d, J=8 Hz, 1H, ArH), 4.19 (q, J=7 Hz, 2H, $CO_2CH_2$), 3.,73 (s, 3H, $OCH_3$), 1.39 (t, J=7 Hz, 3H, $CH_2CH_3$).

For 2-[(3-acetoxy-4-pentyloxy)phenyl]methoxy-[1,1'-biphenyl]-6-carboxylic acid (14f): From ether 16f (see Example 11); scale=1.18 mmol, yield=63%; chromatographed on silica gel using EtOAc/hexane; mp=128°-129° C.; $UV_{max}$ (EtOH) 206 nm (ε=30285), 222 nm (ε=26802), 282 nm (ε=3915); $^1H$ NMR (300 MHz, $CDCl_3$) δ 7.53 (d, J=8 Hz, 1H, ArH), 7.37-7.25 (m, 6H, ArH), 7.11 (d, J=8 Hz, 1H, ArH), 6.90 (dd, J=2, 8 Hz, 1H, ArH), 6.80 (d, J=8 Hz, 1H, ArH), 6.73 (d, J=2 Hz, 1H, ArH), 4.90 (s, 2H, $ArCH_2O$), 3.91 (t, J=7 Hz, 2H, $RCH_2OAr$), 2.27 (s, 3H, $CH_3CO$), 1.72 (m, 2H, $CH_2CH_2OAr$), 1.36 (m, 4H, $CH_3CH_2CH_2$), 0.89 (t, J=7 Hz, 3H, $CH_3$); $^{13}C$ NMR (75 MHz, $CDCl_3$) δ 170.92 (C=O), 168.91 (C=O), 162.93, 156.03, 150.03, 139.85, 136.32, 132.80, 131.40, 129.58, 129.11, 128.39, 127.74, 124.97, 122.93, 121.31, 117.30, 113.17, 70.10, 68.72, 28.79, 28.04, 22.36, 20.55, 14.02; IR (KBr) 3440 (OH), 2960, 2870, 1770 (C=O), 1700 (C=O), 1510, 1275, 1255 $cm^1$; MS (DCI) m/e 448 (M+), 431 (M—OH), 389, 235. Anal. Calcd for $C_{27}H_{28}O_6$: C, 70.88; H, 6.17. Found: C, 70.56; H, 6.07.

For 2-[4-(1-adamantyl)-3-methoxyphenyl]methoxy-[1,1'-biphenyl]-6-carboxylic acid (14 g): From ether 16 g; scale=0.33 mmol, yield=59%; chromatographed on silica gel using $MeOH/CH_2Cl_2$; mp=95°-100° C.; $UV_{max}$ (EtOH) 206 nm (ε=44086), 282 nm (ε=4908); $^1H$ NMR (300 MHz, $CDCl_3$) δ 7.55 (d, J=8 Hz, 1H, ArH), 7.40-7.29 (m, 6H, ArH), 7.18 (d, J=8 Hz, 1H, ArH), 7.09 (d, J=8 Hz, 1H, ArH), 6.89 (d, J=8 Hz, 1H, ArH), 6.60 (s, 1H, ArH), 4.98 (s, 2H, $ArCH_2O$), 3.63 (s, 3H, $CH_3O$), 2.04 (s, 9H, adamantyl), 1.75 (s, 6H, adamantyl); $^{13}C$ NMR (75 MHz, $CDCl_3$) δ 158.91 (C=O), 137.80, 136.54, 135.33, 131.56, 129.58, 128.41, 127.71, 127.09, 126.30, 122.68, 118.11, 116.80, 109.65, 70.30, 54.94, 40.51, 37.10, 36.80, 29.05; IR (KBr) 3440 (OH), 2903, 1700 (C=O), 1580, 1450, 1260 $cm^{-1}$; MS (DCI) m/e 469 (MH+), 468 (M+), 467 (MH−), 451 (M—OH), 255. Anal. Calcd for $C_{31}H_{32}O_4.H_2O$: C, 76.36; H, 6.79. Found: C, 76.51; H, 7.02.

For 2-[(3,4-bispentyloxy)phenyl]methoxy-[1,1'-biphenyl]-6-carboxylic acid (14i): From ether 16i; scale=1.0 mmol, yield=63%; chromatographed on silica gel using EtOAc/hexane; mp=97°-98° C.; $UV_{max}$ (EtOH) 208 nm (ε=49471), 284 nm (δ=5533); $^1H$ NMR (300 MHz, $CDCl_3$) δ 7.53 (d, J=8 Hz, 1H, ArH), 7.40-7.26 (m, 6H, ArH), 7.17 (d, J=8 Hz, 1H, ArH), 6.76 (d, J=8 Hz, 1H, ArH), 6.56 (dd, J=2, 8 Hz, 1H, ArH), 6.62 (d, J=2 Hz, 1H, ArH), 4.93 (s, 2H, $ArCH_2O$), 3.95 (t, J=7 Hz, 2H, $RCH_2O$), 3.80 (t, J=7 Hz, 2H, $RCH_2O$), 1.82-0.90 (m, 18H, pentyl); $^{13}C$ NMR (75 MHz, $CDCl_3$) δ 172.64 (C=O), 156.11, 149.21, 148.44, 136.48, 132.75, 131.55, 129.55, 129.30, 128.32, 127.64, 127.06, 122.74, 118.89, 117.17, 113.47, 112.02, 70.61, 69.32, 68.95, 28.96, 28.20, 22.50, 14.06; IR (KBr) 3440 (OH), 2930, 2860, 1670 (C=O), 1530, 1310, 1260 $cm^{-1}$; MS (DCI) m/e 477 (MH+), 459 (M—OH), 263. Anal. Calcd for $C_{30}H_{36}O_5.0.5$ $H_2O$: C, 74.20; H, 7.68. Found: C, 74.45; H, 7.42.

For 2-[(3,4-bispentyloxy)phenyl]methoxy-[1,1'-biphenyl]-3'-trifluoromethyl-6-carboxylic acid (14j): From ether 16j; scale=0.33 mmol, yield=57%; chromatographed on silica gel using $MeOH/CH_2Cl_2$; mp=76°-77° C.; $UV_{max}$ (EtOH) 206 nm (ε=41471), 284 nm (ε=5637); $^1H$ NMR (300 MHz, $CDCl_3$) δ 7.60-7.43 (m, 5H, ArH), 7.37 (d, J=8 Hz, 1H, ArH), 7.20 (d, J=8 Hz, 1H, ArH), 6.76 (d, J=8 Hz, 1H, ArH), 6.65 (dd, J=2, 8 Hz, 1H, ArH), 6.60 (d, J=2 Hz, 1H, ArH), 4.94 (s, 2H, ArCH$_2$O), 3.97–3.77 (m, 4H, 2×ArOCH$_2$), 1.84–0.89 (m, 18H, pentyl); $^{13}$C NMR (75 MHz, CDCl$_3$) δ 172.04 (C=O), 156.05, 149.20, 148.66, 137.52, 133.01, 131.20 (d, J $^2_{c\text{-}f}$=18 Hz), 129.70, 128.93 (d, J $^3_{c\text{-}f}$=4 Hz), 127.94, 125.01 (q, J $^1_{c\text{-}f}$210 Hz), 122.99, 121.55, 121.43, 119.22, 117.13, 114.28, 113.94, 112.25, 112.12, 70.59, 69.28, 68.96, 29.72, 28.95, 28.69, 22.48, 14.05; IR (KBr) 3400 (OH), 2930, 2960, 1700 (C=O), 1590, 1520, 1330, 1300, 1270 cm$^{-1}$; MS (DCI) m/e 544 (M+), 435, 283, 263. Anal. Calcd for C$_{31}$H$_{35}$O$_5$F$_3$: C, 66.18; H, 6.02. Found: C, 66.44; H, 6.15.

For 2-[(4-decyloxy)phenyl]methoxy-[1,1'-biphenyl]-6-carboxylic acid (14k): From ether 16k; scale=0.63 mmol, yield=62%; chromatographed on silica gel using 10% MeOH/CH$_2$Cl$_2$; mp=92°–93° C.; UV$_{max}$ (EtOH) 206 nm (ε=38203), 284 nm (ε=3792); $^1$H NMR (300 MHz, CDCl$_3$) δ 7.54 (d, J=8 Hz, 1H, ArH), 7.39°–7.27 (m, 6H, ArH), 7.16 (d, J=8 Hz, 1H, ArH), 7.07 (d, 2H, J=8 Hz, ArH), 6.81 (d, J=8 Hz, 2H, ArH), 4.94 (s, 2H, ArCH$_2$O), 3.92 (t, J=6 Hz, ArOCH$_2$R), 1.76 (m, 2H, ArOCH$_2$CH$_2$R), 1.44–1.27 (m, 14H, R(CH$_2$)$_7$CH$_3$), 0.89 (t, J=6 Hz, 3H, CH$_3$C); $^{13}$C NMR (75 MHz, CDCl$_3$) δ 173.00 (C=O), 158.69, 156.13, 136.36, 132.83, 131.65, 129.56, 128.49, 128.26, 128.19, 127.65, 127.12, 122.76, 117.44, 114.34, 70.66, 67.99, 53.45, 31.91, 31.61, 29.58, 29.41, 29.34, 29.26, 26.04, 22.69, 14.15; IR (KBr) 3450 (OH), 2925, 1705 (C=O), 1675 (C=O), 1530, 1240, 1267 cm$^{-1}$; MS (DCI) m/e 461 (M+), 247. Anal. Calcd for C$_{30}$H$_{36}$O$_4$: C, 78.23; H, 7.88. Found: C, 78.11; H, 7.85.

For 2-(5,6,7,8-tetrahydro-5,5,8,8-tetramethyl-2-naphthalenyl)methoxy-[1,1'-biphenyl]-6,3'-dicarboxylic acid, 3'-ethyl ester (14l): From ether 16 1; scale=2.97 mmol, yield=78%; recrystallized from CH$_2$Cl$_2$/pentane; UV$_{max}$ (CHCl$_3$) 242 nm (ε=11785), 298 nm (ε=3885); $^1$H NMR (300 MHz, CDCl$_3$) δ 8.02 (ddd, J=2, 2, 8 Hz, 1H, ArH), 798 (s, 1H, ArH), 7.56 (dd, J=1, 8 Hz, 1H, ArH), 7.44 (m, 2H, ArH), 7.38 (t, J=8 Hz, 1H, ArH), 7.20 (dd, J=1, 8 Hz, 1H, ArH), 7.16 (d, J=8 Hz, 1H, ArH), 6.98 (d, J=2 Hz, 1H, ArH), 6.88 (dd, J=2, 8 Hz, 1H, ArH), 4.94 (s, 2H, ArCH$_2$O), 4.33 (q, J=7 Hz, 2H, CO$_2$CH$_2$), 1.60 (s, 4H, CH$_2$CH$_2$), 1.34 (t, J=7 Hz, 3H, CH$_2$CH$_3$), 1.21 (s, 6H, 2×CH$_3$), 1.10 (s, 6H, 2×CH$_3$); $^{13}$C NMR (75 MHz, CDCl$_3$) δ 171.22 (C=O), 166.63 (C=O), 156.32, 144.94, 144.29, 136.94, 134.06, 133.34, 131.93, 130.96, 130.63, 129.98, 128.74, 128.44, 127.75, 126.45, 124.52, 123.72, 122.84, 116.84, 70.52, 60.86, 34.96, 34.15, 34.06, 31.79, 31.67, 14.33, 11.17; IR (KBr) 3260, 3100, 2960, 2926, 1718, 1698, 1576, 1456, 1298, 1262, 1234, 758 cm$^{-1}$; MS (DCI) m/e 487 (MH+), 469 (M—OH), 201 (C$_{15}$H$_{21}$+). Anal. Calcd for C$_{31}$H$_{34}$O$_5$.0.5 H$_2$O: C, 75.13; H, 7.12. Found: C, 75.05; H, 7.10.

For 2-(5,6,7,8-tetrahydro-5,5,8,8-tetramethyl-2-naphthalenyl)methoxy-[1,1'-biphenyl]-6-carboxylic acid (14n): From ether 16n; scale=0.27 mmol, yield=88%; chromatographed on silica gel using MeOH/CH$_2$Cl$_2$; mp=130°–131° C.; UV$_{max}$ (MeOH) 210 nm (ε=37099), 290 nm (ε=2908); $^1$H NMR (300 MHz, CD$_3$OD) δ 7.40–7.21 (m, 7H, ArH), 7.19 (d, J=8 Hz, 1H, ArH), 7.09 (d, J=1 Hz, 1H, ArH). 6.91 (dd, J=2, 8 Hz, 1H, ArH), 4.96 (s, 2H, ArCH$_2$O), 1.65 (s, 4H, CH$_2$CH$_2$), 1.25 (s, 6H, 2×CH$_3$), 1.15 (s, 6H, 2×CH$_3$); $^{13}$C NMR (75 MHz, CD$_3$OD) δ 157.43, 145.83, 145.13, 138.39, 135.61, 135.25, 130.95, 129.46, 128.63, 127.95, 127.41, 125.94, 125.15, 122.36, 116.92, 71.51, 36.23, 36.18, 35.17, 34.98, 32.26, 32.23; IR (KBr) 3448, 2960, 2924, 2858, 1700, 1686, 1450, 1300, 1262, 1070, 758 cm$^{-1}$; MS (DCI) m/e 415 (MH+), 201 (C$_{15}$H$_{21}$+). Anal. Calcd for C$_{28}$H$_{30}$O$_3$.0.4 H$_2$O: C, 79.74; H, 7.36. Found: C, 79.85; H, 7.40.

For 2-(5,6,7,8-tetrahydro-5,5,8,8-tetramethyl-2-naphthalenyl)methoxy-[1,1'-biphenyl]-4'-(1,1-dimethylethyl)-6-carboxylic acid (14o): From ether 16o; scale=0.277 mmol, yield=70%; chromatographed on silica gel using MeOH/CH$_2$Cl$_2$; UV$_{max}$ (CHCl$_3$) 242 nm (ε=7967), 298 nm (ε=3564); $^1$H NMR (300 MHz, CDCl$_3$) δ 7.47 (d, J=8 Hz, 1H, ArH), 7.39–7.11 (m, 8H, ArH), 6.85 (dd, J=2, 8 Hz, 1H, ArH), 4.93 (s, 2H, ArCH$_2$O), 1.62 (s, 4H, CH$_2$CH$_2$), 1.32 (s, 9H, C(CH$_3$)$_3$), 1.17 (s, 6H, 2×CH$_3$), 1.15 (s, 6H, 2×CH$_3$); $^{13}$C NMR (75 MHz, CDCl$_3$) δ 171.58 (C=O), 156.33, 149.85, 144.84, 144.17, 133.68, 133.21, 129.32, 128.14, 126.42, 124.76, 124.63, 123.87, 122.45, 116.47, 70.67, 34.99, 34.55, 34.24, 34.06, 31.90, 31.82, 31.40; IR (KBr) 3430, 2962, 2926, 2864, 1698, 1578, 1454, 1400, 1364, 1298, 1260, 1060 cm$^{-1}$; MS (DCI) m/e 471 (MH+), 425 (M—CO$_2$H), 201 (C$_{15}$H$_{21}$+). Anal. Calcd for C$_{32}$H$_{38}$O$_3$.0.9 H$_2$O: C, 78.94; H, 8.23. Found: C, 78.91; H, 8.04.

For 2-(5,6,7,8-tetrahydro-5,5,8,8-tetramethyl-2-naphthalenyl)methoxy-4'-(2-tertbutyldimethylsilyloxy-1-ethyl)-[1,1'-biphenyl]-6-carboxylic acid: From ether 16p; scale=0.29 mmol, yield=58%; chromatographed on silica gel using EtOAc/MeOH; $^1$H NMR (300 MHz, CDCl$_3$) δ 7.48 (d, J=8 Hz, 1H, ArH), 7.33 (dd, J=8, 8 Hz, 1H, ArH), 7.24–7.14 (m, 6H, ArH), 7.07 (s, 1H, ArH), 6.88 (d, J=8 Hz, 1H, ArH), 4.93 (s, 2H, ArCH$_2$O), 3.83 (t, J=7 Hz, 2H, SiOCH$_2$), 2.83 (t, J=7 Hz, 2H, ArCH$_2$CH$_2$), 1.62 (s, 4H, CH$_2$CH$_2$), 1.22 (s, 6H, 2×CH$_3$), 1.15 (s, 6H, 2×CH$_3$) 0.87 (s, 9H, C(CH$_3$)$_3$), −0.01 (s, 6H, Si(CH$_3$)$_2$); $^{13}$C NMR (75 MHz, CDCl$_3$) δ 156.23, 144.90, 144.22, 137.83, 134.18, 133.62, 132.19, 129.55, 128.66, 128.23, 126.44, 124.67, 123.83, 122.50, 116.53, 70.57, 64.62, 39.49, 35.03, 34.99, 34.21, 34.07, 31.82, 31.72, 25.98, 18.39; IR (film) 2956, 2928, 2858, 1700, 1594, 1578, 1470, 1454, 1408, 1298, 1258, 1096, 832 cm$^{-1}$; MS (DCI) m/e 573 (MH+), 557 (M—OH), 515 (M—C$_4$H$_9$), 441 (M—C$_6$H$_{15}$SiO), 201 (C$_{15}$H$_{21}$+).

Desilylation of the above tertbutyldimethylsilyloxy derivative using tetrabutylammonium fluoride in THF/water affords 2-(5,6,7,8-tetrahydro-5,5,8,8-tetramethyl-2 -naphthalenyl )methoxy-4'-(2-hydroxy-1-ethyl)-[1,1'-biphenyl]-6-carboxylic acid (14p): scale=0.70 mmol, yield=63%; chromatographed on C-18 silica gel using MeOH; mp=201°–203° C.; UV$_{max}$ (EtOH) 222 nm (ε=23370), 206 nm (ε=21641), 294 nm (ε=3161); $^1$H NMR (300 MHz, CDCl$_3$) δ 7.32 (dd, J=2, 8 Hz, 1H, ArH), 7.21 (dd, J=7, 7 Hz, 1H, ArH), 7.13–7.02 (m, 6H, ArH), 6.93 (d, J=2 Hz, 1H, ArH), 6.78 (dd, J=2, 8 Hz, 1H, ArH), 4.81 (s, 2H, ArCH$_2$O), 3.69 (t, J=7 Hz, 2H, SiOCH$_2$), 2.72 (t, J=7 Hz, 2H, ArCH$_2$CH$_2$), 1.49 (s, 4H, CH$_2$CH$_2$), 1.08 (s, 6H, 2×CH$_3$), 1.01 (s, 6H, 2×CH$_3$); $^{13}$C NMR (75 MHz, CDCl$_3$) δ 170.37 (C=O), 156.01, 144.76, 144.11, 137.27, 134.72, 133.49, 133.19, 131.70, 129.45, 128.31, 128.08, 126.27, 124.55, 123.69, 121.81, 115.93, 70.41, 63.07, 38.93, 34.85, 34.80, 34.01, 33.87, 31.54, 31.41; IR (KBr) 3366, 2958, 2926, 2858, 1706, 1454, 1262, 1244, 1048 cm$^{-1}$; MS (DCI) m/e 459 (MH+), 441 (M—OH), 201 (C$_{15}$H$_{21}$+). Anal. Calcd for C$_{30}$H$_{34}$O$_4$: C, 78.57; H, 7.47. Found: C, 78.79; H, 7.07.

Example 5: General Procedure for the Esterification of Acids

The synthesis of 2-methoxy-3'-carboethoxy-[1,1'-biphenyl]-6-carboxylic acid, ethyl ester (6a) is illustrative:

Acid 5a (0.583 g., 1.90 mmol, 1 equiv.) is dissolved in 12 mL of absolute EtOH. Concentrated HCl (0.6 mL) is added, and the mixture heated to reflux for 24 hours. The mixture is then partitioned between EtOAc and water. The organic phase is washed with brine, dried (MgSO$_4$), and concentrated in vacuo. Chromatography on silica gel using 5%, then 10% EtOAc/hexane yields 2-methoxy-3'-carboethoxy-[1,1'-biphenyl]-6-carboxylic acid, ethyl ester (6a) (0.432 g., 1.32 mmol, 73%) as a clear oil: UV$_{max}$ (CHCl$_3$) 242 nm ($\epsilon$=12036), 296 nm ($\epsilon$=4724); $^1$H NMR (300 MHz, CDCl$_3$) δ 8.01 (m, 1H, ArH), 7.92 (m, 1H, ArH), 7.47-7.40 (m, 3H, ArH), 7.39 (dd, J=8, 8 Hz, 1H, ArH), 7.09 (dd, J=2, 8 Hz, 1H, ArH), 4.34 (q, J=7 Hz, 2H, CO$_2$CH$_2$), 3.98 (q, J=7 Hz, 2H, CO$_2$CH$_2$), 3.73 (s, 3H, OCH$_3$), 1.35 (t, J=7 Hz, 3H, CH$_2$CH$_3$), 0.91 (t, J=7 Hz, 3H, CH$_2$CH$_3$); $^{13}$C NMR (75 MHz, CDCl$_3$) δ 168.04 (C=O), 166.65 (C=O), 156.92, 137.28, 134.11, 133.22, 130.73, 130.07, 129.98, 128.78, 128.22, 127.63, 121.63, 113.87, 60.88, 56.02, 14.34, 13.65; IR (film) 2982, 1718, 1466, 1366, 1298, 1260, 1234, 1110, 1060 cm$^{-1}$; MS (DCI) m/e 329 (MH$^+$), 283 (M—C$_2$H$_5$O). Anal. Calcd for C$_{19}$H$_{20}$O$_5$: C, 69.50; H, 6.14. Found: C, 69.44; H, 6.19.

Example 6: General Procedure for the Demethylation of Aryl Methyl Ethers

The synthesis of 2-hydroxy-3'-carboethoxy-(1,1'-biphenyl)-6-carboxylic acid, ethyl ester (7a) is illustrative:

Diester 6a (0.968 g., 2.95 mmol, 1 equiv.) is dissolved under argon in 9.8 mL of 1,2-dichloroethane. Dimethylboron bromide (1.16 mL, 11.9 mmol, 4.03 equiv. ) is added, the flask is sealed and the mixture allowed to stir for 21 hours at ambient temperature. Another 1.16 mL of dimethylboron bromide is added, and the mixture stirred, sealed under argon, for 3 days. The flask is cooled to 0° C., and 20 mL of saturated NaHCO$_3$ is added with caution. The mixture is poured into 1N HCl, and extracted thrice with EtOAc. The combined extracts are washed with brine, dried (MgSO$_4$), and evaporated. Chromatography using 10% EtOAc/hexane yields 2-hydroxy-3'-carboethoxy-(1,1'-biphenyl)-6-carboxylic acid, ethyl ester (7a) (0.659 g., 2.10 mmol, 71%) as a yellow oil: UV$_{max}$ (CHCl$_3$) 242 nm ($\epsilon$=10155), 296 nm ($\epsilon$=4591); $^1$H NMR (300 MHz, CDCl$_3$) δ 8.09 (dd, J=2, 8 Hz, 1H, ArH), 7.96 (dd, J=2, 2 Hz, 1H, ArH), 7.57-7.45 (m, 3H, ArH), 7.33 (dd, J=8, 8 Hz, 1H, ArH), 7.14 (dd, J=2, 8 Hz, 1H, ArH), 4.98 (br, 1H, OH), 4.35 (q, J=7 Hz, 2H, CO$_2$CH$_2$), 3.99 (q, J=7 Hz, 2H, CO$_2$CH$_2$), 1.36 (t, J=7 Hz, 3H, CH$_2$CH$_3$), 0.95 (t, J=7 Hz, 3H, CH$_2$CH$_3$); $^{13}$C NMR (75 MHz, CDCl$_3$) δ 167.18 (C=O), 166.13 (C=O), 153.18, 135.46, 134.13, 131.76, 131.25, 130.67, 129.42, 129.16, 129.03, 127.32, 122.42, 119.19, 61.21, 60.85, 14.30, 13.70; IR (film) 3406, 2982, 1718, 1296, 1236, 758 cm$^{-1}$; MS (DCI) m/e 315 (MH$^+$), 269 (M—C$_2$H$_5$O). HRMS Calcd for C$_{18}$H$_{18}$O$_5$Na: 337.1052. Found: 337.1044.

For 2-hydroxy-3'-carboethoxy-[1,1'-biphenyl]-6-carboxaldehyde (15a): From aldehyde 4a; scale=70.0 mmol, yield=75%; chromatographed on silica gel using EtOAc/CH$_2$Cl$_2$; mp=185°-192° C.; UV$_{max}$ (EtOH) 222 nm ($\epsilon$=22861), 328 nm ($\epsilon$=2822); $^1$H NMR (300 MHz, CDCl$_3$) δ 9.72 (s, 1H, CHO), 8.20 (dd, J=2, 8 Hz, 1H, ArH), 8.06 (d, J=2 Hz, 1H, ArH), 7.67-7.25 (m, 5H, ArH), 5.04 (s, 1H, OH), 4.41 (q, J=7 Hz, 2H, CO$_2$CH$_2$), 1.38 (t, J=7 Hz, 3H, CO$_2$CH$_2$CH$_3$); $^{13}$C NMR (75 MHz, CDCl$_3$) δ 191.43 (C=O), 165.86 (C=O), 153.24, 135.06, 134.89, 132.15, 131.62, 130.01, 129.58, 129.42, 121.25, 120.57, 61.45, 14.29; IR (KBr) 3200, 1720, 1670, 1580, 1290, 1240 cm$^{-1}$; MS (DCI) m/e 271 (MH$^+$), 253, 225.

For 2-hydroxy-[1,1'-biphenyl]-6-carboxaldehyde (15b): From aldehyde 4b; scale=4.71 mmol, yield=70%; chromatographed on silica gel using CH$_2$Cl$_2$/hexane, then CH$_2$Cl$_2$, then 2% MeOH/CH$_2$Cl$_2$; mp=134°-136° C.; UV$_{max}$(EtOH) 224 nm ($\epsilon$=21634), 208 nm ($\epsilon$=20800), 260 nm ($\epsilon$=7267), 328 nm ($\epsilon$=4156); $^1$H NMR (300 MHz, CDCl$_3$) δ 9.77 (s, 1H, CHO), 7.66 (d, J=8 Hz, 1H, ArH), 7.45-7.34 (m, 6H, ArH), 7.19 (d, J=8 Hz, 1H, ArH); $^{13}$C NMR (75 MHz, CDCl$_3$) δ 192.04 (C=O), 153.25, 134.76, 131.44, 131.25, 130.80, 129.43, 129.21, 129.14, 121.04, 119.83; IR (KBr) 3200, 1660, 1600, 1580, 1280, 1220 cm$^{-1}$; MS (DCI) m/e 199 (MH$^+$), 181 (M—OH). Anal. Calcd for C$_{13}$H$_{10}$O$_2$: C, 78.77; H, 5.08. Found: C, 78.48; H, 5.04.

For 2-hydroxy-3'-trifluoromethyl-[1,1'-biphenyl]-6-carboxaldehyde (15c): From aldehyde 4c; scale=2.0 mmol, yield=50%; chromatographed on silica gel using CH$_2$Cl$_2$hexane, then CH$_2$Cl$_2$, then 2% MeOH/CH$_2$Cl$_2$; mp=157°-158° C.; UV$_{max}$(EtOH) 226 nm ($\epsilon$=16912), 326 nm ($\frac{2}{3}$=4079); $^1$H NMR (300 MHz, CDCl$_3$) δ 9.60 (s, 1H, CHO), 7.65-7.11 (m, 7H, ArH); $^{13}$C NMR (75 MHz, CDCl$_3$) δ 191.30 (C=O), 153.18, 134.89, 134.18, 133.00, 131.30 (d, J $^2_{c-f}$=19 Hz), 129.82, 129.73, 129.37, 127.50 (d, J $^3_{c-f}$=4 Hz), 125.79 (d, J $^3_{c-f}$=4 Hz), 123.98 (q, J $^1_{c-f}$=278 Hz), 121.42, 120.97; IR (KBr) 3220, 1660, 1580, 1330, 1285, 1110 cm$^{-1}$; MS (DCI) m/e 267 (MH$^+$). Anal. Calcd for C$_{14}$H$_9$F$_3$O$_2$.0.25 H$_2$O: C, 62.22; H, 3.54. Found: C, 62.32; H, 3.30.

Example 7: General Procedure for Hydrolysis of Esters

The synthesis of (E)-[2-(5,6,7,8-tetrahydro-5,5,8,8-tetramethyl-2-naphthalenyl)-1-propenyl]-[1,1'-biphenyl]-6,3'-dicarboxylic acid (11) is representative:

6-Carboethoxy-2-[(E)-2-[(5,5,8,8-tetramethyl-5,6,7,8-tetrahydro)-2-naphthalenyl]-1-propenyl]-3'-carboethoxy-[1,1'-biphenyl](10a) (0.189 g., 0.361 mmol, 1 equiv.) is dissolved in 3.1 mL of MeOH, 3.1 mL of 2N NaOH, and 4 mL of THF. The mixture is heated to reflux for two hours. The solution is allowed to cool to room temperature, and then acidified to pH 2 with 1N HCl. The material is extracted thrice with chloroform, and the extracts are washed with brine, dried (MgSO$_4$), and evaporated. Reverse-phase chromatography on C-18 silica gel with 90% MeOH/H$_2$O as eluent afforded (E)-[2-(5,6,7,8-tetrahydro-5,5,8,8-tetramethyl-2-naphthalenyl)-1-propenyl]-[1,1'-biphenyl]-6,3'-dicarboxylic acid (11) (0.149 g., 0.318 mmol, 88%) as a white solid: UV$_{max}$ (EtOH) 212 nm ($\epsilon$=29622), 276 nm ($\epsilon$=12314); $^1$H NMR (300 MHz, CD$_3$OD) δ 8.02 (ddd, J=2, 2, 8 Hz, 1H, ArH), 7.89 (s, 1H, ArH), 7.79 (d, J=8 Hz, 1H, ArH), 7.59 (d, J=8 Hz, 1H, ArH), 7.49 (m, 2H, ArH), 7.42 (ddd, J=2, 2, 8 Hz, 1H, ArH), 7.18 (d, J=8 Hz, 1H, ArH), 6.95 (m, 2H, ArH ), 6.20 (s, 1H, C=CH), 2.08 (s, 3H, CH$_3$), 1.64 (s, 4H, CH$_2$CH$_2$), 1.22 (s, 6H, 2×CH$_3$), 1.14 (s, 6H, 2×CH$_3$); $^{13}$C NMR (75 MHz, CD$_3$OD) δ 169.78 (C=O), 145.57, 144.93, 141.99, 141.88, 141.78, 139.76, 139.23, 135.11, 133.84, 131.96, 131.50, 129.42, 128.98, 128.36, 127.33, 126.82, 124.90, 124.33, 36.28, 36.18, 35.13, 34.95, 32.25, 32.16, 17.56; IR (KBr) 3510, 2956, 2924, 1694, 1408, 1300, 1250, 758 cm$^{-1}$; MS (DCI) m/e 469 (MH+), 451 (M—OH). Anal. Calcd for $C_{31}H_{32}O_4$: C, 79.46; H, 6.88. Found: C, 79.24; H, 6.99.

For 2-[(3,4-bisdecyloxy)phenyl]methoxy-[1,1'-biphenyl]-6,3'-dicarboxylic acid (14a): From ether 13a; scale=0.43 mmol, yield=54%; recrystallized from CHCl$_3$/pentane; mp=102°-104° C.; UV$_{max}$ (CHCl$_3$) 242 nm ($\epsilon$=19060), 286 nm ($\epsilon$=6543); $^1$H NMR (300 MHz, CDCl$_3$) δ 8.02 (ddd, J=2, 2, 8 Hz, 1H, ArH), 7.90 (dd, J=2, 2 Hz, 1H, ArH), 7.60 (m, 2H, ArH), 7.44 (dd, J=8, 8 Hz, 1H, ArH), 7.38 (dd, J=8, 8 Hz, 1H, ArH), 7.18 (d, J=8 Hz, 1H, ArH), 6.73 (d, J=8 Hz, 1H, ArH), 6.62 (dd, J=2, 8 Hz, 1H, ArH), 6.56 (d, J=2 Hz, 1H, ArH), 4.90 (s, 2H, ArCH$_2$O), 3.91 (t, J=7 Hz, 2H, RCH$_2$O), 3.74 (t, J=7 Hz, 2H, RCH$_2$O), 1.74 (m, 4H, RCH$_2$CH$_2$O), 1.41 (m, 4H, decyl), 1.24 (m, 20H, decyl), 0.85 (m, 6H, 2×CH$_3$); $^{13}$C NMR (75 MHz, CDCl$_3$) δ 173.40 (C=O), 172.29 (C=O), 156.09, 149.23, 148.59, 139.40, 137.23, 135.90, 131.47, 131.37, 130.92, 129.01, 128.98, 128.00, 123.50, 119.01, 117.21, 113.53, 112.05, 70.65, 69.33, 68.97, 31.91, 29.62, 29.47, 29.43, 29.37, 29.28, 26.08, 26.01, 22.69, 14.11; IR (film) 2924, 2854, 1694, 1514, 1468, 1262 cm$^{-1}$; MS (FAB) m/e 683 (MNa+). Anal. Calcd for $C_{41}H_{56}O_7$: C, 74.51; H, 8.54. Found: C, 74.77; H, 8.52.

For 2-[3,4-bis(3-methyl-2-butenyloxy)phenyl]methoxy-[1,1'-biphenyl]-6,3'-dicarboxylic acid (14b): From ether 13b; scale=0.16 mmol, yield=76%; chromatographed on C-18 silica gel using MeOH/water; mp=145° C. (dec.); UV$_{max}$(CHCl$_3$) 242 nm ($\epsilon$=20264), 286 nm ($\epsilon$6689); $^1$H NMR (300 MHz, CDCl$_3$) δ8.02 (ddd, J=2, 2, 8 Hz, 1H, ArH), 7.89 (dd, J=2, 2 Hz, 1H, ArH), 7.59 (m, 2H, ArH), 7.44 (dd, J=8, 8 Hz, 1H, ArH), 7.37 (dd, J=8, 8 Hz, 1H, ArH), 7.18 (dd, J=2, 8 Hz, 1H, ArH), 6.74 (d, J=8 Hz, 1H, ArH), 6.43 (dd, J=2, 8 Hz, 1H, ArH), 6.00 (bs, 1H, ArH), 5.44 (m, 2H, C=CH), 4.91 (s, 2H, ArCH$_2$O), 4.50 (d, J=7 Hz, 2H, C=CHCH$_2$O), 4.34 (d, J=7 Hz, 2H, C=CHCH$_2$O), 1.72 (s, 6H, 2×CH$_3$), 1.66 (s, 3H, CH$_3$), 1.65 (s, 3H, CH$_3$); $^{13}$C NMR (75 MHz, CDCl$_3$) δ 173.41 (C=O), 172.29 (C=O), 156.09, 148.90, 148.32, 137.61, 132.19, 137.09, 134.44, 131.62, 131.42, 130.94, 129.00, 128.92, 128.82, 127.66, 123.06, 120.25, 119.79, 119.09, 117.26, 113.67, 112.24, 70.71, 66.03, 65.70, 25.80, 18.20, 18.17; IR (KBr) 3400, 1690, 1510, 1430, 1300, 1255, 1220, 1130, 1000, 755 cm$^{-1}$; MS (DCI) m/e 517 (MH+), 431 (M-C$_5$H$_9$O). Anal. Calcd for $C_{31}H_{32}O_7$.0.8 H$_2$O: C, 70.14; H, 6.38. Found: C, 70.13; H, 6.17.

For 2-[(3,4-bispentyloxy)phenyl]methoxy-[1,1'-biphenyl]-6,3'-dicarboxylic acid (14c): From ether 13c; scale=0.20 mmol, yield=57%; recrystallized from CH$_2$Cl$_2$/pentane; mp=202°-203° (dec.); UV$_{max}$ (EtOH) 208 nm ($\epsilon$=35722), 284 nm ($\epsilon$=5099); $^1$H NMR (300 MHz, CDCl$_3$) δ 8.01 (d, J=8 Hz, 1H, ArH), 7.90 (s, 1H, ArH), 7.59 (m, 2H, ArH), 7.43 (dd, J=8, 8 Hz, 1H, ArH), 7.37 (dd, J=8, 8 Hz, 1H, ArH), 7.17 (d, J=8 Hz, 1H, ArH), 6.73 (d, J=8 Hz, 1H, ArH), 6.62 (dd, J=2, 8 Hz, 1H, ArH), 6.56 (d, J=2 Hz, 1H, ArH), 4.90 (s, 2H, ArCH$_2$O), 3.91 (t, J=7 Hz, 2H, RCH$_2$O), 3.74 (t, J=7 Hz, 2H, RCH$_2$O), 1.74 (m, 4H, RCH$_2$CH$_2$O), 1.48-1.28 (m, 8H, pentyl), 0.89 (m, 6H, 2×CH$_3$); $^{13}$C NMR (75 MHz, CDCl$_3$) δ 173.47 (C=O), 172.40 (C=O), 156.20, 149.35, 148.70, 137.35, 135.55, 131.77, 131.07, 129.14, 128.93, 127.76, 123.15, 119.16, 117.33, 113.63, 112.17, 70.77, 69.42, 69.08, 29.07, 29.03, 28.35, 28.30, 22.58, 14.15; IR (KBr) 3400, 2956, 2932, 2870, 1692, 1516, 1468, 1432, 1302, 1262, 1170, 1136, 1108, 1080, 758, 694 cm$^{-1}$; MS (DCI) m/e 521 (MH+), 503 (M—OH). Anal. Calcd for $C_{31}H_{36}O_7$.0.4 H$_2$O: C, 70.54; H, 7.03. Found: C, 70.52; H, 6.86.

For 2-[(3,4-biscyclopentyloxy) phenyl]methoxy-[1,1'biphenyl]-6,3'-dicarboxylic acid (14d): From ether 13d; scale=0.31 mmol, yield=48%; recrystallized from CH$_2$Cl$_2$/pentane; mp=178°-180° C.; UV$_{max}$ (CHCl$_3$) 242 nm ($\epsilon$=48261), 284 nm ($\epsilon$16536); $^1$H NMR (300 MHz, CDCl$_3$) δ 8.01 (ddd, J=2, 2, 8 Hz, 1H, ArH), 7.90 (dd, J=2, 2 Hz, 1H, ArH), 7.59 (m, 2H, ArH), 7.44 (dd, J=8, 8 Hz, 1H, ArH), 7.38 (dd, J=8, 8 Hz, 1H, ArH), 7.18 (d, J=8 Hz, 1H, ArH), 6.74 (d, J=8 Hz, 1H, ArH), 6.63 (dd, J=2, 8 Hz, 1H, ArH), 6.58 (d, J=2 Hz, 1H, ArH), 4.90 (s, 2H, ArCH$_2$O), 4.66 (m, 1H, R$_2$CHOR), 4.50 (m, 1H, R$_2$CHOR), 1.80-1.50 (m, 16H, cycloalkyl); $^{13}$C NMR (75 MHz, CDCl$_3$) δ173.37 (C=O), 172.25 (C=O), 156.08, 148.96, 148.45, 137.20, 135.46, 131.48, 131.44, 130.94, 129.18, 128.98, 128.87, 126.68, 122.95, 119.37, 117.13, 116.52, 115.18, 81.12, 80.86, 70.62, 32.76, 32.71, 23.89, 23.84; IR (KBr) 3422, 2962, 2872, 1690, 1508, 1304, 1262 cm$^{-1}$; MS (DCI) m/e 517 (MH+), 499 (M—OH). Anal. Calcd for $C_{31}H_{32}O_7$: C, 72.08; H, 6.24. Found: C, 71.99; H, 6.23.

For 2-[(3-hydroxy-4-pentyloxy)phenyl]methoxy-[1,1'-biphenyl]-6-carboxylic acid (14e): From acid 14f (see Example 4); scale=0.50 mmol, yield=52%; triturated with ether/hexane; mp=96°-97° C.; UV$_{max}$ (EtOH) 208 nm ($\epsilon$=41870), 286 nm ($\epsilon$5608); $^1$H NMR (300 MHz, CDCl$_3$) δ 7.54 (d, J=8 Hz, 1H, ArH), 7.43-7.30 (m, 6H, ArH), 7.14 (d, J=8 Hz, 1H, ArH), 6.75 (s, 1H, ArH), 6.72 (d, J=8 Hz, 1H, ArH), 6.61 (dd, J=2, 8 Hz, 1H, ArH), 4.92 (s, 2H, ArCH$_2$O), 3.40 (t, 2H, OCH$_2$R), 1.80-0.91 (m, 9H, pentyl); $^{13}$C NMR (75 MHz, CDCl$_3$) δ 172.22 (C=O), 156.06, 145.67, 145.45, 136.37, 132.69, 131.64, 129.75, 129.57, 128.26, 127.71, 127.16, 122.68, 118.45, 117.27, 113.10, 111.33, 70.53, 68.96, 28.89, 28.13, 22.42, 14.00; IR (KBr) 3527 (OH), 2930, 2955 1690 (C=O), 1510, 1450, 1270, 1230 cm$^{-1}$; MS (DCI) m/e 406 (M+), 389 (M—OH). Anal. Calcd for $C_{25}H_{26}O_5$: C, 73.69; H, 6.68. Found: C, 73.54; H, 6.41.

For 2-[4-(1-adamantyl)-3-methoxyphenyl]methoxy-[1,1,-biphenyl]-6,3'-dicarboxylic acid (14h): From ether 13h; scale=0.55 mmol, yield=51%; recrystallized from ether/CH$_2$Cl$_2$; mp=245°-250° C.; UV$_{max}$ (EtOH) 206 nm $\epsilon$=49943), 282 nm ($\epsilon$=5808); $^1$H NMR (300 MHz, CDCl$_3$) δ 7.53 (d, J=8 Hz, 1H, ArH), 7.38-7.27 (m, 5H, ArH), 7.16 (d, J=8 Hz, 1H, ArH), 7.07 (d, J=8 Hz, 1H, ArH), 6.67 (d, J=8 Hz, 1H, ArH), 6.58 (s, 1H, ArH), 4.96 (s, 2H, ArCH$_2$O), 3.91 (s, 3H, CH$_3$O), 2.02 (s, 9H, adamantyl), 1.73 (s, 6H, adamantyl); $^{13}$C NMR (75 MHz, CDCl$_3$) 67 158.90 (C=O), 156.15 (C=O), 137.79, 136.58, 135.34, 132.61, 129.58, 128.41, 127.71, 127.07, 126.30, 122.66, 118.11, 116.77, 109.64, 70.28, 54.95, 40.51, 37.09, 36.70, 29.04; IR (KBr) 3420 (OH), 2905, 1690 (C=O), 1585, 1410, 1268 cm$^{-1}$; MS (DCI) m/e 513 (MH+), 512 (M+), 495 (M—OH), 255. Anal. Calcd for $C_{32}H_{32}O_6$: C, 72.44; H, 6.45. Found: C, 72.74; H, 6.27.

For 2-(5,6,7,8-tetrahydro-5,5,8,8-tetramethyl-2-naphthalenyl)methoxy-[1,1'-biphenyl]-6,3'-dicarboxylic acid (14m): From acid 142; scale=0.212 mmol, yield=74%; chromatographed on C-18 silica gel using MeOH/water, then recrystallized from CHCl$_3$/ pentane; mp=239°-242° C.; UV$_{max}$ (EtOH) 214 nm ($\epsilon$=44121), 290 nm ($\epsilon$=3263); $^1$H NMR (300 MHz, CD$_3$OD) δ 7.98 (ddd, J=2, 2, 8 Hz, 1H, ArH), 7.96 (dd, J=2, 2 Hz, 1H, ArH), 7.49-7.38 (m, 4H, ArH), 7.31 (dd, J=2, 8 Hz, 1H, ArH), 7.18 (d, J=8 Hz, 1H, ArH), 7.04 (d, J=2 Hz, 1H, ArH), 6.92 (dd, J=2, 8 Hz, 1H, ArH), 4.98 (s, 2H, ArCH$_2$O), 1.63 (s, 4H, CH$_2$CH$_2$), 1.21 (s, 6H, 2×CH$_3$), 1.11 (s, 6H, 2×CH$_3$); $^{13}$C NMR (75 MHz, CD$_3$OD) δ 171.48 (C=O), 169.98 (C=O), 157.45, 145.88, 145.17, 139.00, 135.59, 135.09, 132.35, 131.96, 131.34, 129.92, 129.34, 128.77, 127.45, 125.83, 125.15, 122.77, 117.09, 71.49, 36.20, 36.17, 35.12, 34.98, 32.24; IR (KBr) 3422, 2956, 2922, 1690, 1598, 1576, 1452, 1412, 1312, 1284, 1262, 1064 cm$^{-1}$; MS (DCI) m/e 459 (MH+), 441 (M—OH), 201 (C$_{15}$H$_{21}$+). Anal. Calcd for C$_{29}$H$_{30}$O$_5$·0.75 H$_2$O: C, 73.78; H, 6.72. Found: C, 73.65; H, 6.42.

Example 8: General Procedure for the Synthesis of Alcohols 12a-d

A. General Procedure for the Synthesis of Dialkoxybenzaldehydes

The synthesis of 3,4-didecyloxybenzaldehyde is illustrative:

3,4-Dihydroxybenzaldehyde (10 g., 72.4 mmol, 1 equiv.) is dissolved in 150 mL of acetone. 1-Bromodecane (45.1 mL, 0.217 mol, 3 equiv.) is added, followed by K$_2$CO$_3$ (10 g., 72.4 mmol, 1 equiv.), and the mixture heated to reflux for 24 hrs. At this time the reaction was incomplete, and another 10 grams of K$_2$CO$_3$ was added and heating continued for 24 hours. The mixture is allowed to cool to room temperature, and is partitioned between ether and water. The aqueous layer is extracted thrice with ether, and the combined organic phases are washed with brine, dried (MgSO$_4$), and evaporated. Upon evaporation, tan crystals formed, and these were collected. Further evaporation yielded another crop of crystals. A total of 16 grams of 3,4-didecyloxybenzaldehyde (38.3 mmol, 53%) was obtained (for an alternative synthesis of this compound see Strzelecka, H.; et al. *Mol. Cryst. Liq. Cryst.* 1988, 156 (Part A), 347): mp=59.5°-60.5° C.; UV$_{max}$ (EtOH) 232 nm (ε=15472), 276 nm (ε=11079), 206 nm (ε=9806), 310 nm (ε=9273); $^1$H NMR (300 MHz, CDCl$_3$) δ 9.81 (s, 1H, CHO), 7.39 (dd, J=2, 8 Hz, 1H, ArH), 7.37 (d, J=2 Hz, 1H, ArH), 6.93 (d, J=8 Hz, 1H, ArH), 4.04 (m, 4H, RCH$_2$O), 1.83 (m, 4H, RCH$_2$CH$_2$O), 1.46 (m, 4H, decyl), 1.25 (m, 24H, decyl), 0.86 (m, 6H, 2×CH$_3$); $^{13}$C NMR (75 MHz, CDCl$_3$) δ 190.98 (C=O), 154.68, 149.44, 129.87, 126.57, 111.76, 110.97, 69.13, 31.90, 29.57, 29.34, 29.07, 28.98, 25.97, 25.94, 22.68, 14.10; IR (KBr) 2956, 2922, 2850, 1688, 1674, 1596, 1586, 1510, 1278, 1134, 808 cm$^{-1}$; MS (DCI) m/e 419 (MH+). Anal. Calcd for C$_{27}$H$_{46}$O$_3$: C, 77.46; H, 11.07. Found: C, 77.19; H, 10.99.

For 3,4-bis (3-methyl-2-butenyloxy)benzaldehyde: scale=6.75 mmol, yield=80%; chromatographed using EtOAc/hexane; UV$_{max}$ (CHCl$_3$) 280 nm (ε=11088), 312 nm (ε=9626), 240 nm (ε=7701); $^1$H NMR (300 MHz, CDCl$_3$) δ 9.80 (s, 1H, CHO), 7.38 (m, 2H, ArH), 6.93 (m, 1H, ArH), 5.47 (m, 2H, C=CH), 4.65 (d, J=6 Hz, 2H, RCH$_2$O), 4.61 (d, J=6 Hz, 2H, RCH$_2$O), 1.75 (s, 6H, 2×CH$_3$), 1.72 (s, 6H, 2×CH$_3$); $^{13}$C NMR (75 MHz, CDCl$_3$) δ 190.97 (C=O), 154.32, 149.11, 138.04, 137.98, 129.83, 126.51, 119.43, 119.28, 112.04, 111.11, 66.02, 65.93, 25.82, 25.79, 18.32, 18.29; IR (film) 2976, 2932, 2916, 1684, 1584, 1506, 1436, 1260, 1230, 1132, 1004 cm$^{-1}$; MS (DCI) m/e 275 (MH+). Anal. Calcd for C$_{17}$H$_{22}$O$_3$: C, 74.42; H, 8.08. Found: C, 74.41; H, 8.16.

For 3,4-bis (pentyloxy)benzaldehyde: scale=108.6 mmol, yield=100%; crystals from evaporation of ether extracts; mp=31°-32.5° C.; UV$_{max}$ (EtOH) 232 nm (ε=15569), 276 nm (ε=10907), 208 nm (ε=10783), 310 nm (ε=9079); $^1$H NMR (300 MHz, CDCl$_3$) δ 9.79 (s, 1H, CHO), 7.38 (dd, J=2, 8 Hz, 1H, ArH), 7.36 (d, J=2 Hz, 1H, ArH), 6.92 (d, J=8 Hz, 1H, ArH), 4.04 (t, J=7 Hz, 2H, RCH$_2$O), 4.02 (t, J=7 Hz, 2H, RCH$_2$O), 1.83 (m, 4H, RCH$_2$CH$_2$O), 1.43 (m, 8H, pentyl), 0.90 (t, 6H, 2×CH$_3$); $^{13}$C NMR (75 MHz, CDCl$_3$) δ 190.99 (C=O), 154.65, 149.40, 129.84, 126.61, 111.68, 110.84, 69.08, 28.74, 28.65, 28.16, 28.12, 22.42, 14.02; IR (film) 2956, 2934, 2858, 1688, 1674, 1596, 1586, 1510, 1466, 1438, 1274, 1238, 1134, 808 cm$^{-1}$; MS (DCI) m/e 279 (MH+). Anal. Calcd for C$_{17}$H$_{26}$O$_3$: C, 73.35; H, 9.41. Found: C, 73.61; H, 9.40.

For 3,4-bis (cyclopentyloxy) benzaldehyde: scale=17.6 mmol, yield=81%; chromatographed using EtOAc/hexane; UV$_{max}$ (CHCl$_3$) 280 nm (ε11301), 242 nm (ε9509), 312 nm (ε=9089); $^1$H NMR (300 MHz, CDCl$_3$) δ 9.79 (s, 1H, CHO), 7.38 (dd, J=2, 8 Hz, 1H, ArH), 7.36 (d, J=2 Hz, 1H, ArH), 6.92 (dd, J=2, 8 Hz, 1H, ArH), 4.80 (m, 2H, R$_2$CHOR), 1.90-1.77 (m, 12H, cycloalkyl), 1.63-1.56 (m, 4H, cycloalkyl); $^{13}$C NMR (75 MHz, CDCl$_3$) δ 191.02 (C=O), 154.73, 148.95, 129.71, 126.29, 114.24, 113.99, 81.06, 80.79, 32.86, 32.72, 24.01, 23.88; IR (film) 2962, 2872, 1690, 1594, 1580, 1504, 1434, 1264, 1236, 1160, 1130, 984, 868 cm$^{-1}$; MS (DCI) m/e 275 (MH+). Anal. Calcd for C$_{17}$H$_{22}$O$_3$: C, 74.42; H, 8.08. Found: C, 74.48; H, 8.12.

B. General Procedure for Reduction of Benzaldehydes 3,4-Didecyloxybenzaldehyde (6.78 g., 16.2 mmol, 1 equiv.) is dissolved in 44 mL of methanol and 20 mL of THF. Sodium borohydride (0.613 g., 16.2 mmol, 1 equiv.) is added in portions. The mixture is stirred for 30 minutes at room temperature. The solution is poured into saturated ammonium chloride solution, and then extracted twice with EtOAc. The organic extracts are washed with brine, dried (MgSO$_4$), and evaporated. Chromatography on silica gel using 10%-20% EtOAc/hexane affords 3,4-didecyloxybenzyl alcohol (12a) (5.71 g., 13.6 mmol, 84%) as a clear oil: mp=41°-42.5° C.; UV$_{max}$ (EtOH) 206 nm (ε=19085), 232 nm (ε=5340), 280 nm (ε=2239); $^1$H NMR (300 MHz, CDCl$_3$) δ 6.90 (s, 1H, ArH), 6.83 (s, 1H, ArH), 6.83 (s, 1H, ArH), 4.58 (d, J=6 Hz, 2H, ArCH$_2$OH), 3.96 (m, 4H, RCH$_2$O), 1.79 (m, 4H, RCH$_2$CH$_2$O), 1.58 (t, J=6 Hz, 1H, OH), 1.44 (m, 4H, decyl), 1.25 (m, 24H, decyl), 0.86 (m, 6H, 2×CH$_3$); $^{13}$C NMR (75 MHz, CDCl$_3$) δ 149.34, 148.72, 133.68, 119.58, 113.83, 112.95, 69.42, 69.21, 65.41, 31.92, 29.64, 29.59, 29.43, 29.36, 29.30, 26.04, 22.69, 14.12; IR (KBr) 3346, 2956, 2922, 2850, 1520, 1468, 1262, 1236, 1138 m$^{-1}$; MS (DCI) m/e 421 (MH+), 403 (M—OH). Anal. Calcd for C$_{27}$H$_{48}$O$_3$: C, 77.09; H, 11.50. Found: C, 77.26; H, 11.61.

For 3,4-bis(3-methyl-2-butenyloxy)benzyl alcohol (12b): scale=5.47 mmol, yield=84%; chromatographed using EtOAc/hexane; UV$_{max}$ (CHCl$_3$) 242 nm (ε=7198), 282 nm (ε=2881); $^1$H NMR (300 MHz, CDCl$_3$) δ 6.93 (s, 1H, ArH), 6.85 (s, 1H, ArH), 6.85 (s, 1H, ArH), 5.50 (m, 2H, C=CH), 4.59 (d, J=6 Hz, 2H, RCH$_2$O), 4.58 (s, 2H, ArCH$_2$O), 4.57 (d, J=6 Hz, 2H, RCH$_2$O), 1.76 (s, 6H, 2×CH$_3$), 1.72 (s, 6H, 2×CH$_3$); $^{13}$C NMR (75 MHz, CDCl$_3$) δ 149.03, 148.39, 137.25, 137.12, 133.68, 120.30, 120.16, 119.55, 113.94, 113.03, 66.11, 65.94, 65.38, 25.80, 18.23; IR (film) 3406, 2974, 2916, 2870, 1606, 1590, 1512, 1428, 1384, 1256, 1226, 1134, 1004 cm$^{-1}$; MS (DCI) m/e 276 (MH+), 259 (M—OH). Anal. Calcd for C$_{17}$H$_{24}$O$_3$: C, 73.88; H, 8.75. Found: C, 73.50; H, 8.81.

For 3,4-bis (pentyloxy)benzyl alcohol (12c): scale=16.1 mmol, yield=87%; chromatographed using EtOAc/hexane; UV$_{max}$ (EtOH) 206 nm (ε=18552), 230 nm (ε =6802), 280 nm (ε=1983); $^1$H NMR (300 MHz, CDCl$_3$) δ 6.88 (s, 1H, ArH), 6.82 (s, 1H, ArH), 6.82 (s, 1H, ArH), 4.56 (d, J=3 Hz, 2H, ArCH$_2$O), 3.97 (t, J=7 Hz, 2H, RCH$_2$O), 3.96 (t, J=7 Hz, 2H, RCH$_2$O), 1.78 (m, 4H, RCH$_2$CH$_2$O), 1.40 (m, 8H, pentyl), 0.91 (t, J=7 Hz, 6H, 2×CH$_3$); $^{13}$C NMR (75 MHz, CDCl$_3$) δ 149.31, 148.68, 133.75, 119.56, 113.82, 112.94, 69.40, 69.19, 65.32, 28.99, 28.21, 22.48, 14.05; IR (film) 3354, 2956, 2934, 2872, 1608, 1590, 1514, 1468, 1428, 1264, 1234, 1136, 1026, 806 cm$^{-1}$; MS (DCI) m/e 281 (MH+), 263 (M—OH). Anal. Calcd for C$_{17}$H$_{28}$O$_3$: C, 72.82; H, 10.06. Found: C, 72.79; H, 10.06.

For 3,4-bis(cyclopentyloxy)benzyl alcohol (12d): scale=15.0 mmol, yield=91%; chromatographed using EtOAc/hexane; $^1$H NMR (300 MHz, CDCl$_3$) δ 6.89 (s, 1H, ArH), 6.84 (d, J=7 Hz, 1H, ArH), 6.81 (d, J=7 Hz, 1H, ArH), 4.72 (m, 2H, 2×R$_2$CHOR), 4.56 (s, 2H, ArCH$_2$O), 1.88–1.51 (m, 16H, cyclopentyl); $^{13}$C NMR (75 MHz, CDCl$_3$) δ 149.08, 148.50, 133.98, 119.89, 116.92, 115.98, 81.22, 81.10, 65.31, 32.81, 32.77, 23.85; MS (DCI) m/e 277 (MH+), 259 (M-OH). Anal. Calcd for C$_{17}$H$_{24}$O$_3$: C, 73.88; H, 8.75. Found: C, 73.78; H, 8.75.

Example 9: Procedure for the Synthesis of Alcohol 12f 3,4-Dihydroxybenzaldehyde (5 g., 36.2 mmol, 1 equiv.) is dissolved in 80 mL of acetone. n-Pentybromide (4.49 mL, 36.2 mmol, 1 equiv.) is added, followed by anhydrous potassium carbonate (5 g., 36.2 mmol, 1 equiv.). The mixture is stirred at room temperature for 3 days, and then poured into half-saturated ammonium chloride solution. The mixture is extracted thrice with ether, and the extracts are washed with brine, dried (MgSO$_4$), and evaporated. Chromatography on silica gel using EtOAc/hexane affords 3-hydroxy-4-pentyloxy-benzaldehyde (0.820 g., 3.94 mmol, 11%): mp=55°–56° C.; UV$_{max}$ (EtOH) 208 nm (ε=24443), 232 nm (ε=23049), 272 nm (ε=16105), 312 nm (ε=13140); $^1$H NMR (300 MHz, CDCl$_3$) δ 9.80 (s, 1H, CHO), 7.42–7.24 (m, 2H, ArH), 6.94 (d, J=8 Hz, 1H, ArH), 5.82 (s, 1H, OH), 4.10 (t, J=7 Hz, 2H, OCH$_2$R), 1.88–1.79 (m, 2H, OCH$_2$CH$_2$R), 1.49–1.31 (m, 4H, pentyl), 0.92 (t, J=7 Hz, 3H, RCH$_3$); $^{13}$C NMR (75 MHz, CDCl$_3$) δ 191.06 (C=O), 151.30, 146.16, 130.40, 124.55, 113.99, 110.84, 69.27, 28.67, 28.04, 22.39, 13.97; IR (KBr) 3400, 2950, 1680, 1600, 1580, 1280, 1250 cm$^{-1}$; MS (DCI) m/e 209 (MH+). Anal. Calcd for C$_{12}$H$_{16}$O$_3$: C, 69.23; H, 7.69. Found: C, 69.09; H, 7.65.

3-Hydroxy-4-pentyloxy-benzaldehyde (0.750 g., 3.6 mmol, 1 equiv.) is dissolved in 10 mL of methylene chloride. Diisopropyl ethyl amine (0.840 g., 6.5 mmol, 1.8 equiv.) is then added, and the mixture is cooled to 0° C. Acetyl chloride (0.340 g., 4.32 mmol, 1.2 equiv.) dissolved in 2 mL of methylene chloride is added slowly, and the reaction is stirred at 0° C. for 20 min., followed by stirring 30 min. at room temperature. The mixture is diluted with ether, and washed twice with water, dilute HCl, then brine. The organic phase is dried (MgSO$_4$), and evaporated. Trituration with ether affords 3-acetoxy-4-pentyloxy-benzaldehyde (0.750 g., 3.0 mmol, 83%) as a white solid: UV$_{max}$(EtOH) 232 nm (ε=17514), 276 nm (ε=12951), 208 nm (ε=10508), 314 nm (ε=10472); $^1$H NMR (300 MHz, CDCl$_3$) δ 9.85 (s, 1H, CHO), 7.45–7.40 (m, 2H, ArH), 6.95 (d, J=8 Hz, 1H, ArH), 4.15 (t, J=7 Hz, 2H, OCH$_2$R), 2.03 (s, 3H, CH$_3$CO), 1.90–1.85 (m, 2H, OCH$_2$CH$_2$R), 1.57–1.40 (m, 4H, pentyl), 0.95 (t, J=7 Hz, 3H, RCH$_3$); $^{13}$C NMR (75 MHz, CDCl$_3$) δ 191.07 (C=O), 151.31, 146.17, 130.39, 124.56, 113.99, 110.85, 69.27, 28.67, 28.04, 22.38, 13.96; IR (KBr) 2950, 1750, 1680, 1600, 1580, 1510, 1230, 1250 cm$^{-1}$; MS (DCI) m/e 251 (MH+). Anal. Calcd for C$_{14}$H$_{18}$O$_4$: C, 67.20; H, 7.20. Found: C, 66.92; H, 7.62.

3-Acetoxy-4-pentyloxy-benzaldehyde (0.75 g., 3.0 mmol, 1 equiv.) is dissolved in 15 mL of MeOH, and the mixture cooled to 0° C. Sodium borohydride (0.230 g., 6 mmol., 2 equiv.) is added in portions. After stirring for 30 min., the mixture is neutralized with 1N HCl, and then extracted thrice with ether. The extracts are washed with brine, dried (MgSO$_4$), and evaporated. Chromatography on silica gel using CH$_2$Cl$_2$/hexane affords 3-acetoxy-4-pentyloxy-benzyl alcohol (12f) (0.680 g., 2.70 mmol., 90%): mp=35°–36° C.; $^1$H NMR (300 MHz, CDCl$_3$) δ 7.17 (dd, J=2, 8 Hz, 1H, ArH), 7.05 (d, J=2 Hz, 1H, ArH), 6.92 (d, J=8 Hz, 1H, ArH), 4.85 (s, 1H, OH), 4.60 (s, 2H, ArCH$_2$O), 3.95 (t, J=7 Hz, 2H, OCH$_2$R), 2.30 (s, 3H, CH$_3$CO), 1.75 (m, 2H, OCH$_2$CH$_2$), 1.38 (m, 4H, CH$_2$CH$_2$CH$_3$), 0.90 (t, J=7 Hz, 3H, RCH$_2$CH$_3$).

Example 10: Procedures for the Syntheses of Alcohols 12g and 12k

A. Synthesis of 12 g 4-(1-Adamantyl)-3-methoxybenzaldehyde was obtained via the following three-step procedure.

3-Iodophenol was treated with 1-adamantanol and sulfuric acid in methylene chloride following the general procedure of Shreet et al. U.S. Pat. No. 4,717,720, 1/1988. This gave, without recrystallization, pure 2-adamantyl-5-iodophenol: scale=114 mmol, yield=91%; $^1$H NMR (300 MHz, DMSO-d$_6$) δ 7.08 (d, J=2 Hz, 1 H, ArH), 7.04 (dd, J=2, 8 Hz, 1 H, ArH), 6.80 (d, J=8 Hz, 1 H, ArH), 3.36 (s, 1 H, OH), 1.99 (s, 9 H, adamantyl), and 1.68 (s, 6 H, adamantyl); $^{13}$C NMR (75 MHz, CDCl$_3$) δ 157.26, 135.66, 128.32, 127.54, 124.50, 91.23, 39.61, 36.56, 36.12, and 28.32; IR (KBr) 3480 (OH), 2900, 2845, 1490, 1395, 1210, and 875 cm$^{-1}$; MS (DCI) m/e 355 (MH+), 354 (M+), 353 (M—H)+, 135 (C$_{10}$H$_{15}$+). Anal. Calcd for C$_{16}$H$_{19}$OI: C, 54.25; H, 5.41. Found: C, 54.32; H, 5.37.

A solution of 2-adamantyl-5-iodophenol (7.70 g, 21.7 mmol) in acetone (100 mL) was treated with dimethylsulfate (4.11 g, 32.6 mmol) and potassium carbonate (4.50 g, 32.6 mmol). The reaction mixture was stirred at reflux for 24 h, allowed to cool to room temperature, and concentrated in vacuo. The crude product was partitioned between methylene chloride and water. The organic phase was dried over anhydrous magnesium sulfate, filtered, and concentrated to provide 6.5 g (81%) of 2-adamantyl-5-iodoanisole; $^1$H NMR (300 MHz, CDCl$_3$) δ 7.22 (dd, J=2, 8 Hz, 1H, ArH), 7.10 (d, J=2 Hz, 1H, ArH), 6.89 (d, J=8 Hz, 1H, ArH), 3.79 (s, 3H, OCH$_3$), 2.02 (s, 9H, adamantyl), and 1.73 (s, 6H, adamantyl); $^{13}$C NMR (75 MHz, CDCl$_3$) δ 159.35, 138.43, 129.63, 128.25, 120.75, 91.20, 55.22 (OCH$_3$), 40.35, 37.02, 36.92, and 28.97; MS (DCI) m/e 369 (MH+), 368 (M+), 367 (M—H)+, 135 (C$_{10}$H$_{15}$+). Anal. Calcd for C$_{17}$H$_{21}$OI: C, 55.45; H, 5.75. Found: C, 55.51; H, 5.81.

A solution of 2-adamantyl-5-iodoanisole (1.29 g, 3.51 mmol) in anhydrous THF (50 mL) was cooled to −78° C. under argon and treated with t-butyllithium solution (4.34 mL, 1.7 M in pentane, 7.37 mmol). The reaction mixture was stirred at −78° C. for 20 min. and then treated with anhydrous N,N-dimethylformamide (0.28 g, 3.86 mmol). The reaction mixture was allowed to warm to room temperature, and was poured into a separatory funnel containing diethyl ether and saturated ammonium chloride solution. The layers were agitated and separated, and the organic layer was washed with saturated sodium chloride solution, dried over anhydrous magnesium sulfate, filtered, and concentrated. The crude product was purified by column chromatography on silica gel (elution with 1:1 methylene chloride/hexanes) to afford 0.38 g (43% yield) of 4-(1-Adamantyl)-3-methoxybenzaldehyde as a white solid; $^1$H NMR (300 MHz, CDCl$_3$) δ 9.92 (s, 1H, CHO), 7.37 (m, 3H, ArH), 3.88 (s, 3H, OCH$_3$), 2.08 (s, 9H, adamantyl), and 1.76 (s, 6H, adamantyl); $^{13}$C NMR (75 MHz, CDCl$_3$) δ 192.04 (C=O), 159.38, 146.00, 135.36, 127.06, 124.45, 109.54, 55.09 (OCH$_3$), 40.15, 37.79, 36.95, and 28.90; IR (KBr) 2965, 2900, 2850, 1690 (C=O), 1250, 1160, 1135, 1035, and 1025 cm$^{-1}$; MS (DCI) m/e 271 (MH$^+$), 135 (C$_{10}$H$_{15}^+$). Anal. Calcd for C$_{18}$H$_{22}$O$_2$.0.015 H$_2$O: C, 79.88; H, 8.21. Found: C, 79.48; H, 8.34.

4 -(1-Adamantyl)-3-methoxybenzaldehyde was reduced according to the method of Example 8 to afford 3-methoxy-4-(1-adamantyl)-benzyl alcohol (12 g): scale=1.09 mmol, yield=97%; chromatographed using EtOAc/hexane; mp=120°-121° C.; UV$_{max}$ (EtOH) 204 nm (ε=23629), 228 nm (ε=6346), 274 nm (ε=2540), 280 nm (ε=2502); $^1$H NMR (300 MHz, CDCl$_3$) δ 7.23 (d, J=7 Hz, 1H, ArH), 6.88 (m, 2H, ArH), 4.63 (s, 2H, ArCH$_2$O), 3.83 (s, H, OCH$_3$), 2.08 (s, 9H, adamantyl), 1.77 (s, 6H, adamantyl); $^{13}$C NMR (75 MHz, CDCl$_3$) δ 159.03, 139.62, 138.01, 126.63, 118.87, 110.39, 65.21, 54.98, 40.59, 29.10; IR (KBr) 3400, 2900, 1500, 1410, 1255, 1240, 1040 cm$^{-1}$; MS (DCI) m/e 273 (MH$^+$), 272 (M$^+$), 256 (M—OH). Anal. Calcd for C$_{18}$H$_{24}$O$_2$: C, 79.37; H, 8.88. Found: C, 79.23; H, 8.91.

B. Synthesis of 12k

Commercially available 4-decyloxybenzaldehyde was reduced according to the method of Example 8 to provide 4-decyloxybenzyl alcohol (12k): scale=8.14 mmol, yield=71%; recrystallized from EtOAc/hexane; mp=54°-55° C.; UV$_{max}$ (EtOH) 226 nm (ε=10114), 202 nm (ε=5906), 274 nm (ε=1716); $^1$H NMR (300 MHz, CDCl$_3$) δ 7.28-6.81 (m, 4H, ArH), 4.58 (s, 2H, ArCH$_2$O), 3.93 (t, J=8 Hz, 2H, OCH$_2$R), 1.80-1.25 (m, 16H, decyl), 0.86 (t, J=8 Hz, 3H, CH$_3$); $^{13}$C NMR (75 MHz, CDCl$_3$) δ 158.80, 132.87, 128.62, 114.56, 68.07, 65.10, 31.89, 29.56, 29.40, 29.31, 29.26, 26.03, 22.68, 14.11; IR (KBr) 3330, 3220, 2900, 1610, 1520, 1250, 1100, 1070 cm$^{-1}$; MS (DCI) m/e 265 (MH$^+$), 264 (M$^+$), 247 (M-OH). Anal. Calcd for C$_{17}$H$_{28}$O$_2$: C, 77.27; H, 10.69. Found: C, 77.39; H, 10.72.

Example 11: General Procedure for the Synthesis of Ethers 13a-c,h; 16f-g, i—k

The synthesis of 2-[(3,4-bisdecyloxy)phenyl]methoxy-[1,1'-biphenyl]-6,3'-dicarboxylic acid, diethyl ester (13a) is representative:

2-hydroxy-3' -carboethoxy-(1,1'-biphenyl)-6-carboxylic acid, ethyl ester (7a) (466 mg., 1.48 mmol, 1 equiv.) is dissolved in 7.4 mL of THF. Triphenylphosphine (467 mg., 1.78 mmol, 1.2 equiv.) is added, and the flask is cooled to 0° C. Diisopropylazodicarboxylate (0.35 mL, 1.78 mmol, 1.2 equiv.) is added, followed by the dropwise addition of a solution of 3,4-didecyloxybenzyl alcohol (12a) in 2.9 mL of THF. The mixture is stirred for 1 hr. at 0° C., and poured into water. The aqueous layer is extracted thrice with EtOAc, and the combined extracts washed with brine, dried (MgSO$_4$), and evaporated. Chromatography using 25–50–75% CH$_2$Cl$_2$/hexane yields 2-[(3,4-bisdecyloxy)phenyl]methoxy-[1,1'-biphenyl]-6,3'-dicarboxylic acid, diethyl ester (13a) (0.468 g., 0.654 mmol, 44%) as a clear oil: mp=59.5°-60.5° C.; $^1$H NMR (300 MHz, CDCl$_3$) δ 8.03 (ddd, J=2, 2, 8 Hz, 1H, ArH), 7.99 (d, J=2 Hz, 1H, ArH), 7.50-7.40 (m, 3H, ArH), 7.37 (dd, J=8, 8 Hz, 1H, ArH), 7.17 (d, J=8 Hz, 1H, ArH), 6.77 (d, J=8 Hz, 1H, ArH), 6.67 (dd, J=2, 8 Hz, 1H, ArH), 6.61 (d, J=2 Hz, 1H, ArH), 4.94 (s, 2H, ArCH$_2$O), 4.36 (q, J=7 Hz, 2H, CO$_2$CH$_2$), 4.02 (q, J=7 Hz, 2H, CO$_2$CH$_2$), 3.94 (t, J=7 Hz, 2H, RCH$_2$O), 3.77 (t, J=7 Hz, 2H, RCH$_2$O), 1.78 (m, 4H, RCH$_2$CH$_2$O), 1.43 (m, 4H, decyl), 1.36 (t, J=7 Hz, 3H, CO$_2$CH$_2$CH$_3$), 1.29 (m, 24H, decyl), 0.95 (t, J=7 Hz, 3H, CO$_2$CH$_2$CH$_3$), 0.89 (t, 6H, 2×CH$_3$).

For 2-[3,4-bis(3-methyl-2-butenyloxy)phenyl]methoxy-[1,1'-biphenyl ]-6,3 '-dicarboxylic acid, diethyl ester (13b): From alcohol 12b and phenol 7a; scale=0.434 mmol, yield=68%; chromatographed on silica gel using EtOAc/hexane; mp=85.5°-87.5° C.; UV$_{max}$ (CHCl$_3$) 242 nm (ε=19498), 286 nm (ε=6685); $^1$H NMR (300 MHz, CDCl$_3$) δ 8.00 (ddd, J=2, 2, 8 Hz, 1H, ArH), 7.96 (dd, J=2, 2 Hz, 1H, ArH), 7.49-7.39 (m, 3H, ArH), 7.35 (dd, J=8, 8 Hz, 1H, ArH), 7.13 (dd, J=2, 8 Hz, 1H, ArH), 6.74 (d, J=8 Hz, 1H, ArH), 6.67 (dd, J=2, 8 Hz, 1H, ArH), 6.63 (d, J=2 Hz, 1H, ArH), 5.44 (m, 2H, C=CH), 4.92 (s, 2H, ArCH$_2$O), 4.51 (d, J=6 Hz, 2H, RCH$_2$O), 4.36 (d, J=6 Hz, 2H, RCH$_2$O), 4.32 (q, J=7 Hz, 2H, CO$_2$CH$_2$), 3.98 (q, J=7 Hz, 2H, CO$_2$CH$_2$), 1.73 (s, 6H, 2×CH$_3$), 1.67 (s, 3H, CH$_3$), 1.66 (s, 3H, CH$_3$), 1.34 (t, J=7 Hz, 3H, CO$_2$CH$_2$CH$_3$), 0.91 (t, J=7 Hz, 3H, CO$_2$CH$_2$CH$_3$); $^{13}$C NMR (75 MHz, CDCl$_3$) δ 168.01 (C=O), 166.54 (C=O), 155.98, 148.89, 148.31, 137.52, 137.44, 137.07, 134.18, 133.22, 130.93, 130.78, 129.94, 129.17, 128.71, 128.16, 127.53, 122.15, 120.26, 119.92, 119.14, 116.29, 113.73, 112.40, 70.65, 66.05, 65.72, 60.88, 25.80, 25.77, 18.20, 14.30, 13.66; IR (KBr) 2982, 2930, 1714, 1574, 1512, 1290, 1252, 1232, 1038, 852, 766 cm$^{-1}$; MS (DCI) m/e 573 (MH$^+$). Anal. Calcd for C$_{35}$H$_{40}$O$_7$: C, 73.40; H, 7.04. Found: C, 73.19; H, 7.04.

For 2-[(3,4-bispentyloxy)phenyl]methoxy'[1,1'-biphenyl]-6,3'-dicarboxylic acid, diethyl ester (13c): From alcohol 12c and phenol 74; scale=0.350 mmol, yield=55%; chromatographed on silica gel using EtOAc/hexane; $^1$H NMR (300 MHz, CDCl$_3$) δ 8.09 (ddd, J=2, 2, 8 Hz, 1H, ArH), 8.01 (s, 1H, ArH), 7.51-7.40 (m, 3H, ArH), 7.38 (dd, J=8, 8 Hz, 1H, ArH), 7.17 (d, J=8 Hz, 1H, ArH), 6.76 (d, J=8 Hz, 1H, ArH), 6.67 (dd, J=2, 8 Hz, 1H, ArH}, 6.61 (d, J=2 Hz, 1H, ArH), 4.94 (s, 2H, ArCH$_2$O), 4.36 (q, J=7 Hz, 2H, CO$_2$CH$_2$), 4.01 (q, J=7 Hz, 2H, CO$_2$CH$_2$), 3.95 (t, J=7 Hz, 2H, RCH$_2$O), 3.76 (t, J=7 Hz, 2H, RCH$_2$O), 1.79 (m, 4H, RCH$_2$CH$_2$O), 1.40 (m, 8H, pentyl), 1.39 (t, J=7 Hz, 3H, CO$_2$CH$_2$CH$_3$), 0.91 (m, 9H, 2×RCH$_3$ and CO$_2$CH$_2$CH$_3$).

For 2-[(3-acetoxy-4-pentyloxy)phenyl]methoxy-[1,1'-biphenyl]-6-carboxaldehyde (16f): From alcohol 12f and phenol 15b; scale=2.58 mmol, yield=62%; chromatographed on silica gel using CH$_2$Cl$_2$/hexane; UV$_{max}$ (EtOH) 228 nm (ε=31838), 204 nm (ε=21123), 322 nm (ε=3763); $^1$H NMR (300 MHz, CDCl$_3$) δ 9.75 (s, 1H, CHO), 7.63 (dd, J=1, 8 Hz, 1H, ArH), 7.44–7.21 (m, 7H, ArH), 6.98 (dd, J=1, 8 Hz, 1H, ArH), 6.84 (d, J=8 Hz, 1H, ArH), 6.82 (d, J=2 Hz, 1H, ArH), 4.98 (s, 2H, ArCH$_2$O), 3.94 (t, J=6 Hz, 2H, ArOCH$_2$R), 2.83 (s, 3H, CH$_3$CO$_2$), 1.75-1.30 (m, 6H, OCH$_2$(CH$_2$)$_3$CH$_3$), 0.92 (t, J=6 Hz, 3H, CH$_3$); $^{13}$C NMR (75 MHz, CD$_3$OD) δ 171.93 (C=O), 170.61 (C=O), 157.27, 151.34, 141.11, 138.23, 135.26, 132.90, 130.95, 130.81, 129.50, 128.54, 127.86, 126.41, 122.61, 122.55, 117.33, 114.13, 70.89, 69.64, 29.24, 29.26, 23.41, 20.53, 14.42; IR (KBr) 2960, 2870, 1750, 1690, 1510, 1280, 1200 cm$^{-1}$; MS (DCI) m/e 433 (M+) . Anal. Calcd for $C_{27}H_{28}O_5$.0.25 $H_2O$: C, 74.20; H, 6.57. Found: C, 73.87; H, 6.62.

For 2-[4,(1-adamantyl)-3-methoxyphenyl]methoxy-[1,1'-biphenyl]-6-carboxaldehyde (16 g): From alcohol 12g and phenol 15b; scale=10.0 mmol, yield=57%; chromatographed on silica gel using $CH_2Cl_2$/hexane; mp=115°-116° C.; $UV_{max}$(EtOH) 204 nm ($\epsilon$=37108), 226 nm ($\epsilon$=28948); $^1$H NMR (300 MHz, CDCl$_3$) δ 9.75 (s, 1H, CHO), 7.65 (dd, J=1, 8 Hz, 1H, ArH), 7.47-7.34 (m, 6H, ArH), 7.25 (dd, J=1, 8 Hz, 1H, ArH), 7.11 (d, J=8 Hz, 1H, ArH), 6.73 (dd, J=1, 8 Hz, 1H, ArH), 6.63 (s, 1H, ArH), 5.02 (s, 2H, ArCH$_2$O), 3.63 (s, 3H, CH$_3$O), 2.03 (s, 9H, adamantyl), 1.55 (s, 6H, adamantyl); $^{13}$C NMR (75 MHz, CDCl$_3$) δ 192.48 (C=O), 158.96, 156.12, 137.97, 135.74, 135.54, 135.28, 131.16, 128.80, 127.99, 127.86, 126.43, 119.58, 118.23, 118.05, 109.70, 70.36, 54.94, 40.57, 37.13, 36.87, 29.09; IR (KBr) 2905, 2850, 1690 (C=O), 1450, 1267, 1255 cm$^{-1}$; MS (DCI) m/e 452 (MH+), 452 (M+), 451, 435 (M—OH), 255. Anal. Calcd for $C_{31}H_{32}O_3$: C, 82.15; H, 7.17. Found: C, 82.27; H, 7.13.

For 2-[4-(1-adamantyl)-3-methoxyphenyl]methoxy-1,1'-biphenyl]-6,3'-dicarboxylic acid, diethyl ester (13h): From alcohol 12g and phenol 7a; scale=1.16 mmol, yield=62%; chromatographed on silica gel using $CH_2Cl_2$/hexane; $^1$H NMR (300 MHz, CDCl$_3$) δ 8.05 (d, J=8 Hz, 1H, ArH), 8.02 (s, 1H, ArH), 7.49-7.39 (m, 4H, ArH), 7.26 (d, J=8 Hz, 1H, ArH), 7.09 (d, J=8 Hz, 1H, ArH), 6.74 (d, J=8 Hz, 1H, ArH), 6.59 (s, 1H, ArH), 5.00 (s, 2H, ArCH$_2$O), 4.38 (q, J=7 Hz, 2H, CO$_2$CH$_2$), 4.02 (q, J=7 Hz, 2H, CO$_2$CH$_2$), 3.62 (s, 3H, CH$_3$O), 2.04 (s, 9H, adamantyl), 1.75 (s, 6H, adamantyl), 1.40 (t, J=7 Hz, 3H, CO$_2$CH$_2$CH$_3$), 0.97 (t, J=7 Hz, 3H, CO$_2$CH$_2$CH$_3$); $^{13}$C NMR (75 MHz, CDCl$_3$) δ 167.89 (C=O), 166.60 (C=O), 158.89, 156.02, 137.81, 137.64, 135.27, 134.25, 133.16, 130.81, 129.99, 128.85, 127.66, 126.36, 122.12, 118.21, 115.88, 109.57, 70.16, 60.94, 54.86, 40.53, 37.12, 36.82, 29.07, 14.38, 13.71.

For 2-[(3,4-bispentyloxy)phenyl]methoxy-[1,1'-biphenyl]-6-carboxaldehyde (16i): From alcohol 12c and phenol 15b; scale=3.08 mmol, yield=51%; chromatographed on silica gel using $CH_2Cl_2$/hexane; $^1$H NMR (300 MHz, CDCl$_3$) δ 9.78 (s, 1H, CHO), 7.67 (d, J=8 Hz, 1H, ArH), 7.46-7.37 (m, 6H, ArH), 7.27 (d, J=8 Hz, 1H, ArH), 6.81 (d, J=8 Hz, 1H, ArH), 6.79 (d, J=8 Hz, 1H, ArH), 6.70 (s, 1H, ArH), 4.98 (s, 2H, ArCH$_2$O), 3.97 (t, J=7 Hz, 2H, OCH$_2$R), 3.89 (t, J=7 Hz, OCH$_2$R), 1.84-0.92 (m, 18 H, pentyl); $^{13}$C NMR (75 MHz, CDCl$_3$) δ 192.35 (C=O), 156.03, 149.23, 148.57, 135.73, 135.46, 133.36, 131.13, 129.17, 128.71, 127.91, 127.82, 119.54, 119.02, 118.24, 113.46, 112.11, 70.57, 69.28, 68.95, 28.99, 28.28, 28.22, 22.51, 21.59, 14.10.

For 2-[(3,4-bispentyloxy)phenyl]methoxy-[1,1'-biphenyl]-3'-trifluoromethyl-6-carboxaldehyde (16j): From alcohol 12c and phenol 15c; scale=0.85 mmol, yield=52%; chromatographed on silica gel using $CH_2Cl_2$/hexane; $^1$H NMR (300 MHz, CDCl$_3$) δ 9.75 (s, 1H, CHO), 7.67-7.48 (m, 6H, ArH), 7.30 (d, J=8 Hz, 1H, ArH), 6.81 (d, J=8 Hz, 1H, ArH), 6.73 (d, J-8 Hz, 1H, ArH), 6.66 (s, 1H, ArH), 4.99 (s, 2H, ArCH$_2$O), 3.96 (t, J=7 Hz, 2 H, OCH$_2$R), 3.82 (t, J=7 Hz, 2H, OCH$_2$R), 1.83-0.90 (m, 18 H, pentyl); $^{13}$C NMR (75 MHz, CDCl$_3$) δ 191.54 (C=O), 155.91, 149.23, 148.84, 135.30, 134.41, 134.37, 130.02, 129.42 (d, J $^3_{c-f}$=4 Hz), 128.50 (d, J $^2_{c-f}$=19 Hz), 126.30 (q, J $^1_{c-f}$=235 Hz), 125.99, 122.02, 119.93, 119.42, 118.16 (d, J $^3_{c-f}$=4 Hz), 113.50, 112.35, 70.68, 69.26, 69.01, 28.92, 28.22, 28.20, 22.46, 14.05, 14.03.

For 2-[(4-decyloxy)phenyl]methoxy-[1,1'-biphenyl]-6-carboxaldehyde (16k): From alcohol 12k and phenol 15b; scale=2.67 mmol, yield=30%; chromatographed on silica gel using $CH_2Cl_2$/hexane; $UV_{max}$ (EtOH) 228 nm ($\epsilon$=35320), 206 nm ($\epsilon$=30697), 320 nm ($\epsilon$=3743); $^1$H NMR (300 MHz, CDCl$_3$) δ 9.79 (s, 1H, CHO), 7.67 (d, J=8 Hz, 1H, ArH), 7.50-7.38 (m, 6H, ArH), 7.35 (d, J=8 Hz, 1H, ArH), 7.22 (d, J=8 Hz, 2H, ArH), 6.83 (d, J=8 Hz, 2H, ArH), 4.99 (s, 2H, ArCH$_2$O), 3.93 (t, J=7 Hz, 2H, OCH$_2$R), 1.77 (m, 2H, OCH$_2$CH$_2$R), 1.47-1.30 (m, 14H, R(CH$_2$)$_7$CH$_3$), 1.91 (t, J=7 Hz, 3H, CH$_3$); $^{13}$C NMR (75 MHz, CDCl$_3$) δ 192.22 (C=O), 158.81, 156.06, 135.82, 135.52, 133.23, 131.15, 128.60, 128.33, 127.96, 127.88, 127.85, 119.61, 118.42, 114.39, 96.15, 70.66, 67.94, 31.92, 29.60, 29.42, 29.34, 29.28, 26.08, 22.70, 14.16; IR (KBr) 2930, 2840, 1690 (C=O), 1580, 1515, 1470, 1245 cm$^{-1}$; MS (DCI) m/e 445 (MH+), 427 (M-OH), 247. Anal. Calcd for $C_{30}H_{36}O_3$.0.1 $CH_2Cl_2$: C, 79.82; H, 8.00. Found: C, 80.05; H, 7.78.

Example 12: Procedure for the Synthesis of Ether 13d

3-Methoxy-2-hydroxy-benzoic acid, methyl ester was converted via the method of Example 1 to 3-methoxy-2-(trifluoromethane-sulphonyloxy)-benzoic acid, methyl ester: scale=15.2 mmol, yield=59%; chromatographed on silica gel using $CH_2Cl_2$/hexane; $^1$H NMR (300 MHz, CDCl$_3$) δ 7.53 (dd, J=2, 8 Hz, 1H, ArH), 7.35 (dd, J=8, 8 Hz, 1H, ArH), 7.18 (dd, J=2, 8 Hz, 1H, ArH), 3.92 (s, 3H, CH$_3$), 3.89 (s, 3H, CH$_3$); $^{13}$C NMR (75 MHz, CDCl$_3$) δ 164.43 (C=O), 151.72, 137.53, 128.45, 125.59, 123.11, 118.66 (q, J $^2_{c-f}$=319 Hz, CF$_3$), 116.83, 56.36, 52.64; IR (film) 2958, 1732, 1582, 1480, 1462, 1422, 1314, 1286, 1246, 1206, 1164, 1138, 1062, 886, 760 cm$^{-1}$; MS (DCI) m/e 315 (MH+), 283 (M—CH$_3$O).

The above triflate was coupled to stannane 3a via the method of Example 3 to afford 3'-carboethoxy-6-carbomethoxy-2-methoxy-[1,1'-biphenyl]: scale=0.975 mmol, yield=61%; chromatographed on silica gel using EtOAc/hexane; $UV_{max}$ (CHCl$_3$) 242 nm ($\epsilon$=10174), 298 nm ($\epsilon$=4122); $^1$H NMR (300 MHz, CDCl$_3$) δ 8.02 (ddd, J=2, 2, 8 Hz, 1H, ArH), 7.91 (dd, J=2, 2 Hz, 1H, ArH), 7.47-7.36 (m, 4H, ArH), 7.09 (dd, J=2, 8 Hz, 1H, ArH), 4.34 (q, J=7 Hz, 2H, CO$_2$CH$_2$), 3.72 (s, 3H, OCH$_3$), 3.53 (s, 3H, CO$_2$CH$_3$), 1.36 (t, J=7 Hz, 3H, CO$_2$CH$_2$CH$_3$); $^{13}$C NMR (75 MHz, CDCl$_3$) δ 168.27 (C=O), 166.66 (C=O), 156.97, 137.10, 133.99, 132.71, 130.63, 130.31, 130.00, 128.77, 128.27, 127.64, 121.64, 114.03, 60.88, 56.02, 51.94, 14.34; IR (film) 2982, 2952, 1718, 1460, 1432, 1300, 1262, 1236, 1110, 1060 cm$^{-1}$; MS (DCI) m/e 315 (MH+), 283 (M—CH$_3$O), 269 (M-C$_2$H$_5$O). Anal. Calcd for $C_{18}H_{18}O_5$: C, 68.78; H, 5.77. Found: C, 68.46; H, 5.84.

The above aryl methyl ether was demethylated via the procedure of Example 6 to yield 2-(3'-carboethoxyphenyl)-3-carbomethoxyphenol: scale=1.09 mmol, yield=40%; chromatographed on silica gel using EtOAc/hexane; $UV_{max}$ (CHCl$_3$) 242 nm ($\epsilon$=10234), 298 nm ($\epsilon$=4739); $^1$H NMR (300 MHz, CDCl$_3$) δ 8.10 (ddd, J=2, 2, 8 Hz, 1H, ArH), 7.96 (dd, J=2, 2 Hz, 1H, ArH), 7.55 (m, 2H, ArH), 7.46 (ddd, J=2, 2, 8 Hz, 1H, ArH), 7.34 (dd, J=8, 8 Hz, 1H, ArH), 7.15 (dd, J=2, 8 Hz, 1H, ArH), 4.95 (s, 1H, OH), 4.36 (q, J=7 Hz, 2H, CO$_2$CH$_2$), 3.57 (s, 3H, CO$_2$CH$_3$), 1.37 (t, J=7 Hz, 3H, CO$_2$CH$_2$CH$_3$); $^{13}$C NMR (75 MHz, CDCl$_3$) δ 167.00

(C=O), 166.13 (C=O), 153.25, 135.25, 134.08, 131.30, 131.20, 130.51, 129.50, 129.16, 129.07, 127.57, 122.46, 119.37, 61.20, 51.95, 14.30; IR (film) 3406, 2984, 2952, 1716, 1606, 1584, 1462, 1434, 1298, 1238, 1142, 1110, 758 cm$^{-1}$; MS (DCI) m/e 301 (MH+), 269 (M—CH$_3$O), 255 (M—C$_2$H$_5$O). Anal. Calcd for C$_{17}$H$_{16}$O$_5$.0.4 H$_2$O: C, 66.39; H, 5.51. Found: C, 66.58; H, 5.50.

The above phenol is then coupled with alcohol via the process of Example 11 to produce 2-[(3,4-biscyclopentyl-oxy)phenyl]methoxy-[1,1'-biphenyl]-6,3'-dicarboxylic acid, 3'-ethyl ester, 6-methyl ester (13d): scale=0.647 mmol, yield=69%; chromatographed on silica gel using EtOAc/hexane; 1H NMR (300 MHz, CDCl$_3$) δ 8.00 (ddd, J=2, 2, 8 Hz, 1H, ArH), 7.96 (dd, J=2, 2 Hz, 1H, ArH), 7.45 (m, 3H, ArH), 7.35 (dd, J=7, 7 Hz, 1H, ArH), 7.15 (dd, J=2, 8 Hz, 1H, ArH), 6.74 (d, J=8 Hz, 1H, ArH), 6.65 (dd, J=2, 8 Hz, 1H, ArH), 6.60 (d, J=2 Hz, 1H, ArH), 4.91 (s, 2H, ArCH$_2$O), 4.66 (m, 1H, R$_2$CHOR), 4.50 (m, 1H, R$_2$CHOR), 4.33 (q, J=7 Hz, 2H, CO$_2$CH$_2$), 3.54 (s, 3H, CO$_2$CH$_3$), 1.85–1.63 (m, 10H, cycloalkyl), 1.54 (m, 6H, cycloalkyl), 1.36 (t, J=7 Hz, 3H, CO$_2$CH$_2$CH$_3$); $^{13}$C NMR (75 MHz, CDCl$_3$) δ 168.19 (C=O), 166.40 (C=O), 159.04, 148.93, 137.28, 134.12, 132.71, 130.65, 129.94, 129.34, 128.71, 128.18, 127.55, 122.10, 119.32, 116.58, 116.31, 115.24, 81.13, 80.84, 70.54, 60.87, 51.94, 32.76, 32.71, 23.87, 23.83, 14.32; IR (film) 2958, 1720, 1508, 1296, 1262, 1234, 1166, 758 cm$^{-1}$; MS (DCI) m/e 559 (MH+).

Example 13: General Procedure for the Synthesis of Aldehydes 16 1,n–q

The preparation of ether 16 is illustrative:

Sodium hydride (2.54 g., 0.106 mol, 2.5 equiv.; 80% dispersion, unwashed) is suspended in 75 mL of DMSO. A solution of 2,3-dihydroxybenzaldehyde (5.84 g., 42.3 mmol, 1 equiv.) in 30 mL of DMSO is added dropwise with water bath cooling, and the mixture allowed to stir 1 hr. at room temperature. A solution of 2-chloromethyl-5,5,8,8-tetramethyl-5,6,7,8-tetrahydronaphthalene (18a) (10 g., 42.3 mmol, 1 equiv.) is added and the mixture is allowed to stir overnight at room temperature. The mixture is then poured into half-saturated ammonium chloride solution, and extracted with EtOAc. The aqueous phase is saturated with sodium chloride, and then extracted twice with EtOAc. The combined organic phase is washed with brine, dried (MgSO$_4$), and evaporated. Chromatography on silica gel using 50% CH$_2$Cl$_2$/hexane affords 3-(5,5,8,8-tetramethyl-5,6,7,8-tetrahydro-2-naphthalenyl)methoxy-salicylaldehyde (19a) as a yellow oil (6.02 g., 17.8 mmol, 44%) which occasionally crystallizes upon standing: UV$_{max}$(CHCl$_3$) 268 nm (ε=9894), 240 nm (ε=6181), 350 nm (ε=2513); $^1$H NMR (300 MHz, CDCl$_3$) δ 11.01 (s, 1H, OH), 9.91 (s, 1H, CHO), 7.33 (d, J=2 Hz, 1H, ArH), 7.29 (d, J=8 Hz, 1H, ArH), 7.21–7.13 (m, 3H, ArH), 6.90 (dd, J=8, 8 Hz, 1H, ArH), 5.10 (s, 2H, ArCH$_2$O), 1.66 (s, 4H, CH$_2$CH$_2$), 1.25 (s, 12H, 4×CH$_3$); $^{13}$C NMR (75 MHz, CDCl$_3$) δ 196.45 (C=O), 152.31, 147.46, 145.07, 144.86, 133.33, 126.93, 125.90, 125.12, 125.01, 121.06, 120.97, 119.46, 71.78, 35.03, 35.00, 34.26, 34.16, 31.83; IR (film) 2960, 2926, 2860, 1658, 1456, 1388, 1364, 1276, 1252, 1216, 750, 736 cm$^{-1}$; MS (DCI) m/e 339 (MH+), 201 (C$_{15}$H$_{21}$+). Anal. Calcd for C$_{22}$H$_{26}$O$_3$.0.4 H$_2$O: C, 76.45; H, 7.81. Found: C, 76.62; H, 7.62.

Aldehyde 19a is converted via the method of Example 1 to 2-trifluoromethylsulphonyloxy-3-(5,5,8,8-tetramethyl-5,6,7,8-tetrahydro-2-naphthalenyl ) methoxybenzaldehyde (20a): scale=3.13 mmol, yield=47%; chromatographed on silica gel using CH$_2$Cl$_2$/hexane, clear oil; UV$_{max}$ (CHCl$_3$) 250 nm (ε=8852), 314 nm (ε=3184); $^1$H NMR (300 MHz, CDCl3) δ 10.24 (s, 1H, CHO), 7.51 (dd, J=2, 8 Hz, 1H, ArH), 7.40 (dd, J=8, 8 Hz, 1H, ArH), 7.38–7.30 (m, 3H, ArH), 7.16 (dd, J=2, 8 Hz, 1H, ArH), 5.15 (s, 2H, ArCH2O), 1.67 (s, 4H, CH$_2$CH$_2$), 1.27 (s, 6H, 2×CH$_3$), 1.25 (s, 6H, 2×CH$_3$); $^{13}$C NMR (75 MHz, CDCl$_3$) δ 186.68 (C=O), 151.07, 145.41, 145.29, 139.61, 131.81, 129.55, 128.97, 126.90, 125.79, 124.70, 121.09, 120.73, 120.13, 72.00, 35.03, 34.97, 34.31, 34.21, 31.83, 31.71; IR (film) 3028, 2962, 2930, 2866, 1704, 1580, 1478, 1460, 1426, 1282, 1250, 1208, 1140, 880, 782 cm$^{-1}$; MS (DCI) m/e 471 (MH+), 401 (M-CF$_3$), 201 (C$_{15}$H$_{21}$+). Anal. Calcd for C$_{23}$H$_{25}$F$_3$O$_5$S: C, 58.71; H, 5.36. Found: C, 58.49; H, 5.43.

Triflate 20a is then coupled to stannane 3a using the method of Example 2 to afford 2-(5,5,8,8-tetramethyl-5,6,7,8-tetrahydro-2 -naphthalenyl)methoxy-[1,1'-biphenyl]-3'-carboethoxy-6-carboxaldehyde (16 l): scale=2.4 mmol, yield=77%; chromatographed on silica gel using CH$_2$Cl$_2$/hexane; UV$_{max}$ (CHCl$_3$) 242 nm (ε=13370), 322 nm (ε=2203); $^1$H NMR (300 MHz, CDCl$_3$) δ 9.73 (s, 1H, CHO), 8.10 (ddd, J=2, 2, 8 Hz, 1H, ArH), 8.06 (dd, J=2, 2 Hz, 1H, ArH), 7.64 (dd, J=2, 8 Hz, 1H, ArH), 7.53 (m, 2H, ArH), 7.47 (ddd, J=2, 8, 8 Hz, 1H, ArH), 7.27 (dd, J=2, 8 Hz, 1H, ArH), 7.19 (d, J= 8 HZ, 1H, ArH), 7.04 (d, J=2 Hz, 1H, ArH), 6.92 (dd, J=2, 8 Hz, 1H, ArH), 5.00 (s, 2H, ArCH$_2$O) , 4.36 (q, J=7 Hz, 2H, CO$_2$CH$_2$) , 1.62 ( s, 4H, CH$_2$CH$_2$) , 1.36 ( t, J=7 Hz, 3H, CO$_2$CH$_2$CH$_3$), 1.22 (s, 6H, 2×CH$_3$), 1.12 (s, 6H, 2×CH$_3$); $^{13}$C NMR (75 MHz, CDCl$_3$) δ 191.91 (C=O), 166.26 (C=O), 156.18, 144.99, 144.44, 135.36, 135.30, 134.43, 133.74, 133.25, 131.94, 130.40, 129.15, 128.77, 128.13, 126.57, 124.59, 123.79, 119.61, 117.86, 70.57, 61.12, 34.96, 34.18, 34.07, 31.80, 31.70, 14.33; IR (film) 2960, 2928, 2860, 1720, 1692, 1458, 1294, 1260, 1234, 1110, 756 cm$^{-1}$; MS (DCI) m/e 471 (MH+1), 425 (M-C$_2$H$_5$O), 201 (C$_{15}$H$_{21}$+1). HRMS (FAB) Calcd for C$_{31}$H$_{34}$O$_4$Na: 493.2355. Found: 493.2349.

For 2-(5,5,8,8-tetramethyl-5,6,7,8-tetrahydro-2-naphthalenyl)methoxy-[1,1'-biphenyl]-6-carboxaldehyde (16n): From triflate 20a and phenyltributylstannane; scale=1.33 mmol, yield=75%; chromatographed on silica gel using CH$_2$Cl$_2$/hexane; $^1$H NMR (300 MHz, CDCl$_3$) δ 9.75 (s, 1H, CHO), 7.62 (dd, J=2, 8 Hz, 1H, ArH), 7.48–7.34 (m, 6H, ArH), 7.25 (dd, J=2, 8 Hz, 1H, ArH), 7.20 (d, J=8 Hz, 1H, ArH), 7.08 (d, J=2 Hz, 1H, ArH), 6.92 (dd, J=2, 8 Hz, 1H, ArH), 4.99 (s, 2H, ArCH$_2$O) , 1.63 ( s, 4 H, CH$_2$ CH$_2$), 1.23 ( s, 6H, 2×CH$_3$), 1.15 (s, 6H, 2×CH$_3$); $^{13}$C NMR (75 MHz, CDCl$_3$) δ 192.53 (C=O), 156.17, 145.00, 144.36, 135.76, 135.49 , 133.45, 133.27, 131.10, 128.70, 128.00, 127.89, 126.54 , 124.67, 123.80, 119.44, 117.97, 70.60, 35.02, 34.98, 34.23, 34.09, 31.82, 31.74; IR (KBr) 2956, 2916, 2854, 1690, 1452, 1268, 1242, 790 cm$^{31\ 1}$; MS (DCI) m/e 399 (MH+), 201 (C$_{15}$H$_{21}$+).

For 2-(5,5,8,8-tetramethyl-5,6,7,8-tetrahydro-2-naphthalenyl)methoxy-[1,140 -biphenyl]-4'-(1,1-dimethylethyl)-6-carboxaldehyde (16o): From trillate 20a and stannane 3c; scale=0.43 mmol, yield=72%; chromatographed on silica gel using CH$_2$Cl$_2$/hexane; $^1$H NMR (300 MHz, CDCl$_3$) δ 9.74 (s, 1H, CHO), 7.62 (dd, J=2, 8 Hz, 1H, ArH), 7.44 (m, 3H, ArH), 7.32–7.17 (m, 5H, ArH), 6.92 (dd, J=2, 8 Hz, 1H, ArH), 5.00 (s, 2H, ArCH$_2$O), 1.64 (s, 4H, CH$_2$CH$_2$), 1.36 (s, 9H, C(CH$_3$)$_3$), 1.23

(s, 6H, 2×CH₃), 1.17 (s, 6H, 2×CH₃); ¹³C NMR (75 MHz, CDCl₃) δ 192.92 (C=O), 156.28, 150.70, 144.96, 144.30, 135.80, 135.72, 133.57, 130.91, 130.05, 128.46, 126.48, 124.90, 124.63, 123.83, 119.42, 117.84, 70.60, 34.99, 34.98, 34.67, 34.27, 34.09, 31.92, 31.83, 31.37; IR (film) 2960, 2928, 2864, 1690, 1456, 1258, 1240, 1066, 760 cm⁻¹; MS (DCI) m/e 455 (MH+), 201 (C₁₅H₂₁+).

For 2- (5,5,8,8-tetramethyl-5,6,7,8-tetrahydro-2-naphthalenyl)methoxy-440 -(2-tertbutyldimethylsilyloxy-1-ethyl)-[1,1′-biphenyl]-6-carboxaldehyde (16p): From trillate 20a and stannane 3e; scale=0.504 mmol, yield=94%; chromatographed on silica gel using EtOAc/hexane; ¹H NMR (300 MHz, CDCl₃) δ 9.77 (s, 1H, (CHO), 7.62 (d, J=8 Hz, 1H, ArH), 7.41 (dd, J=8, 8 Hz, 1H, ArH), 7.24 (m, 6H, ArH), 7.15 (d, J=2 Hz, 1H, ArH), 6.96 (dd, J=2, 8 Hz, 1H, ArH), 5.01 (s, 2H, ArCH₂O), 3.87 (t, J=7 Hz, 2H, R₃SiOCH₂), 2.90 (t, J=7 Hz, 2H; ArCH₂CH₂), 1.67 (s, 4H, CH₂CH₂), 1.26 (s, 6H, 2×CH₃), 1.18 (s, 6H, 2×CH₃), 0.89 (s, 9H, C(CH₃)₃), 0.01 (s, 6H, Si(CH₃)₂).

Example 14: Procedure for the Synthesis of Acid 14q

2-Trifluoromethylsulphonyloxy-3-(5,5,7,8-tetrahydro-5,5,8,8-tetramethyl-2-naphthahenyl)methoxybenzaldehyde (20a) (0.826 g., 1.76 mmol; see Example 13) is coupled to stannane 3g (1.19 g., 2.63 mmol; see Example 2) via the method of Example 3 to yield 3′-(ethoxy-carbonylmethyl)-2-(5,6,7,8-tetraahydro-5,5,8,8-tetramethyl-2-naphthalenyl)methoxy-1,1′-biphenyl-6-carboxaldehyde (16q) (0.410 g., 0.88 mmol, 50%): chromatographed on silica gel using 5% EtOAc/hexane to afford a yellow oil as a 3:1 mixture of 16q and triflate 20a.

3′-Ethoxycarbonylmethyl-2-(5,6,7,8-tetrahydro-5,5,8,8 -tetramethyl-2-naphthalenyl)methoxy-1,1′-biphenyl-6-carboxaldehyde (16q) (0.394 g., 0.84 mmol) obtained above (as a mixture with triflate 20a) is oxidized via the method of Example 4 to yield 3′ethoxycarbonylmethyl-2-(5,6,7,8-tetrahydro-5,5,8,8-tetramethyl-2-naphthalenyl)methoxy-1,1′-biphenyl-6-carboxylic acid (0.210 g., 0.43 mmol, 25% overall from triflate 20a): chromatographed on silica gel using methanol/CH₂Cl₂ to afford a yellow oil; ¹H NMR (300 MHz, CDCl₃) δ 7.49 (d, J=8 Hz, 1H, ArH), 7.33 (m, 2H, ArH), 7.26–7.15 (m, 5H, ArH), 7.05 (d, J=2 Hz, 1H, ArH), 6.89 (dd, J=2, 8 Hz, 1H, ArH), 4.94 (s, 2H, ArCH₂O), 4.05 (q, J=7Hz, 2H, CO₂CH₂), 3.59 (s, 2H, ArCH₂CO₂), 1.63 (s, 4H, CH₂CH₂), 1.22 (s, 6H, 2×CH₃), 1.15 (s, 6H, 2×CH₃), 1.15 (t, J=7 Hz, 3H, CO₂CH₂CH₃); ¹³C NMR (75 MHz, CDCl₃) δ 171.68 (C=O), 171.64 (C=O), 156.21, 144.87, 144.23, 136.72, 133.58, 133.44, 132.16, 130.56, 128.42, 128.37, 128.01, 127.89, 126.55, 124.67, 123.89, 122.57, 116.76, 70.69, 60.80, 41.43, 35.03, 34.19, 34.07, 31.82, 31.74, 14.12; IR (film) 2960, 2926, 1734, 1700, 1456, 1364, 1300, 1260, 1152, 758 cm⁻¹; MS (DCI) m/e 501 (MH+), 483 (M-OH), 201 (C₁₅H₂₁+).

3′-Ethoxycarbonylmethyl-2-(5,6,7,8-tetrahydro-5,5,8,8-tetramethyl-2-naphthalenyl)methoxy-1,1′-biphenyl-6-carboxylic acid (0.199 g., 0.41 mmol) is hydrolyzed via the method of Example 7 to afford 6-carboxy-2-[5,6,7,8-tetrahydro-5,5,8,8-tetramethyl-2-naphthalenyl]methoxy-[1,1′-biphenyl]-3′-acetic acid (14q) (0.169 g., 0.37 mmol, 90%) as a yellow solid: UV$_{max}$ (MeOH) 208 nm (ε=42683), 292 nm (ε=3412); ¹H NMR (300 MHz, CD₃OD) δ 7.39–7.17 (m, 8H, ArH), 7.10 (d, J=2 Hz, 1H, ArH), 6.93 (dd, J=2, 8 Hz, 1H, ArH), 4.96 (s, 2H, ArCH₂O), 3.59 (s, 2H, ArCH₂CO₂), 1.65 (s, 4H, CH₂CH₂), 1.22 (s, 6H, 2×CH₃), 1.15 (s, 6H, 2×CH₃); ¹³C NMR (75 MHz, CD₃OD) δ 175.49 (C=O), 172.19 (C=O), 157.42, 145.81, 145.16, 138.56, 135.60, 135.25, 135.19, 132.46, 131.86, 129.65, 129.50, 128.92, 128.73, 127.54, 126.02, 125.32, 122.37, 117.06, 71.56, 42.09, 36.21, 35.17, 35.00, 32.29, 32.25; IR (KBr) 3430, 2960, 2926, 1706, 1456, 1298, 1260 cm⁻¹; MS (DCI) m/e 473 (MH+), 472 (M+), 455 (M-OH), 201 (C₁₅H₂₁+). Anal. Calcd for C₃₀H₃₂O₅.0.5 H₂O: C, 74.82; H, 6.91. Found: C, 74.87; H, 6.74.

Experimental Procedures for Compounds of Type IB

Example 15: General Procedure for Wittig Homologation of Aldehydes to Enol Ethers The synthesis of (Z) and (E) 3′-carboethoxy-2-methoxy-6-[(1-methoxy)-2-ethenyl]-1,1′-biphenyl (21) is illustrative:

A solution of (methoxymethyl)triphenylphosphonium chloride (3.88 g, 11.3 mmol, 1.05 equiv.) in 15 mL of toluene and 50 mL of THF is cooled to 0° C. Potassium t-butoxide (95%, 1.53 g, 12.9 mmol, 1.21 equiv.) is then added, and the mixture allowed to stir at 0° C. for 30 minutes. A solution of 2-methoxy-3′-carboethoxy-[1,1′-biphenyl]-6-carboxaldehyde (4a) (3.05 g, 10.7 mmol, 1 equiv.) in 15 mL of THF is then added rapidly dropwise, and the mixture allowed to stir for 5 minutes. The ice-bath is removed, and stirring continued at 0° C. for another 2 hours at room temperature. The reaction mixture is partitioned between ether and water, and the organic phase washed with brine, dried (MgSO₄), and concentrated. Pentane is added to precipitate Ph₃PO, which is removed by filtration. The filtrate is concentrated to afford an oil. The crude material is chromatographed on silica gel using methylene chloride/hexane as the eluent to afford a mixture of (Z) and (E) 3′-carboethoxy-2-methoxy-6-[(1-methoxy)-2-ethenyl]-1,1′-biphenyl (21) (3.27 g, 10.5 mmol, 98%) as a clear oil (~2:1 mixture of E:Z isomers): Data for E isomer: ¹H NMR (300 MHz, CDCl₃) δ 8.04 (d, J=8 Hz, 1H, ArH), 7.95 (s, 1H, ArH), 7.50–7.27 (m, 3H, ArH), 7.19 (d, J=8 Hz, 1H, ArH), 6.90 (d, J=12 Hz, 1H, C=CH), 6.81 (d, J=8 Hz, 1H, ArH), 5.41 (d, J=12 Hz, 1H, C=CH), 4.38 (q, J=7 Hz, 2H, CO₂CH₂), 3.71 (s, 3H, OCH₃), 3.45 (s, 3H, OCH₃), 1.36 (t, J=7 Hz, 3H, CO₂CH₂CH₃).

For (Z) and (E) 2- (5,5,8,8-tetramethyl-5,6,7,8-tetrahydro-2-naphthalenyl)methoxy-6-[(1-methoxy)-2-ethenyl]-1,1′-biphenyl (31e): scale=0.92 mmol, yield=93%; chromatographed on silica gel using 10% EtOAc/hexane to afford a white solid (~2:1 mixture of E:Z isomers); ¹H NHR (300 MHz, CDCl₃) δ 7.65 (d, J=8 Hz, 1H, ArH, from Z isomer), 7.41–7.37 (m, ArH from E and Z), 7.33–7.14 (m, ArH from E and Z), 7.04 (m, ArH, from E and Z), 6.89 (m, ArH, from E and Z), 5.99 (d, J=7 Hz, 1H, ArHC=C, from Z isomer), 5.50 (d, J=13 Hz, 1H, ArHC=C, from E isomer), 4.91 (s, 2H, ArCH₂O, from E isomer), 4.89 (s, 2H, ArCH₂O, from Z isomer), 3.71 (s, 3H, OCH₃ from Z isomer), 3.44 (s, 3H, OCH₃ from E isomer), 1.61 (s, 4H, CH₂CH₂ from E isomer), 1.60 (s, 4H, CH₂CH₂ from Z isomer), 1.21 (s, 6H, 2×CH₃), 1.13 (s, 6H, 2×CH₃); ¹³C NHR (75 MHz, CDCl₃) δ 148.95, 134.21, 130.70, 128.16, 127.87, 126.75, 126.33, 124.61, 123.75, 121.90, 117.14, 110.50 (Z isomer), 110.30 (E isomer), 104.22 (E isomer), 103.64 (Z isomer), 70.14, 61.00 (Z isomer), 56.36 (E isomer), 35.09, 35.02, 34.21, 34.04, 31.83, 31.71; IR (KBr) 3440, 2956, 2922, 1636, 1454, 1258, 1212, 1066, 700 cm⁻¹; MS (DCI) m/e 427 (MH+), 395 (M-OCH₃), 201 (C₁₅H₂₁+).

For (Z) and (E) 2-(5,5,8,8-tetramethyl-5,6,7,8-tetrahydro-2-naphthalenyl)methoxy-3'-carboethoxy-6-[(1-methoxy)-2-ethenyl]-1,1'-biphenyl (31f): scale=1.02 mmol, yield=91%; chromatographed on silica gel using 20% EtOAc/hexane to afford a white solid (~2:1 mixture of E:Z isomers); $^1$H NMR (300 MHz, CDCl$_3$) δ 8.35 (ddd, J=2, 2, 8 Hz, 1H, ArH from Z isomer), 8.08 (m, ArH from E and Z), 7.82 (ddd, J=2, 2, 8 Hz, 1H, ArH from E isomer), 7.59–7.49 (m, ArH from E and Z), 7.37–7.20 (m, ArH from E and Z), 7.11 (d, J=8 Hz, 1H, ArH from E isomer), 7.07 (m, ArH, from E and Z), 6.94 (m, ArH, from E and Z), 6.03 (d, J=8 Hz, CH=C from Z isomer), 5.49 (d, J=14 Hz, CH=C from E isomer), 4.99 (s, 2H, ArCH$_2$O from E isomer), 4.98 (s, 2H, ArCH$_2$O from Z isomer), 4.89 (d, J=8 Hz, CH=C from Z isomer), 4.41 (m, 2H, CO$_2$CH$_2$ from E and Z), 3.75 (s, 3H, OCH$_3$ from Z isomer), 3.49 (s, 3H, OCH$_3$ from E isomer), 1.45 (t, J=7 Hz, 3H, CO$_2$CH$_2$CH$_3$ from Z isomer), 1.41 (t, J=7 Hz, 3H, CO$_2$CH$_2$CH$_3$ from E isomer), 1.25 (s, 6H, 2×CH$_3$), 1.15 (s, 6H, 2×CH$_3$).

Example 16: General Procedure for Hydrolysis of Enol Ethers to Aldehydes

The synthesis of 3'-carboethoxy-2-methoxy-1,1'-biphenyl-6-acetaldehyde (22) is representative:

3'-Carboethoxy-2-methoxy-6-[(1-methoxy)-2-ethenyl]-1,1'-biphenyl (21) (3.27 g, 10.5 mmol), as a mixture of Z and E isomers, is dissolved in 31 mL of THF and 31 mL of 1N HCl. The mixture is heated to reflux for 24 hours, and then partitioned between ethyl acetate and water. The organic phase is washed with brine, dried (MgSO$_4$), and concentrated. Crude 3'-carboethoxy-2-methoxy-1,1'-biphenyl-6-acetaldehyde (22) is obtained as a yellow oil (3.30 g, 11.1 mmol), which is of suitable purity for use in subsequent reactions: $^1$H NMR (300 MHz, CDCl$_3$) δ 9.55 (s, 1H, CHO), 8.03 (d, J=8 Hz, 1H, ArH), 7.49–7.34 (m, 4H, ArH), 6.93 (d, J=8 Hz, 1H, ArH), 6.88 (d, J=8 Hz, 1H, ArH), 4.36 (q, J=7 Hz, 2H, CO$_2$CH$_2$), 3.72 (s, 3H, OCH$_3$), 3.49 (s, 2H, ArCH$_2$CHO), 1.38 (t, J=7 Hz, 3H, CO$_2$CH$_2$CH$_3$); $^{13}$C NMR (75 MHz, CDCl$_3$) δ 199.08 (C=O), 166.45 (C=O), 157.34, 136.86, 134.60, 132.03, 131.09, 130.71, 130.63, 129.11, 128.54, 128.38, 122.61, 109.99, 61.02, 55.74, 48.32, 14.32.

For 2-(5,5,8,8-tetramethyl-5,6,7,8-tetrahydro-2-naphthalenyl)methoxy-1,1'-biphenyl-6-acetaldehyde (32e): $^1$H NMR (300 MHz, CDCl$_3$) δ 9.57 (bs, 1H, CHO), 7.42–7.27 (m, 4H, ArH), 7.23–7.18 (m, 3H, ArH), 7.02 (m, 2H, ArH), 6.96 (m, 2H, ArH), 4.98 (s, 2H, ArCH$_2$O), 3.53 (bs, 2H, ArCH$_2$CHO), 1.64 (s, 4H, CH$_2$CH$_2$), 1.24 (s, 6H, 2×CH$_3$), 1.14 (s, 6H, 2×CH$_3$).

For 2-(5,5,8,8-tetramethyl-5,6,7,8-tetrahydro-2-naphthalenyl)methoxy-3'-carboethoxy-1,1'-biphenyl-6-acetaldehyde (32f): $^1$H NMR (300 MHz, CDCl$_3$) δ 9.61 (bs, 1H, CHO), 8.10 (m, 2H, ArH), 7.60–7.49 (m, 2H, ArH), 7.39 (dd, J=8, 8 Hz, 1H, ArH), 7.22 (d, J=8 Hz, 1H, ArH), 7.08 (m, 2H, ArH), 6.96 (m, 2H, ArH), 5.01 (s, 2H, ArCH$_2$O), 4.43 (q, J=7 Hz, 2H, CO$_2$CH$_2$), 3.56 (bs, 2H, ArCH$_2$CHO), 1.58 (s, 4H, CH$_2$CH$_2$), 1.39 (t, J=7 Hz, CO$_2$CH$_2$CH$_3$), 1.29 (s, 6H, 2×CH$_3$), 1.17 (s, 6H, 2×CH$_3$).

Example 17: Synthesis of Ester 24

3'-Carboethoxy-2-methoxy-1,1'-biphenyl-6-acetaldehyde (22) (3.30 g. crude, from Example 16) is oxidized following the general procedure of Example 4 to afford crude 3'-carboethoxy-2-methoxy-1,1'-biphenyl-6-acetic acid (23) (3.78 g.), which is of suitable purity for use in subsequent reactions: $^1$H NMR (300 MHz, CDCl$_3$) δ 8.05 (d, J=7 Hz, 1H, ArH), 7.90 (s, 1H, ArH), 7.55–7.31 (m, 3H, ArH), 6.95 (d, J=7 Hz, 1H, ArH), 6.85 (d, J=7 Hz, 1H, ArH), 4.35 (q, J=7 Hz, 2H, CO$_2$CH$_2$), 3.70 (s, 3H, OCH$_3$), 3.40 (s, 2H, ArCH$_2$CO$_2$), 1.33 (t, J=7 Hz, 3H, CO$_2$CH$_2$CH$_3$); $^{13}$C NMR (75 MHz, CDCl$_3$) δ 177.40 (C=O), 166.72 (C=O), 157.08, 136.89, 134.81, 133.36, 131.26, 130.50, 130.41, 128.87, 128.50, 128.31, 122.49, 109.91, 61.07, 55.73, 38.72, 14.28.

Acid 23 (3.78 g. crude, from above) is converted to the diethyl ester using the general procedure of Example 5 to afford 3'-carboethoxy-2-methoxy-1,1'-biphenyl-6-acetic acid, ethyl ester (24) (2.77 g., 8.10 mmol, 77% overall yield from enol ether 21): chromatographed on silica gel using EtOAc/hexane; UV$_{max}$ (EtOH) 206 nm (ε=28222), 282 nm (ε=817); $^1$H NMR (300 MHz, CDCl$_3$) δ 8.06 (dd, J=2, 8 Hz, 1H, ArH), 7.91 (s, 1H, ArH), 7.56–7.31 (m, 3H, ArH), 6.98 (d, J=8 Hz, 1H, ArH), 6.90 (d, J=8 Hz, 1H, ArH), 4.67 (s, 1H, OH), 4.37 (q, J=7 Hz, 2H, CO$_2$CH$_2$), 4.02 (q, J=7 Hz, 2H, CO$_2$CH$_2$), 3.68 (s, 3H, OCH$_3$), 3.35 (s, 2H, ArCH$_2$CO$_2$), 1.37 (t, J=7 Hz, 3H, CO$_2$CH$_2$CH$_3$), 1.13 t, J=7 Hz, 3H, CO$_2$CH$_2$CH$_3$); $^{13}$C NMR (75 MHz, CDCl$_3$) δ 171.52 (C=O), 166.60 (C=O), 157.05, 137.03, 134.76, 134.07, 131.22, 130.42, 128.74, 128.38, 128.12, 122.44, 109.69, 60.92, 60.74, 55.75, 39.17, 14.33, 14.06; IR (KBr) 2990, 1735, 1718, 1580, 1470, 1300, 1255, 1235 cm$^{-1}$; MS (DCI) m/e 343 (MH+). Anal. Calcd for C$_{20}$H$_{22}$O$_5$.0.10 hexane: C, 71.10; H, 6.68. Found: C, 71.39; H, 6.36.

Example 18: Synthesis of Phenol 25 and Triflate 26

3'-Carboethoxy-2-methoxy-1,1'-biphenyl-6-acetic acid, ethyl ester (24) (2.77 g., 8.10 mmol) is converted via the method of Example 6 to 3'-carboethoxy-2-hydroxy-1,1'-biphenyl-6-acetic acid, ethyl ester (25) (2.40 g., 7.32 mmol, 90%): chromatographed on silica gel using EtOAc/hexane; $^1$H NMR (300 MHz, CDCl$_3$) δ 8.12 (d, J=8 Hz, 1H, ArH), 7.96 (s, 1H, ArH), 7.56 (dd, J=8, 8 Hz, 1H, ArH), 7.50 (d, J=8 Hz, 1H, ArH), 7.24 (d, J=8 Hz, 1H, ArH), 6.92 (d, J=8 Hz, 1H, ArH), 6.90 (d, J=8 Hz, 1H, ArH), 4.67 (s, 1H, OH), 4.37 (q, J=7 Hz, 2H, CO$_2$CH$_2$), 4.02 (q, J=7 Hz, 2H, CO$_2$CH$_2$), 3.35 (s, 2H, ArCH$_2$CO$_2$), 1.37 (t, J=7 Hz, 3H, CO$_2$CH$_2$CH$_3$), 1.13 (t, J=7 Hz, 3H, CO$_2$CH$_2$CH$_3$); $^{13}$C NMR (75 MHz, CDCl$_3$) δ 171.35 (C=O), 152.99, 135.00, 134.87, 133.74, 131.49, 129.66, 129.40, 129.24, 122.39, 114.44, 61.24, 60.81, 39.27, 14.30, 14.05; MS (DCI) m/e 329 (MH+).

Phenol 25 (1.13 g., 3.45 mmol) is converted by the method of Example 1 to 3'-carboethoxy-2-trifluoromethylsulphonyloxy-1,1'-biphenyl-6-acetic acid, ethyl ester (26) (1.21 g., 2.63 mmol, 76%): chromatographed on silica gel using CH$_2$Cl$_2$/hexane; $^1$H NMR (300 MHz, CDCl$_3$) δ 8.17 (ddd, J=2, 2, 8 Hz, 1H, ArH), 7.94 (dd, J=2, 2 Hz, 1H, ArH), 7.54 (dd, J=8, 8 Hz, 1H, ArH), 7.44 (m, 3H, ArH), 7.33 (dd, J=2, 8 Hz, 1H, ArH), 4.39 (q, J=7 Hz, 2H, CO$_2$CH$_2$), 4.05 (q, J=7 Hz, 2H, CO$_2$CH$_2$), 3.48 (s, 2H, ArCH$_2$), 1.39 (t, J=7 Hz, 3H, CO$_2$CH$_2$CH$_3$), 1.15 (t, J=7 Hz, 3H, CO$_2$CH$_2$CH$_3$).

Example 19: Synthesis of Diacids 28a–c

Synthesis of 28a:

Tributyl (styryl) stannane (ca. 10:1 mixture of E:Z; see Labadie, J. W.; Stille, J. K. J. Am. Chem. Soc. 1983, 105, 6129–6137) (0.332 g., 0.845 mmol) is coupled with triflate 26 (0.259 g., 0.563 mmol; from Example 18) via heating at 110° C. for 20 minutes following the general method of Example 3 to afford (after chromatography on silica gel using 20% EtOAc/hexane) a 10:1 mixture of (E) and (Z) 2-styryl-6-ethoxycarbonylmethyl-1,1'-biphenyl-3'-carboxylic acid, ethyl ester (27a) (0.221 g., 0.534 mmol, 95%). A second chromatographic purification utilizing a gradient elution of EtOAc/hexane is necessary to separate the isomers: Data for E-27a: $^1$H NMR (300 MHz, CDCl$_3$) δ 8.12 (ddd, J=2, 2, 8 Hz, 1H, ArH), 7.91 (dd, J=2, 2 Hz, 1H, ArH), 7.72 (d, J=8 Hz, 1H, ArH), 7.52 (dd, J=8, 8 Hz, 1H, ArH), 7.40 (m, 2H, ArH), 7.29 (dd, J=2, 8 Hz, 1H, ArH), 7.23 (m, 5H, ArH), 6.99 (d, J=17 Hz, 1H, CH=C), 6.66 (d, J=17 Hz, 1H, CH=C), 4.39 (q, J=7 Hz, 2H, CO$_2$CH$_2$), 4.04 (q, J=7 Hz, 2H, CO$_2$CH$_2$), 3.40 (s, 2H, ArCH$_2$), 1.37 (t, J=7 Hz, 3H, CO$_2$CH$_2$CH$_3$), 1.15 (t, J=7 Hz, 3H, CO$_2$CH$_2$CH$_3$). Data for Z-27a: $^1$H NMR (300 MHz, CDCl$_3$) δ 8.03 (ddd, J=2, 2, 8 Hz, 1H, ArH), 7.86 (dd, J=2, 2 Hz, 1H, ArH), 7.43 (dd, J=8, 8 Hz, 1H, ArH), 7.37 (ddd, J=2, 2, 8 Hz, 1H, ArH), 7.24–7.15 (m, 8H, ArH), 6.34 (d, J=12 Hz, 1H, CH=C), 6.16 (d, J=12 Hz, 1H, CH=C), 4.37 (q, J=7 Hz, 2H, CO$_2$CH$_2$), 4.04 (q, J=7 Hz, 2H, CO$_2$CH$_2$), 3.42 (s, 2H, ArCH$_2$), 1.35 (t, J=7 Hz, 3H, CO$_2$CH$_2$CH$_3$), 1.16 (t, J=7 Hz, 3H, CO$_2$CH$_2$CH$_3$).

(E) 2-Styryl-6-ethoxycarbonylmethyl-1,1'-biphenyl-3'-carboxylic acid, ethyl ester (E-27a) (0.123 g., 0.297 mmol) is hydrolyzed according to the general procedure of Example 7 to yield (E) 2-styryl-6-carboxymethyl-1,1'-biphenyl-3'-carboxylic acid (28a) (0.091 g., 0.254 mmol, 86%): chromatographed on reverse-phase C-18 silica gel using water/methanol as eluent, then crystallized from CH$_2$Cl$_2$/pentane; UV$_{max}$ (EtOH) 206 nm (ε=27755), 228 nm (ε=26398), 302 nm (ε=22153); $^1$H NMR (300 MHz, CD$_3$OD) δ 8.09 (d, J=8 Hz, 1H, ArH), 7.87 (s, 1H, ArH), 7.74 (d, J=8 Hz, 1H, ArH), 7.58 (dd, J=8, 8 Hz, 1H, ArH), 7.39 (m, 2H, ArH), 7.29 (d, J=8 Hz, 1H, ArH), 7.17 (m, 5H, ArH), 7.00 (d, J=16 Hz, 1H, C=CH), 6.65 (d, J=16 Hz, 1H, C=CH), 3.39 (s, 2H, ArCH$_2$); $^{13}$C NMR (75 MHz, CD$_3$OD) δ 175.39 (C=O), 169.62 (C=O), 141.62, 140.87, 138.73, 137.68, 135.89, 134.75, 132.35, 130.99, 130.93, 129.89, 129.70, 129.64, 129.15, 128.64, 128.05, 127.36, 125.19, 40.13; IR (KBr) 3422, 2922, 1700, 1410, 1306, 1258, 744 cm$^{-1}$; MS (DCI) m/e 359 (MH+), 358 (M+), 341 (M-OH). Anal. Calcd for C$_{23}$H$_{18}$O$_4$.0.25 H$_2$O: C, 76.12; H, 5.14. Found: C, 76.27; H, 5.14.

Synthesis of 28b:

As described above for 28a, stannane 9 (0.860 g., 1.66 mmol; from Example 9) is coupled to triflate 26 (0.302 g., 0.657 mmol; from Example 18) by the method of Example 3. After heating at 110° C. for 15 minutes the reaction is incomplete as judged by thin-layer chromatography. The bath temperature is raised to 130° C., and heating is continued for another 10 minutes to complete the reaction. 3'-Carboethoxy-(E)-2-[(5,6,7,8-tetrahydro-5,5,8,8,-tetramethyl-2-naphthalenyl)-1-propenyl]-[1,1'-biphenyl]-6-acetic acid, ethyl ester (27b) (0.309 g., 0.574 mmol, 87%) is obtained as a clear oil: chromatographed on silica gel using EtOAc/hexane; UV$_{max}$ (EtOH) 208 nm (ε=30099), 276 nm (ε=13855); $^1$H NMR (300 MHz, CDCl$_3$) δ 8.04 (ddd, J=2, 2, 8 Hz, 1H, ArH), 7.87 (dd, J=2, 2 Hz, 1H, ArH), 7.46 (dd, J=8, 8 Hz, 1H, ArH), 7.37 (m, 3H, ArH), 7.26 (dd, J=2, 8 Hz, 1H, ArH), 7.15 (d, J=8 Hz, 1H, ArH), 6.96 (d, J=2 Hz, 1H, ArH), 6.92 (dd, J=2, 8 Hz, 1H, ArH), 6.26 (s, 1H, C=CH), 4.33 (q, J=7 Hz, 2H, CO$_2$CH$_2$), 4.02 (q, J=7 Hz, 2H, CO$_2$CH$_2$), 3.43 (s, 2H, ArCH$_2$), 2.11 (s, 3H, CH$_3$), 1.61 (s, 4H, CH$_2$CH$_2$), 1.34 (t, J=7 Hz, 3H, CO$_2$CH$_2$CH$_3$), 1.22 (s, 6H, 2×CH$_3$), 1.15 (m, 9H, CO$_2$CH$_2$CH$_3$ and 2×CH$_3$); $^{13}$C NMR (75 MHz, CDCl$_3$) δ 171.68 (C=O), 166.44 (C=O), 144.46, 143.85, 140.83, 140.57, 139.90, 137.92, 136.78, 134.47, 132.50, 130.78, 130.45, 128.62, 128.49, 128.44, 128.26, 127.41, 126.51, 126.24, 123.94, 123.12, 60.97, 60.76, 39.49, 35.10, 34.99, 34.18, 34.01, 31.74, 17.24, 14.29, 14.09; IR (film) 2960, 2928, 1722, 1462, 1366, 1298, 1240, 1158, 1110, 1034, 752 cm$^{-1}$; MS (DCI) m/e 539 (MH+), 493 (M-C$_2$H$_5$O). Anal. Calcd for C$_{36}$H$_{42}$O$_4$.1.25 H$_2$O: C, 77.04; H, 7.99. Found: C, 76.79; H, 7.65.

3'-Carboethoxy-(E)-2-[(5,6,7,8-tetrahydro-5,5,8,8,-tetramethyl-2-naphthalenyl)-1-propenyl]-[1,1'-biphenyl]-6-acetic acid, ethyl ester (27b) (0.476 g., 0.885 mmol) is hydrolyzed according to the general procedure of Example 7 to yield 3'-carboxy-(E)-2-[(5,6,7,8-tetrahydro-5,5,8,8,-tetramethyl-2-naphthalenyl)-1-propenyl]-[1,1'-biphenyl]-6-acetic acid (28b) (0.380 g., 0.788 mmol, 89%): crystallized from CH$_2$Cl$_2$/pentane; mp=253.5°–255.5° C; UV$_{max}$ (EtOH) 210 nm (ε=38336), 276 nm (ε=15928); $^1$H NMR (300 MHz, DMSO-d$_6$) δ 7.95 (d, J=8 Hz, 1H, ArH), 7.70 (s, 1H, ArH), 7.56 (dd, J=8, 8 Hz, 1H, ArH), 7.43–7.29 (m, 4H, ArH), 7.17 (d, J=8 Hz, 1H, ArH), 6.91 (d, J=8 Hz, 1H, ArH), 6.85 (d, J=2 Hz, 1H, ArH), 6.15 (s, 1H, C=CH), 3.36 (s, 2H, ArCH$_2$), 2.06 (s, 3H, CH$_3$), 1.56 (s, 4H, CH$_2$CH$_2$), 1.16 (s, 6H, 2×CH$_3$), 1.08 (s, 6H, 2×CH$_3$); $^{13}$C NMR (75 MHz, DMSO-d$_6$) ε 172.46 (C=O), 167.09 (C=O), 144.01, 143.48, 140.57, 140.23, 139.53, 136.69, 136.30, 133.92, 133.15, 130.66, 130.52, 129.13, 128.56, 128.14, 127.87, 127.25, 126.22, 125.98, 123.32, 122.95, 34.58, 34.48, 33.74, 33.67, 31.47, 17.00; IR (KBr) 3422, 2964, 2926, 1698, 1460, 1432, 1406, 1292, 1258, 748 cm$^{-1}$; MS (DCI) m/e 483 (MH+), 465 (M-OH). Anal. Calcd for C$_{34}$H$_{34}$O$_4$.0.25 H$_2$O: C, 78.90; H, 7.13. Found: C, 78.84; H, 7.10.

Synthesis of 28c:

2-Bromo-5,5,8,8-tetramethyl-5,6,7,8-tetrahydroanthracene (2.03 g., 6.42 mmol) (for a synthesis of this bromide see: Dawson, M. I., Hobbs, P. D., Dorsky, A., Morimoto, H., *J. Labelled Compounds and Radiopharmaceuticals* 1990, 28, 89) is converted to 2-tributylstannyl-5,5,8,8-tetramethyl-5,6,7,8-tetrahydroanthracene (3.28 g., 6.22 mmol, 97%) via the method of Example 2 (Procedure B): chromatographed on silica gel using hexane, then CH$_2$Cl$_2$/hexane as eluent to yield a clear oil; $^1$H NMR (300 MHz, CDCl$_3$) δ 7.82 (s, 1H, ArH), 7.74 (s, 2H, ArH), 7.67 (d, J=8 Hz, 1H, ArH), 7.41 (d, J=8 Hz, 1H, ArH), 1.76 (s, 4H, CH$_2$CH$_2$), 1.57 (m, 6H, butyl), 1.35 (m, 18H, 4×CH$_3$ and butyl), 1.09 (m, 6H, butyl), 0.88 (m, 9H, butyl); $^{13}$C NMR (75 MHz, CDCl$_3$) δ 144.18, 144.10, 138.24, 135.81, 132.28, 131.77, 131.63, 125.99, 124.79, 124.54, 35.15, 34.60, 34.57, 32.57, 30.83, 29.45, 29.03, 27.73, 27.43, 13.74, 9.60, 7.88; IR (film) 2956, 2926, 2870, 2854, 1462, 1376, 1362 cm$^{-1}$; MS (DCI) m/e 529 (MH+).

2-Tributylstannyl-6,6,9,9-tetramethyl-6,7,8,9-tetrahydro-anthracene (0.775 g., 1.47 mmol) is coupled to triflate 26 (0.451 g., 0.980 mmol) by the method of Example 3 to provide 3'-carboethoxy-2-[(1,2,3,4-tetrahydro-1,1,4,4-tetramethyl)-6-anthracenyl]-[1,1'-biphenyl]-6-acetic acid, ethyl ester (27c) (0.355 g., 0.650 mmol, 66%) as a clear oil: chromatographed on silica gel using EtOAc/hexane; UV$_{max}$ (CHCl$_3$) 244 nm (ε=37190); $^1$H NMR (300 MHz, CDCl$_3$) δ 7.86 (d, J=2 Hz, 1H, ArH), 7.84 (ddd, J=2, 2, 8 Hz, 1H, ArH), 7.65 (s, 1H, ArH), 7.62 (s, 1H, ArH), 7.57 (s, 1H, ArH), 7.38 (m, 4H, ArH), 7.22 (m, 2H, ArH), 6.88 (dd, J=2, 8 Hz, 1H, ArH), 4.28 (m, 2H, CO$_2$CH$_2$), 4.03 (q, J=7 Hz, 2H, CO$_2$CH$_2$), 3.51

(d, J=16 Hz, 1H, ArCH$_2$CO$_2$), 3.43 (d, J=16 Hz, 1H, ArCH$_2$CO$_2$), 1.73 (s, 4H, CH$_2$CH$_2$), 1.36 (s, 3H, CH$_3$), 1.35 (s, 3H, CH$_3$), 1.33 (s, 6H, 2×CH$_3$), 1.29 (t, J=7 Hz, 3H, CO$_2$CH$_2$CH$_3$), 1.15 (t, J=7 Hz, 3H, CO$_2$CH$_2$CH$_3$); $^{13}$C NMR (75 MHz, CDCl$_3$) δ 171.72 (C=O), 166.48 (C=O), 144.36, 144.29, 142.22, 139.81, 139.64, 138.24, 135.12, 133.06, 131.49, 130.26, 129.99, 129.73, 129.48, 128.01, 127.88, 127.82, 127.36, 126.00, 124.95, 124.53, 60.89, 60.81, 39.73, 35.06, 34.54, 32.49, 14.24, 14.10; IR (film) 2960, 2926, 2860, 1734, 1720, 1462, 1298, 1232, 1110 cm$^{-1}$; MS (DCI) m/e 549 (MH+), 503 (M-C$_2$H$_5$O).

3'-Carboethoxy-2-[(1,2,3,4-tetrahydro-1,1,4,4-tetramethyl)-6-anthracenyl]-[1,1'-biphenyl]-6-acetic acid, ethyl ester (27c) (0.225 g., 0.405 mmol) is hydrolyzed according to the general procedure of Example 7 to yield 3'-carboxy-2-[(1,2,3,4-tetrahydro-1,1,4,4-tetramethyl)-6-anthracenyl]-[1,1'-biphenyl]-6-acetic acid (28c) (0.113 g., 0.230 mmol, 57%) as a white solid: crystallized from CH$_2$Cl$_2$/pentane; mp=235°-240° C.; UV$_{max}$ (CHCl$_3$) 242 nm (ε=39630); $^1$H NMR (300 MHz, CDCl$_3$) δ 7.86 (ddd, J=2, 2, 8 Hz, 1H, ArH), 7.81 (s, 1H, ArH), 7.64 (s, 1H, ArH), 7.63 (s, 1H, ArH), 7.56 (s, 1H, ArH), 7.46-7.33 (m, 6H, ArH), 7.02 (dd, J=2, 8 Hz, 1H, ArH), 3.54 (d, J=16 Hz, 1H, ArCH$_2$CO$_2$), 3.47 (d, J=16 Hz, 1H, ArCH$_2$CO$_2$), 1.73 (s, 4H, CH$_2$CH$_2$), 1.36 (s, 3H, CH$_3$), 1.34 (s, 6H, 2×CH$_3$), 1.26 (s, 3H, CH$_3$); $^{13}$C NMR (75 MHz, CDCl$_3$) δ 178.87 (C=O), 172.12 (C=O), 144.46, 144.38, 142.18, 140.04, 139.58, 137.66, 135.03, 132.95, 132.67, 131.39, 130.31, 130.00, 128.90, 128.35, 128.12, 127.23, 126.15, 124.98, 124.51, 40.90, 35.04, 34.53, 32.49, 29.71; IR (KBr) 3420, 2960, 2926, 1704, 1298, 1248, 750 cm$^{-1}$; MS (DCI) m/e 493 (MH+), 475 (M-OH). Anal. Calcd for C$_{33}$H$_{32}$O$_4$.0.75 H$_2$O: C, 78.31; H, 6.67. Found: C, 78.32; H, 6.41.

Example 20: Synthesis of Diacids 30a-c

A. Synthesis of Diesters 29a-c

Alcohol 12c (0.987 g., 3.55 mmol; from Example 8) and phenol 25 (1.28 g., 3.90 mmol; from Example 18) are coupled using the method of Example 11 to afford 2-[(3,4-bispentyloxy)phenyl]-methoxy-3'-carboethoxy-[1,1'-biphenyl]-6-acetic acid, ethyl ester (29a) (0.957 g., 1.62 mmol, 46%) as a clear oil: chromatographed on silica gel using CH$_2$Cl$_2$/hexane; UV$_{max}$ (EtOH) 208 nm (ε=53224), 280 nm (ε=6773); $^1$H NMR (300 MHz, CDCl$_3$) δ 8.05 (dd, J=2, 8 Hz, 1H, ArH), 7.97 (s, 1H, ArH), 7.46 (m, 2H, ArH), 7.32 (dd, J=8, 8 Hz, 1H, ArH), 7.03 (d, J=8 Hz, 1H, ArH), 6.97 (d, J=8 Hz, 1H, ArH), 6.75 (d, J=8 Hz, 1H, ArH), 6.68 (dd, J=2, 8 Hz, 1H, ArH), 6.60 (s, 1H, ArH), 4.93 (s, 2H, ArCH$_2$O), 4.37 (q, J=7 Hz, 2H, CO$_2$CH$_2$), 4.06 (q, J=7 Hz, 2H, CO$_2$CH$_2$), 3.93 (t, J=6 Hz, 2H, OCH$_2$R), 3.76 (t, J=6 Hz, 2H, OCH$_2$R), 3.42 (s, 2H, ArCH$_2$CO$_2$), 1.82-0.93 (m, 24 H, pentyl and 2×CO$_2$CH$_2$CH$_3$); $^{13}$C NMR (75 MHz, CDCl$_3$) δ 171.45 (C=O), 166.45 (C=O), 156.11, 149.19, 148.37, 137.26, 134.90, 134.14, 131.32, 131.12, 130.36, 129.71, 128.76, 128.28, 128.03, 122.85, 118.82, 113.55, 111.93, 111.75, 70.80, 69.31, 68.83, 60.92, 60.73, 39.21, 29.01, 28.96, 28.31, 22.53, 14.33, 14.08; IR (KBr) 2930, 2955, 1720 (C=O), 1585, 1510, 1465, 1260, 1230 cm$^{-1}$; MS (DCI) m/e 591 (MH+), 525, 263. Anal. Calcd for C$_{36}$H$_{46}$O$_7$.0.1 CH$_2$Cl$_2$: C, 72.24; H, 7.80. Found: C, 72.50; H, 8.25.

For 2-[(3,4-biscyclopentyloxy)phenyl]methoxy-3'-carboethoxy-[1,1'-biphenyl]-6-acetic acid, ethyl ester (29b): From alcohol 12d (see Example 8) and phenol 25 (see Example 18); scale=1.19 mmol, yield=57%; chromatographed on silica gel using CH$_2$Cl$_2$/hexane; UV$_{max}$ (EtOH) 208 nm (ε=56239), 282 nm (ε=6164); $^1$H NMR (300 MHz, CDCl$_3$) δ 8.04 (dd, J=2, 5 Hz, 1H, ArH), 7.96 (s, 1H, ArH), 7.48 (d, J=5 Hz, 2H, ArH), 7.31 (dd, J=8, 8 Hz, 1H, ArH), 7.02 (d, J=8 Hz, 1H, ArH), 6.96 (d, J=8 Hz, 1H, ArH), 6.78 (d, J=8 Hz, 1H, ArH), 6.67 (d, J=8 Hz, 1H, ArH), 6.60 (s, 1H, ArH), 4.91 (s, 2H, ArCH$_2$O), 4.69-4.40 (m, 2H, 2×R$_2$CHOR), 4.35 (q, J=7 Hz, 2H, CO$_2$CH$_2$), 4.05 (q, J=7 Hz, 2H, CO$_2$CH$_2$), 3.41 (s, 2H, ArCH$_2$CO$_2$), 1.96-1.52 (m, 16H, cyclopentyl), 1.35 (t, J=7 Hz, 3H, CO$_2$CH$_2$CH$_3$); 1.15 (t, J=7 Hz, 3H, CO$_2$CH$_2$CH$_3$); $^{13}$C NMR (75 MHz, CDCl$_3$) δ 171.51 (C=O), 166.51 (C=O), 156.10, 148.88, 148.20, 137.18, 134.92, 134.12, 131.23, 131.06, 130.31, 129.87, 128.71, 128.27, 128.01, 122.78, 119.13, 116.61, 115.07, 111.71, 81.14, 81.08, 70.08, 60.91, 60.74, 39.20, 32.76, 32.71, 23.89, 23.83, 14.31, 14.06; IR (KBr) 2960, 1730 (C=O), 1720 (C=O), 1580, 1505, 1425, 1260, 1230 cm$^{-1}$; MS (DCI) m/e 587 (MH+), 586 (M), 519, 259. Anal. Calcd for C$_{36}$H$_{42}$O$_7$.0.1 H$_2$O: C, 72.73; H, 7.10. Found: C, 73.02; H, 6.69.

For 3'-carboethoxy-2-[4-decyloxyphenyl]methoxy-[1,1'-biphenyl]-6-acetic acid, ethyl ester (29c): From alcohol 12k (see Example 10) and phenol 25 (see Example 18); scale=0.958 mmol, yield=44%; chromatographed on silica gel using CH$_2$Cl$_2$/hexane; $^1$H NMR (300 MHz, CDCl$_3$) δ 8.07 (dd, J=2, 8 Hz, 1H, ArH), 7.98 (s, 1H, ArH), 7.49-7.47 (m, 2H, ArH), 7.31 (dd, J=8, 8 Hz, 1H, ArH), 7.08-6.80 (m, 4H, ArH), 6.77 (d, J=8 Hz, 2H, ArH), 4.94 (s, 2H, ArCH$_2$O), 4.38 (q, J=7 Hz, 2H, CO$_2$CH$_2$), 4.07 (q, J=7 Hz, 2H, CO$_2$CH$_2$), 3.94 (t, J=Hz, 2H, OCH$_2$R), 3.43 (s, 2H, ArCH$_2$CO$_2$), 1.76 (m, 2H, OCH$_2$CH$_2$R), 1.38 (t, J=7 Hz, 2H, CO$_2$CH$_2$CH$_3$), 1.28 (s, 14 H, R(CH$_2$)$_7$CH$_3$), 1.20 (t, J=7 Hz, 3H, CO$_2$CH$_2$CH$_3$), 0.90 (t, J=7 Hz, 3H, RCH$_3$); $^{13}$C NMR (75 MHz, CDCl$_3$) δ 171.54 (C=O), 158.61, 156.12, 137.03, 134.87, 134.08, 131.39, 130.25, 128.81, 128.70, 128.35, 128.18, 128.06, 122.82, 114.25, 111.90, 70.12, 67.93, 60.76, 39.22, 31.92, 29.59, 29.42, 29.36, 29.28, 22.72, 14.38, 14.18, 14.10.

B. Synthesis of Diacids 30a-c from Diesters 29a-c

2-[(3,4-Bispentyloxy)phenyl]methoxy-3'-carboethoxy-1,1'-biphenyl]-6-acetic acid, ethyl ester (29a) (0.295 g., 0.50 mmol) is hydrolyzed according to the general procedure of Example 7 to yield 2-[(3,4-bispentyloxy)phenyl]methoxy-3'-carboxy-[1,1'-biphenyl]-6-acetic acid (30a) (0.131 g., 0.245 mmol, 49%) as a white solid: chromatographed on reverse-phase C-18 silica gel using methanol; mp=105°-106° C.; UV$_{max}$ (EtOH) 208 nm (ε=52348), 280 nm (ε=6237); $^1$H NMR (300 MHz, CDCl$_3$) δ 8.03 (d, J=2 Hz, 1H, ArH), 8.01 (s, 1H, ArH), 7.52-7.46 (m, 2H, ArH), 7.34 (dd, J=8, 8 Hz, 1H, ArH), 7.04 (d, J=8 Hz, 1H, ArH), 6.98 (d, J=8 Hz, 1H, ArH), 6.70 (d, J=8 Hz, 1H, ArH), 6.63 (dd, J=2, 8 Hz, 1H, ArH), 6.59 (s, 1H, ArH), 4.94 (s, 2H, ArCH$_2$O), 3.95-3.69 (m, 4H, 2×RCH$_2$O), 3.48 (s, 2H, ArCH$_2$CO$_2$H), 1.79-0.88 (m, 18H, pentyl); $^{13}$C NMR (75 MHz, CDCl$_3$) δ 178.72 (C=O), 172.28 (C=O), 156.11, 149.22, 148.36, 137.28, 134.84, 133.90, 132.71, 131.07, 129.54, 129.10, 128.61, 123.34, 118.84, 113.54, 112.30, 111.82, 70.05, 69.33, 68.77, 40.24, 28.89, 28.18, 22.46, 14.03; IR (KBr) 3550 (OH), 2950, 2925, 1700 (C=O), 1570, 1530, 1250 cm$^{-1}$; MS (DCI) m/e 535 (MH+), 517 (M—OH), 273, 263, 255. Anal. Calcd for C$_{32}$H$_{38}$O$_7$.0.75 H$_2$O: C, 78.05; H, 7.27. Found: C, 71.09; H, 7.07.

For 2-[(3,4-biscyclopentyloxy)phenyl]methoxy-3'-carboxy-[1,1'-biphenyl]-6-acetic acid (30b): scale=0.456 mmol, yield=65%; chromatographed on reverse-phase C-18 silica gel using methanol; mp=146°-148° C.; UV$_{max}$ (EtOH) 206 nm ($\epsilon$=61550), 282 nm ($\epsilon$=5781); $^1$H NMR (300 MHz, CDCl$_3$) δ 8.04 (d, J=8 Hz, 1H, ArH), 8.01 (s, 1H, ArH), 7.54–7.45 (m, 2H, ArH), 7.34 (dd, J=8, 8 Hz, 1H, ArH), 7.03 (d, J=8 Hz, 1H, ArH), 6.98 (d, J=8 Hz, 1H, ArH), 6.76 (d, J=8 Hz, 1H, ArH), 6.66 (d, J=8 Hz, 1H, ArH), 6.61 (s, 1H, ArH), 4.94 (s, 2H, ArCH$_2$O), 4.67–4.48 (m, 2H, 2×R$_2$CHOR), 3.47 (s, ArCH$_2$CO$_2$), 1.80–1.54 (m, 16H, cyclopentyl); $^{13}$C NMR (75 MHz, CDCl$_3$) δ 178.71 (C=O ), 172.26 (C=O), 156.11, 148.88, 148.23, 137.26, 134.85, 130.90, 132.64, 131.04, 129.71, 129.12, 129.10, 128.60, 123.31, 3.19.16, 116.57, 114.97, 112.27, 111.47, 81.13, 80.56, 70.02, 40.21, 32.69, 23.87; IR (KBr) 3400 (OH), 2950, 2840, 1690 (C=O), 1580, 1510, 1260 cm$^{-1}$; MS (DCI) m/e 531 (MH+), 530 (M+), 509, 445 (M—C$_5$H$_9$O), 395, 273, 255. Anal. Calcd for C$_{32}$H$_{34}$O$_7$.1.5 H$_2$O: C, 68.93; H, 6.50. Found: C, 69.02; H, 6.10.

For 3'-carboxy-2-[4-decyloxyphenyl]methoxy-[1,1'-biphenyl]-6-acetic acid (30c): scale=0.598 mmol, yield=69%; chromatographed on silica gel using CH$_2$Cl$_2$, then 10% methanol/CH$_2$Cl$_2$: mp=130°–131° C.; UV$_{max}$ (EtOH) 204 nm ($\epsilon$=39538), 224 nm ($\epsilon$=31401), 280 nm ($\epsilon$=4138); $^1$H NMR (300 MHz, CDCl$_3$) δ 8.03 (d, J=8 Hz, 1H, ArH), 8.00 (s, 1H, ArH), 7.55–7.45 (m, 2H, ArH), 7.34 (dd, J=8, 8 Hz, 1H, ArH), 7.05 (d, J=8 Hz, 1H, ArH), 7.02–6.94 (m, 3H, ArH), 6.67 (d, J=8 Hz, 1H, ArH), 6.57 (s, 1H, ArH), 4.98 (s, 2H, ArCH$_2$O), 3.90 (t, J=7 Hz, 2H, ArOCH$_2$R), 3.36 (s, 2H, ArCH$_2$CO$_2$), 1.80–1.67 (m, 2H, OCH$_2$CH$_2$R), 1.51–1.20 (m, 14H, R (CH$_2$)$_7$CH$_3$), 0.90 (t, J=7 Hz, 3H, CH$_3$C); $^{13}$C NMR (75 MHz, CDCl$_3$) δ 178.20 (C=O), 172.19 (C=O), 158.66, 156.21, 137.10, 134.80, 133.90, 132.72, 131.26, 129.20, 129.06, 128.98, 128.84, 128.71, 128.59, 128.19, 123.32, 114.55, 114.33, 112.51, 70.20, 65.09, 40.09, 31.88, 29.55, 29.39, 29.31, 29.24, 26.16, 22.67, 14.11; IR (KBr) 3400 (OH), 2950, 2850, 1710 (C=O), 1690 (C=O), 1580, 1510, 1250 cm$^{-1}$; MS (DCI) m/e 510 (M+), 273, 255, 247. Anal. Calcd for C$_{32}$H$_{38}$O$_6$.H$_2$O: C, 71.62; H, 7.51. Found: C, 71.84; H, 7.26.

Example 21: Synthesis of Diacid 30d

Alcohol 12g (1.00 g., 3.68 mmol, 1 equiv.; from Example 10) is dissolved in 7 mL of dimethylformamide. Collidine (0.530 g., 4.40 mmol, 1.2 equiv.) and lithium chloride (0.336 g., 8.00 mmol, 2.17 equiv.) are then added. The mixture is then cooled to 0° C. and mesyl chloride (0.506 g., 4.40 mmol, 1.2 equiv.) is added dropwise. The mixture is allowed to warm to room temperature and stirred 1.5 hours. The reaction mixture is partitioned between water and EtOAc. The aqueous phase is extracted twice with EtOAc, and the combined extracts are washed with water, 10% aqueous CuSO$_4$ solution and then brine. The organic phase is dried (MgSO$_4$), and concentrated to afford 4-[1-adamantyl]-3-methoxybenzyl chloride (1.00 g., 3.45 mmol, 94%): mp=77°–78° C.; $^1$H NMR (300 MHz, CDCl$_3$) δ 7.24 (d, J=7 Hz, 1H, ArH), 6.97 (d, J=7 Hz, 1H, ArH), 6.94 (s, 1H, ArH), 4.60 (s, 2H, ArCH$_2$Cl), 3.88 (s, 3H, OCH$_3$), 2.12 (s, 9H, adamantyl), 1.81 (s, 6H, adamantyl); $^{13}$C NMR (75 MHz, CDCl$_3$) δ 159.05, 138.93, 136.04, 126.86, 120.61, 111.80, 55.01, 46.38, 40.59, 37.19, 29.17.

To all of the above benzyl chloride in acetone (30 mL) is added sodium iodide (1.70 g., 10.0 mmol, 2.90 equiv.) and potassium carbonate (0.450 g., 10.5 mmol, 3.04 equiv.). The mixture is allowed to stir for 18 hours at room temperature. The solvents are evaporated, and the residue extracted twice with EtOAc. The extracts are washed with water and then brine. The organic phase is dried (MgSO$_4$), and concentrated to afford 4-[1-adamantyl]-3-methoxybenzyl iodide (18b) (1.10 g., 2.88 mmol, 84%): mp=143°–144° C.; $^1$H NMR (300 MHz, CDCl$_3$) δ 7.25 (d, J=7 Hz, 1H, ArH), 6.95 (d, J=7 Hz, 1H, ArH), 6.85 (s, 1H, ArH), 4.46 (s, 2H, ArCH$_2$I), 3.85 (s, 3H, OCH$_3$), 2.07 (s, 9H, adamantyl), 1.77 (s, 6H, adamantyl) .

Phenol 25 (0.656 g., 2.00 mmol, 1 equiv.; from Example 18) is dissolved in 15 mL of methyl isobutyl ketone. 4-[1-Adamantyl]-3-methoxybenzyl iodide (18b) (0.766 g., 2.00 mmol, 1 equiv.) and potassium carbonate (1.00 g., 7.2 mmol, 3.6 equiv.) are added and the mixture is heated to reflux for 5 hours. The solvents are evaporated and the residue is dissolved in methylene chloride. This solution is washed with water and brine, then dried (MgSO$_4$), and concentrated. The crude material is chromatographed on silica gel using 50% CH$_2$Cl$_2$/hexane to afford 3'-carboethoxy-2-[4-(1-adamantyl)-3-methoxyphenyl]methoxy-[1,1'-biphenyl]-6-acetic acid, ethyl ester (29d) (0.725 g., 1.24 mmol, 62%): $^1$H NMR (300 MHz, CDCl$_3$) δ 8.06 (dd, J=2, 8 Hz, 1H, ArH), 7.98 (s, 1H, ArH), 7.50–7.47 (m, 2H, ArH), 7.33–6.97 (m, 4H, ArH), 6.69 (dd, J=2, 8 Hz, 1H, ArH), 6.57 (d, J=2 Hz, 1H, ArH), 4.97 (s, 2H, ArCH$_2$O), 4.38 (q, J=7 Hz, 2H, CO$_2$CH$_2$), 4.03 (q, J=7 Hz, 2H, CO$_2$CH$_2$), 3.59 (s, 3H, CH$_3$O), 3.41 (s, 2H, ArCH$_2$CO$_2$), 2.03 (s, 9H, adamantyl), 1.75 (s, 6H, adamantyl), 1.40 (t, J=7 Hz, 3H, CO$_2$CH$_2$CH$_3$), 1.16 J=7 Hz, 3 Hz, CO$_2$CH$_2$CH$_3$); $^{13}$C NMR (75 MHz, CDCl$_3$) δ 171.48 (C=O), 166.54 (C=O), 158.84, 156.13, 137.62, 137.33, 135.74, 134.91, 134.21, 131.31, 131.05, 130.44, 128.82, 128.33, 128.14, 126.27, 122.82, 118.09, 111.49, 109.54, 69.75, 60.97, 60.77, 54.82, 40.55, 39.23, 37.13, 36.80, 29.09, 14.38, 14.12.

3'-Carboethoxy-2-[4-(1-adamantyl)-3-methoxyphenyl]methoxy-[1,1'-biphenyl]-6-acetic acid, ethyl ester (29d) (0.510 g., 0.87 mmol) is hydrolyzed according to the general procedure of Example 7 (heat to reflux 5 hours) to yield 3'-carboxy-2-[4-(1-adamantyl)-3-methoxyphenyl]methoxy-[1,1'-biphenyl]-6-acetic acid (30d) (0.368 g., 0.700 mmol, 81%): chromatographed on silica gel using 10% MeOH/CH$_2$Cl$_2$: mp=240°–242° C.; UV$_{max}$ (EtOH) 206 nm ($\epsilon$=47130), 280 nm ($\epsilon$=3760); $^1$H NMR (300 MHz, CDCl$_3$) δ 8.03 (d, J=8 Hz, 1H, ArH) , 8.01 (s, 1H, ArH), 7.55–7.45 (m, 2H, ArH), 7.34 (dd, J=8, 8 Hz, 1H, ArH), 7.05 (d, J=8 Hz, 1H, ArH), 7.00 (d, J=8 Hz, 1H, ArH), 6.94 (d, J=8 Hz, 1H, ArH) , 6.65 (d, J=8 Hz, 1H, ArH), 6.56 (s, 1H, ArH) , 4.99 (s, 2H, ArCH$_2$O), 3.55 (s, 3H, CH$_3$O), 3.47 (s, 2H, ArCH$_2$CO$_2$), 1.99 (s, 9H, adamantyl ) , 1.71 ( s, 6H, adamantyl); $^{13}$C NMR (75 MHz, CDCl$_3$) δ 173.73 (C=O), 168.55 (C=O ), 158.76, 155.95, 137.44, 137.20, 135.73, 134.69, 134.46, 131.57, 130.66, 128.61, 128.43, 127.99, 126.14, 122.88, 118.01, 111.25, 109.48, 69.62, 54.83, 40.45, 40.23, 39.95, 39.67, 38.88, 37.03, 36.68, 28.96; IR (KBr) 3400 (OH), 2920, 1720 (C=O), 1680 (C=O), 1560, 1523, 1250 cm$^{-1}$; MS (DCI) m/e 527 (M+), 255. Anal. Calcd for C$_{33}$H$_{34}$O$_6$.1.33 H$_2$O: C, 71.98; H, 6.70. Found: C, 71.89; H, 6.29.

Example 22: Synthesis of Diacids 30e–f 2-(5,5,8,8-Tetramethyl-5,6,7,8-tetrahydro-2-naphthalenyl)methoxy-1,1'-biphenyl-6-acetaldehyde (32e, from Example 16) is oxidized according to the method of Example 4 to afford 2-(5,6,7,8-tetrahydro-5,5,8,8-tetramethyl-2-naphthalenyl)methoxy-[1,1'-biphenyl]-6-acetic acid (30e) (0.252 g., 0.59 mmol, 67% yield for two steps from 0.377 g. of 31e (see Example 16)): chromatographed on silica gel using 5% MeOH/$CH_2Cl_2$ to afford a white solid; $UV_{max}$ (MeOH) 206 nm ($\epsilon=44379$), 276 nm ($\epsilon=2540$); $^1H$ NMR (300 MHz, $CD_3OD$) δ 7.43–7.32 (m, 3H, ArH), 7.30–7.15 (m, 4H, ArH), 7.04 (m, 2H, ArH), 6.96 (d, J=8 Hz, 1H, ArH), 6.88 (dd, J=2, 8 Hz, 1H, ArH), 4.91 (s, 2H, $ArCH_2O$), 3.37 ( s, 2H, $ArCH_2CO_2$), 1.63 (s, 4H, $CH_2CH_2$), 1.21 ( s, 6H, 2×$CH_3$), 1.12 (s, 6H, 2×$CH_3$); $^{13}C$ NMR (75 MHz, $CD_3OD$) δ 175.71 (C=O), 157.46, 145.74, 144.95, 138.55, 135.64, 135.60, 133.67, 131.29, 130.93, 129.35, 129.14, 128.11, 127.31, 125.84, 125.05, 124.05, 114.21, 112.83, 71.17, 39.65, 36.25, 36.20, 35.16, 34.96, 32.25; IR (KBr) 3422, 2960, 2926, 1710, 1456, 1258, 1068, 702 $cm^{-1}$; MS (DCI) m/e 429 ($MH^+$), 428 ($M^+$), 411 (M—OH), 201 ($C_{15}H_{21}^+$). Anal. Calcd for $C_{29}H_{32}O_3.0.6\ H_2O$: C, 79.27; H, 7.62. Found: C, 79.28; H, 7.44.

2-(5,6,7,8-Tetrahydro-5,5,8,8-tetramethyl-2-naphthalenyl)methoxy-3'-carboethoxy-1,1'-biphenyl-6-acetaldehyde (32f, from Example 15) is oxidized according to the method of Example 4 to afford 3'-carboethoxy-2-(5,6,7,8-tetrahydro-5,5,8,8-tetramethyl-2-naphthalenyl)methoxy-[1,1'-biphenyl]-6-acetic acid (0.244 g., 0.49 mmol, 48% yield for two steps from 0.506 g. of 31f, see Example 15)): chromatographed on silica gel using 35% EtOAc/hexane; $UV_{max}$ ($CHCl_3$) 242 nm ($\epsilon=8586$), 278 nm ($\epsilon=3144$); $^1H$ NMR (300 MHz, $CDCl_3$) δ 8.04 (m, 1H, ArH), 7.96 (s, 1H, ArH), 7.46 (m, 2H, ArH), 7.32 (dd, J=8, 8 Hz, 1H, ArH), 7.16 (d, J=8 Hz, 1H, ArH), 6.98 (m, 3H, ArH), 6.87 (dd, J=2, 8 Hz, 1H, ArH), 4.92 (s, 2H, $ArCH_2O$), 4.31 (q, J=7 Hz, 2H, $CO_2CH_2$), 3.44 (s, 2H, $ArCH_2CO_2$), 1.60 (s, 4H, $CH_2CH_2$), 1.32 (t, J=7 Hz, 3H, $CO_2CH_2CH_3$), 1.20 (s, 6H, 2×$CH_3$), 1.08 (s, 6H, 2×$CH_3$); $^{13}C$ NMR (75 MHz, $CDCl_3$) δ 176.98 (C=O), 166.53 (C=O), 156.30, 144.83, 144.09, 136.92, 134.77, 133.81, 133.26, 131.20, 130.45, 128.83, 128.56, 128.27, 126.39, 124.47, 123.65, 122.63, 111.62, 70.02, 60.93, 38.54, 34.99, 34.14, 34.04, 31.80, 31.66, 14.27; IR (film) 3240, 2960, 2926, 1716, 1456, 1298, 1258, 1232, 758 $cm^{-1}$; MS (DCI) m/e 501 ($MH^+$), 483 (M—OH), 455 (M—$C_2H_5O$), 201 ($C_{15}H_{21}^+$).

3'-Carboethoxy-2-(5,6,7,8-tetrahydro-5,5,8,8-tetramethyl-2-naphthalenyl)methoxy-[1,1'-biphenyl]-6-acetic acid as obtained above (0.207 g., 0.414 mmol) is hydrolyzed via the method of Example 7 to yield 3'-carboxy-2-(5,6,7,8-tetrahydro-5,5,8,8-tetramethyl-2-naphthalenyl)methoxy-[1,1'-biphenyl]-6-acetic acid (30f) (0.167 g., 0.354 mmol, 85%) as a white foam: chromatographed on reverse-phase C-18 silica gel using methanol; $UV_{max}$ ($CHCl_3$) 242 nm ($\epsilon=9965$), 278 nm ($\epsilon=3435$); $^1H$ NMR (300 MHz, $CDCl_3$) δ8.02 (m, 2H, ArH), 7.51 (dd, J=8, 8 Hz, 1H, ArH), 7.46 (ddd, J=2, 2, 8 Hz, 1H, ArH), 7.33 (dd, J=8, 8 Hz, 1H, ArH), 7.14 (d, J=8 Hz, 1H, ArH), 7.02 (d, J=8 Hz, 1H, ArH), 6.96 (d, J=8 Hz, 1H, ArH), 6.93 (s, iH, ArH), 6.85 (dd, J=2, 8 Hz, 1H, ArH), 4.94 (m, 2H, $ArCH_2O$), 3.47 (s, 2H, $ArCH_2CO_2$), 1.57 (s, 4H, $CH_2CH_2$), 1.18 (s, 6H, 2×$CH_3$), 1.05 (s, 3H, $CH_3$), 1.03 (s, 3H, $CH_3$); $^{13}C$ NMR (75 MHz, $CDCl_3$) δ 178.77 (C=O), 172.37 (C=O), 156.30, 144.88, 144.13, 137.24, 134.77, 133.91, 133.76, 132.76, 131.08, 129.19, 129.11, 128.66, 126.38, 124.56, 123.65, 123.21, 69.94, 40.22, 34.95, 34.11, 34.02, 31.77, 31.60; IR (KBr) 3422, 2960, 2926, 1702, 1456, 1412, 1300, 1258 $cm^{-1}$; MS (DCI) m/e 473 ($MH^+$), 455 (M-OH), 201 ($C_{15}H_{21}^+$). Anal. Calcd for $C_{30}H_{32}O_5.0.33\ H_2O$: C, 75.29; H, 6.88. Found: C, 75.18; H, 6.74.

Experimental Procedures for Compounds of Type IC and Type ID

Example 23: Synthesis of Diacids 37a–c

2-Methoxy-3'-carboethoxy-[1,1'-biphenyl]-6-carboxaldehyde (4a) (0.852 g., 3.00 mmol, 1 equiv.) is dissolved in 10 mL of toluene, and methyl diethylphosphonoacetate (0.840 g., 4.00 mmol, 1.33 equiv.) is added. A solution of 25% by weight sodium methoxide in methanol (1.62 g., 7.50 mmol, 2.5 equiv.) is added and the mixture stirred at room temperature for 18 hours. The mixture is partitioned between saturated aqueous ammonium chloride solution and ethyl acetate. The aqueous phase is extracted twice with ethyl acetate, and the combined extracts are washed with water and brine. The organic phase is dried ($MgSO_4$), and evaporated. The crude material is chromatographed on silica gel using $CH_2Cl_2$/hexane to afford (E) and (Z) 2-methoxy-6-[methyl(3-propenoate)]-1,1'-biphenyl-3'-carboxylic acid, methyl ester (33) (0.650 g., 2.01 mmol, 67%) as a >10:1 mixture of E:Z isomers: Data for E isomer: $^1H$ NMR (300 MHz, $CDCl_3$) δ 8.05 (m, 1H, ArH), 7.93 (s, 1H, ArH), 7.51–7.32 (m, 5H, ArH and C=CH), 7.00 (d, J=8 Hz, 1H, ArH), 6.31 (d, J=16 Hz, 1H, C=CH), 3.90 (s, 3H, $OCH_3$), 3.71 (s, 3H, $CO_2CH_3$), 3.68 (s, 3H, $CO_2CH_3$); $^{13}C$ NMR (75 MHz, $CDCl_3$) δ 167.01 (C=O), 157.04, 143.06, 135.81, 135.23, 134.53, 131.83, 130.81, 129.99, 128.92, 128.71, 128.16, 119.46, 118.66, 112.06, 55.86, 52.05, 51.59.

(E) and (Z) 2-methoxy-6-[methyl(3-propenoate)]-1,1'-biphenyl-3'-carboxylic acid, methyl ester (33) (2.40 g., 7.06 mmol, 1 equiv.; >10:1 mixture of E:Z isomers) is dissolved in 50 mL of ethanol and 10% palladium on carbon (0.360 g., 0.338 mmol, 5 mol %) is added. The suspension is hydrogenated at 50 psi for 4 hours. An aliquot was taken, and the reaction judged to be only 30% complete by NMR analysis. More catalyst (0.180 g., 0.169 mmol, 2.5 mol %) is added, and hydrogenation continued for another 18 hours. The analysis of an aliquot at this time indicates the reaction is only 75% complete, and another portion of catalyst (0.200 g., 0.188 mmol, 2.8 mol %) is added. After a further 5 hours of hydrogenation, the reduction was complete. The suspension is filtered through celite, and the filter cake washed with ethanol. The filtrate is evaporated to dryness, and the residue filtered through a pad of silica gel using $CH_2Cl_2$ to afford 2-methoxy-6-[methyl(3-propanoate)]-1,1'-biphenyl-3'-carboxylic acid, methyl ester (34) (2.10 g., 6.14 mmol, 87%): $UV_{max}$ (EtOH) 206 nm ($\epsilon=32090$), 280 nm ($\epsilon=3164$); $^1H$ NMR (300 MHz, $CDCl_3$) δ 8.09 (d, J=8 Hz, 1H, ArH), 7.97 (s, 1H, ArH), 7.57–7.50 (m, 2H, ArH), 7.18 (d, J=8 Hz, 1H, ARH), 6.80 (m, 2H, ARH), 3.95 (s, 3H, $CO_2CH_3$), 3.70 (s, 3H, $CO_2CH_3$), 3.60 (s, 3H, $OCH_3$), 2.91 (t, J=7 Hz, 2H, $ArCH_2CH_2$), 2.37 (t, J=7 Hz, 2H, $CH_2CH_2CO_2$); $^{13}C$ NMR (75 MHz, $CDCl_3$) δ 173.12 (C=O), 167.13 (C=O), 156.97, 139.94, 137.30, 131.22, 131.13, 130.13, 129.73, 128.79, 128.27, 121.14, 108.87, 55.71, 52.09, 51.54, 34.94, 28.37; IR (KBr) 2950, 1740, 1720, 1589, 1470, 1300, 1260, 1235 cm$^{-1}$; MS (DCI) m/e 329 (MH$^+$), 311 (M-OH). Anal. Calcd for C$_{19}$H$_{20}$O$_5$: C, 69.50; H, 6.14. Found: C, 69.55; H, 6.28.

2-Methoxy-6-[methyl(3-propanoate)]-1,1'-biphenyl-3'-carboxylic acid, methyl ester (34) (2.90 g., 8.48 mmol) is demethylated via the method of Example 6 to afford 2-hydroxy-6-[methyl(3-propanoate)]-1,1'-biphenyl-3'-carboxylic acid, methyl ester (35) (2.10 g., 6.40 mmol, 76%): chromatographed on silica gel using CH$_2$Cl$_2$/hexane, then CH$_2$Cl$_2$, then 10% EtOAc/CH$_2$Cl$_2$; mp=98°-99° C.; UV$_{max}$ (mtOH) 206 nm ($\epsilon$=30901), 284 nm ($\epsilon$=3178); $^1$H NMR (300 MHz, CDCl$_3$) δ 8.10-6.80 (m, 7H, ArH), 4.77 (s, 1H, OH), 3.90 (s, 3H, CO$_2$CH$_3$), 3.56 (s, 3H, CO$_2$CH$_3$), 2.67 (t, J=8 Hz, 2H, ArCH$_2$CH$_2$), 2.36 (t, J=8 Hz, 2H, CH$_2$CH$_2$CO$_2$); $^{13}$C NMR (75 MHz, CDCl$_3$) δ 173.08 (C=O), 166.62 (C=O), 152.95, 139.61, 135.31, 134.94, 131.45, 131.26, 129.51, 129.25, 127.04, 120.86, 113.60, 52.31, 51.58, 34.84, 28.43; IR (KBr) 3410, 1750, 1700, 1580, 1465, 1320, 1280, 1270 cm$^{-1}$; MS (DCI) m/e 329 (MH$^+$), 315, 283. Anal. Calcd for C$_{18}$H$_{18}$O$_5$: C, 68.77; H, 5.77. Found: C, 68.39; H, 5.63.

Phenol 35 is coupled to alcohols 12b, 12d, and 12c (see Example 8) via the method of Example 11 to afford ethers 36a, 36b, and 36c, respectively.

For 2-[3,4-bis(3-methyl-2-butenyloxy)phenyl]methoxy-3'-carbomethoxy-[1,1'-biphenyl]-6-propanoic acid, methyl ester (36a): scale=2.22 mmol, yield=51%; chromatographed on silica gel using CH$_2$Cl$_2$/hexane, then CH$_2$Cl$_2$ to afford a clear oil; UV$_{max}$ (EtOH) 208 nm ($\epsilon$=59871), 280 nm ($\epsilon$=4832); $^1$H NMR (300 MHz, CDCl$_3$) δ 8.01 (ddd, J=2, 2, 8 Hz, 1H, ArH), 7.93 (d, J=2 Hz, 1H, ArH), 7.49 (d, J=8 Hz, 1H, ArH), 7.44 (s, 1H, ArH), 7.24 (d, J=8 Hz, 1H, ArH), 6.95 (d, J=8 Hz, 1H, ArH), 6.86 (d,J=8 Hz, 1H, ArH), 6.70 (d, J=8 Hz, 1H, ArH), 6.60 (m, 2H, ArH), 5.44 (m, 2H, 2×C=CH), 4.87 (s, 2H, ArCH$_2$O), 4.51 (d, 2H, J=7 Hz, OCH$_2$R), 4.33 (d, 2H, J=7 Hz, OCH$_2$R), 3.87 (s, 3H, CO$_2$CH$_3$), 3.56 (s, 3H, CO$_2$CH$_3$), 2.72 (t, 2H, ArCH$_2$CH$_2$), 2.36 (t, 2H, CH$_2$CO$_2$CH$_3$), 1.74 (s, 3H, CH$_3$), 1.72 (s, 3H, CH$_3$), 1.67 (s, 3H, CH$_3$), 1.64 (s, 3H, CH$_3$); $^{13}$C NMR (75 MHz, CDCl$_3$) δ 173.07 (C=O), 166.98 (C=O), 156.00, 148.83, 148.10, 139.98, 137.54, 137.46, 136.99, 134.78, 131.25, 130.50, 130.06, 129.70, 128.76, 128.16, 121.54, 120.33, 119.94, 118.95, 113.67, 112.20, 111.04, 96.10, 70.15, 66.02, 65.67, 52.04, 51.53, 34.92, 28.40, 25.78, 18.20; IR (KBr) 2920, 1740 (C=O), 1725 (C=O), 1510, 1440, 1260, 1230 cm$^{-1}$; MS (DCI) m/e 573 (MH$^+$), 572 (M), 315, 259. Anal. Calcd for C$_{35}$H$_{40}$O$_7$: C, 73.43; H, 6.99. Found: C, 73.10; H, 6.77.

For 2-[3,4-bis(cyclopentyloxy)phenyl]methoxy-3'-carbomethoxy-[1,1'-biphenyl]-6-propanoic acid, methyl ester (36b): scale=3.32 mmol, yield=53%; chromatographed on silica gel using CH$_2$Cl$_2$/hexane, then CH$_2$Cl$_2$ to afford a clear oil; UV$_{max}$ (EtOH) 208 nm ($\epsilon$=55184), 282 nm ($\epsilon$=4919); $^1$H NMR (300 MHz, CDCl$_3$) δ 8.04 (d, 1H, J=8 Hz, ArH), 7.98 (s, 1H, ArH), 7.51 (d, J=8 Hz, 1H, ArH), 7.46 (s, 1H, ArH), 7.27 (d, J=8 Hz, 1H, ArH), 6.89 (d, J=8 Hz, 1H, ArH), 6.86 (d, J=8 Hz, 1H, ArH), 6.77 (d, J=8 Hz, 1H, ArH), 6.64 (d, J=8 Hz, 1H, ArH), 6.60 (s, 1H, ArH), 4.90 (s, 2H, ArCH$_2$O), 4.69 (m, 1H, R$_2$CHOR), 4.45 (m, 1H, R$_2$CHOR), 3.91 (s, 3H, CO$_2$CH$_3$), 3.59 (s, 3H, CO$_2$CH$_3$), 1.81-1.58 (m, 16H, cyclopentyl), 2.75 (t, J=8 Hz, 2H, ArCH$_2$CH$_2$), 2.39 (t, J=8 Hz, 2H, CH$_2$CO$_2$CH$_3$); $^{13}$C NMR (75 MHz, CDCl$_3$) δ 173.03 (C=O), 166.96 (C=O), 155.99, 148.86, 148.20, 139.98, 137.53, 134.85, 131.23, 130.42, 129.90, 128.78, 128.18, 121.47, 119.14, 116.2, 115.03, 110.88, 81.06, 80.67, 69.98, 52.04, 51.50, 34.92, 32.89, 28.41, 24.06; IR (KBr) 2960, 1740 (C=O), 1725 (C=O), 1580, 1508, 1435, 1260, 1220 cm$^{-1}$; MS (DCI) m/e 573 (MH$^+$), 572 (M), 517, 505, 259. Anal. Calcd for C$_{35}$H$_{40}$O$_7$: C, 73.43; H, 6.99. Found: C, 73.07; H, 6.70.

For 2-[3,4-bis(pentyloxy)phenyl]methoxy-3'-carbomethoxy-[1,1'-biphenyl]-6-propanoic acid, methyl ester (36c): scale=1.31 mmol, yield=66%; chromatographed on silica gel using CH$_2$Cl$_2$/hexane to afford a clear oil; UV$_{max}$ (EtOH) 206 nm ($\epsilon$=52865), 280 nm ($\epsilon$=4838); $^1$H NMR (300 MHz, CDCl$_3$) δ 8.06 (ddd, J=2, 2, 8 Hz, 1H, ArH), 7.94 (d, J=2 Hz, 1H, ArH), 7.45-6.90 (m, 5H, ArH), 6.70 (dd, J=2, 8 Hz, 1H, ArH), 6.62 (dd, J=2, 8 Hz, 1H, ArH), 6.55 (d, J=2 Hz, 1H, ArH), 4.87 (s, 2H, ArCH$_2$O), 3.95 (t, J=7 Hz, 2H, ArOCH$_2$R), 3.70 (t, J=7 Hz, 2H, ArOCH$_2$R), 3.90 (s, 3H, CO$_2$CH$_3$), 3.57 (s, 3H, CO$_2$CH$_3$), 2.72 (t, J=7 Hz, 2H, ArCH$_2$CH$_2$), 2.34 (t, J=7 Hz, 2H, CH$_2$CO$_2$CH$_3$), 1.80-0.87 (m, 18H, pentyl); $^{13}$C NMR (75 MHz, CDCl$_3$) δ 173.09 (C=O), 166.99 (C=O), 155.98, 149.13, 148.32, 139.98, 137.51, 134.80, 131.25, 130.49, 130.05, 129.71, 128.77, 128.17, 121.51, 118.79, 113.50, 111.91, 110.96, 70.04, 69.31, 68.84, 52.06, 51.55, 34.92, 28.98, 28.93, 28.39, 28.28, 22.51, 14.08; IR (KBr) 2950, 1740 (C=O), 1730 (C=O), 1580, 1530, 1425, 1250, 1235 cm$^{-1}$; MS (DCI) m/e 577 (MH$^+$), 576 (M), 575, 263. Anal. Calcd for C$_{35}$H$_{44}$O$_7$: C, 72.92; H, 7.64. Found: C, 72.61; H, 7.35.

Esters 36a-c are hydrolyzed via the method of Example 7 to afford diacids 37a-c.

For 2-[3,4-bis(3-methyl-2-butenyloxy)phenyl]methoxy-3'-carboxy-[1,1'-biphenyl]-6-propanoic acid (37a): scale=1.66 mmol, yield=83%; chromatographed on reverse-phase C-18 silica gel using methanol to afford a white solid; mp=142°-143° C.; UV$_{max}$ (EtOH) 208 nm ($\epsilon$=58708), 280 nm ($\epsilon$=4999); $^1$H NMR (300 MHz, CDCl$_3$) δ 8.02 (m, 2H, ArH), 7.48 (m, 2H, ArH), 7.28 (d, J=8 Hz, 1H, ArH), 6.95 (d, J=8 Hz, 1H, ArH), 6.92 (d, J=8 Hz, 1H, ArH), 6.75 (d, J=8 Hz, 1H, ArH), 6.65 (m, 2H, ArH), 5.41 (m, 2H, OCH$_2$CH=C), 4.88 (s, 2H, ArCH$_2$O), 4.51 (d, J=6 Hz, 2H, O—CH$_2$C=C), 4.33 (d, J=6 Hz, 2H, O—CH$_2$C=C), 2.71 (m, 2H, ArCH$_2$CH$_2$) 2.45 (m, 2H, ArCH$_2$CO$_2$), 1.71 (s, 6H, 2×CH$_3$), 1.66 (s, 6H, 2×CH$_3$). $^{13}$C NMR (75 MHz, CDCl$_3$) δ 179.29 (C=O), 172.29 (C=O), 156.02, 148.86, 148.12, 139.75, 137.64, 137.49, 137.03, 135.79, 131.97, 130.45, 129.67, 129.19, 8.91, 128.83, 128.21, 121.36, 120.31, 119.83, 118.97, 113.75, 112.22, 111.06, 70.18, 66.06, 65.61, 35.12, 27.92, 25.79, 25.75, 18.18; IR (KBr) 3430 (OH), 3540 (OH), 2900, 1680, (C=O), 1580, 1510, 1260 cm$^{-1}$; MS (DCI) m/e 545 (MH$^+$), 537, 527, 289, 269, 259. Anal. Calcd for C$_{33}$H$_{36}$O$_7$.H$_2$O: C, 70.33; H, 6.51. Found: C, 70.44; H, 6.80.

For 2-[3,4-bis(cyclopentyloxy)phenyl]methoxy-3'-carboxy-[1,1'-biphenyl]-6-propanoic acid (37b): scale=1.14 mmol, yield=90%; chromatographed on reverse-phase C-18 silica gel using methanol to afford a white solid; mp=148°-150° C.; UV$_{max}$ (EtOH) 208 nm ($\epsilon$=55091), 280 nm ($\epsilon$=4755); $^1$H NMR (300 MHz, CDCl$_3$) δ 8.03 (m, 2H, ArH), 7.46-7.27 (m, 3H, ArH), 6.90 (d, J=8 Hz, 1H, ArH), 6.87 (d, J=8 Hz, 1H, ArH), 6.74 (d, J=6 Hz, 1H, ArH), 6.25 (dd, J=2, 8 Hz, 1H, ArH), 6.57 (d, J=2 Hz, 1H, ArH), 4.87 (s, 2H, ArCH$_2$O), 4.65-4.48 (m, 2H, 2×R$_2$CHOAr), 2.75 (m, 2 H, ArCH$_2$CH$_2$), 2.46 (m, 2H, ArCH$_2$CH$_2$CO$_2$), 1.78-1.54

(m, 16H, cyclopetyl); $^{13}$C NMR (75 MHz, CDCl$_3$) δ 179.44 (C=O), 172.46 (C=O), 156.13, 149.02, 148.35, 139.88, 137.65, 135.96, 132.13, 130.51, 129.99, 129.27, 129.03, 128.91, 128.35, 121.40, 119.32, 116.72, 115.20, 111.03, 81.28, 80.89, 70.17, 35.23, 32.89, 28.02, 24.02, 23.96; IR (KBr) 3450 (OH), 2960, 1700 (C=O), 1430, 1265 cm$^{-1}$; MS (DCI) m/e 545 (MH+), 544 (M+), 527 (M—H$_2$O), 269, 259. Anal. Calcd for C$_{33}$H$_{36}$O$_7$.0.10 H$_2$O: C, 72.53; H, 6.80. Found: C, 72.32; H, 6.73.

For 2-[3,4-bis (pentyloxy)phenyl]methoxy-3'-carboxy-[1,1'-biphenyl]-6-propanoic acid (37c): scale=0.784 mmol, yield=66%; chromatographed on reverse-phase C-18 silica gel using methanol to afford a white solid; mp=145°-146° C.; UV$_{max}$ (EtOH) 206 nm (ε=59315), 280 nm (ε=4818); $^1$H NMR (300 MHz, CDCl$_3$) δ 8.02 (m, 2H, ArH), 7.50 (m, 2H, ArH), 7.27 (m, 1H, ArH), 6.95-6.55 (m, 5H, ArH), 4.88 (s, 2H, ArCH$_2$O), 3.90 (t, J=6 Hz, 2H, ArOCH$_2$), 3.72, (t, J=6 Hz, 2 H, ArOCH$_2$), 2.71 (m, 2H, ArCH$_2$CH$_2$), 2.49 (m, 2H, ArCH$_2$CH$_2$CO$_2$), 1.80-0.86 (m, 18H, pentyl); $^{13}$C NMR (75 MHz, CDCl$_3$) δ 179.33 (C=0), 172.33 (C=0), 155.98, 149.18, 148.35, 139.75, 137.53, 135.81, 132.07, 130.45, 129.68, 129.14, 128.91, 128.77, 128.19, 121.31, 118.84, 113.57, 111.93, 110.94, 70.05, 69.34, 68.86, 35.15, 28.97, 28.91, 28.25, 28.18, 27.85, 22.46, 14.03; IR (KBr) 3450 (OH), 2950, 2860, 1700 (C=0), 1270 cm$^{-1}$; MS (DCI) m/e (M+−17), 531, 269, 263. Anal. Calcd for C$_{33}$H$_{40}$O$_7$.0.25 H$_2$O: C, 71.65; H, 7.38. Found: C, 71.49, H, 7.17.

Example 24: Synthesis Of Diacids 37d and 39d

Aldehyde 16 l (0.965 g., 2.05 mmol, 1 equiv.; from Example 13) is dissolved in 15.6 mL of CH$_2$Cl$_2$, and methyl (triphenylphos-phoranylidene)acetane (2.74 g., 8.20 mmol, 4 equiv.) is added. The mixture is stirred at room temperature for 24 hours. Thin-layer chromatographic analysis at this time indicates the reaction is incomplete. More methyl (triphenylphosphoranylidene)acetate (0.246 g., 0.736 mmol, 0.36 equiv.) is added and stirring continued for another 20 hours. The mixture is poured into water and EtOAc, and the aqueous phase is extracted with EtOAc. The combined extracts are washed with brine, dried (MgSO$_4$), and concentrated. The crude material is chromatographed using EtOAc/hexane (5%-10%-20%) to afford 3'-carboethoxy-2-[5,6,7,8-tetrahydro-5,5,8,8-tetramethyl-2-naphthalenyl]methoxy-[1,1'-biphenyl]-6-[(E)-3-propenoic acid], methyl ester (38d) (0.694 g., 1.32 mmol, 64%) as a clear oil: UV$_{max}$ (CHCl$_3$) 242 nm (ε =31760), 286 nm (ε=23380), 656 nm (ε=4992); $^1$H NMR (300 MHz, CDCl$_3$) δ 8.06 (ddd, J=2, 2, 8 Hz, 1H, ArH), 7.98 (dd, J=2, 2 Hz, 1H, ArH), 7.50 (dd, J=8, 8 Hz, 1H, ArH), 7.43 (m, 1H, ArH), 7.41 (d, J=16 Hz, 1H, C=CH), 7.33 (m, 2H, ArH), 7.17 (d, J=8 Hz, 1H, ArH), 7.06 (dd, J=2, 8 Hz, 1H, ArH), 7.00 (d, J=2 Hz, 1H, ArH), 6.90 (dd, J=2, 8 Hz, 1H, ArH), 6.32 (d, J=16 Hz, 1H, C=CH), 4.95 (s, 2H, ArCH$_2$O), 4.34 (q, J=7 Hz, 2H, CO$_2$CH$_2$), 3.68 (s, 3H, CO$_2$CH$_3$), 1.61 (s, 4H, CH$_2$CH$_2$), 1.35 (t, J=7 Hz, 3H, CO$_2$CH$_2$CH$_3$), 1.21 (s, 6H, 2×CH$_3$), 1.10 (s, 6H, 2×CH$_3$); $^{13}$C NMR (75 MHz, CDCl$_3$) δ 167.07 (C=O), 166.48 (C=O), 156.27, 144.89, 144.23, 143.37, 143.09, 135.93, 135.15, 134.66, 133.58, 131.79, 131.63, 130.35, 128.89, 128.78, 128.16, 126.47, 124.52, 123.73, 119.44, 118.95, 113.90, 70.28, 60.94, 51.61, 34.98, 34.16, 34.06, 31.80, 31.68, 14.33; IR (film) 2958, 2928, 1720, 1636, 1570, 1460, 1294, 1258, 1230, 1170 cm$^{-1}$; MS (DCI) m/e 527 (MH+), 495 (M-CH$_3$O), 481 (M-C$_2$H$_5$O), 201 (C$_{15}$H$_{21}$+). HRMS (FAB) Calcd for C$_{34}$H$_{38}$O$_5$Na: 549.2617. Found: 549.2611.

3'-Carboethoxy-2-[5,6,7,8-tetrahydro-5,5,8,8-tetramethyl-2-naphthalenyl]methoxy-[1,1'-biphenyl]-6-[(E)-3-propenoic acid], methyl ester (38d) (0.246 g., 0.467 mmol) is hydrolyzed via the method of Example 7 to afford 3'-carboxy-2-[5,6,7,8-tetrahydo-5,5,8,8-tetramethyl-2-naphthalenyl]methoxy-[1,1'-biphenyl]-6-[(E)-3-propenoic acid] (39d) (0.194 g., 0.401 mmol, 86%) as a white solid: recrystallized from EtOAc/hexane; mp=247°-249° C.; UV$_{max}$ (EtOH) 204 nm (ε=34000), 220 nm (ε=30186), 280 nm (ε=15343); $^1$H NMR (300 MHz, DMSO-d$_6$) δ 12.70 (b, 2H, 2×CO$_2$H), 7.97 (bd, J=8 Hz, 1H, ArH), 7.79 (s, 1H, ArH), 7.61-7.40 (m, 4H, ArH), 7.27 (d, J=8 Hz, 1H, ArH), 7.19 (d, J=8 Hz 1H, ArH), 7.15 (d, J=16 Hz, 1H, C=CH), 7.03 (s, 1H, ArH), 6.94 (d, J=8 Hz, 1H, ArH), 6.42 (d, J=16 Hz, 1H, C=CH), 5.00 (s, 2H, ArCH$_2$O), 1.56 (s, 4H, CH$_2$CH$_2$), 1.16 (s, 6H, 2×CH$_3$), 1.06 (s, 6H, 2×CH$_3$); $^{13}$C NMR (75 MHz, DMSO-d$_6$) δ 167.26 (C=0), 167.14 (C=0), 155.67, 144.20, 143.55, 141.43, 135.90, 134.94, 133.73, 133.65, 131.23, 130.70, 129.25, 128.48, 128.40, 126.15, 124.49, 124.12, 120.61, 118.81, 114.16, 69.43, 34.51, 33.74, 33.70, 31.56, 31.46; IR (KBr) 3422, 2962, 2926, 1688, 1626, 1570, 1464, 1310, 1254 cm$^{-1}$; MS (DCI) m/e 467 (M-OH), 201 (C$_{15}$H$_{21}$+). Anal. Calcd for C$_{31}$H$_{32}$O$_5$.0.75 H$_2$O: C, 74.75; H, 6.78. Found: C, 74.71; H, 6.64.

3'-Carboethoxy-2-[5,6,7,8-tetrahydro-5,5,8,8-tetramethyl-2-naphthalenyl]methoxy-[1,1'-biphenyl]-6-[(E)-3-propenoic acid], methyl ester (38d) (0.629 g., 1.20 mmol, 1 equiv.) is dissolved in 10 mL of EtOAc and 10% palladium on carbon (0.100 g., 0.094 mmol, 8 mol %) is added. The suspension is hydrogenated using a balloon of hydrogen for 3.5 hours. The mixture is filtered through a pad of Florisil, eluthng with ether and ethyl acetate. The filtrate is evaporated, and the crude material is chromatographed on silica gel using 5% EtOAc/hexane to yield 3'-carboethoxy-2-[5,6,7,8-tetrahydro-5,5,8,8-tetramethyl-2-naphthalenyl]methoxy[1,1'-biphenyl]-6-[3-propanoic acid], methyl ester (36d) (0.608 g., 1.15 mmol, 96%) as a clear oil: UV$_{max}$ (CHCl$_3$) 242 nm (ε=9776), 278 nm (ε=3210); $^1$H NMR (300 MHz, CDCl$_3$) δ 8.04 (ddd, J=2, 2, 8 Hz, 1H, ArH), 7.97 (dd, J=2, 2 Hz, 1H, ArH), 7.45 (m, 2H, ArH), 7.28 (dd, J=8, 8 Hz, 1H, ArH), 7.16 (d, J=8 Hz, 1H, ArH), 6.97 (d, J=2 Hz, 1H, ArH), 6.93 (d, J=3 Hz, 1H, ArH), 6.90 (d, J=3 Hz, 1H, ArH), 6.86 (dd, J=2, 8 Hz, 1H, ArH), 4.91 (s, 2H, ArCH$_2$O), 4.35 (q, J=7 Hz, 2H, CO$_2$CH$_2$), 3.57 (s, 3H, CO$_2$CH$_3$), 2.73 (dd, J=8, 8 Hz, 2H, ArCH$_2$CH$_2$CO$_2$), 2.39 (dd, J=8, 8 Hz, 2H, ArCH$_2$CH$_2$CO$_2$), 1.61 (s, 4H, CH$_2$CH$_2$), 1.36 (t, J=7 Hz, 3H, CO$_2$CH$_2$CH$_3$), 1.21 (s, 6H, 2×CH$_3$), 1.09 (s, 6H, 2×CH$_3$); $^{13}$C NMR (75 MHz, CDCl$_3$) δ 173.15 (C=0), 166.60 (C=0), 156.16, 144.81, 144.03, 140.06, 137.40, 134.67, 133.95, 131.14, 130.54, 130.47, 128.77, 128.34, 128.25, 126.36, 124.43, 123.63, 121.41, 110.60, 69.97, 60.92, 51.55, 34.99, 34.15, 34.03, 31.80, 31.66, 28.42, 14.33; IR (film) 2958, 2928, 1738, 1718, 1580, 1456, 1364, 1296, 1258, 1230, 1080, 758 cm$^{-1}$; MS (DCI) m/e 529 (MH+), 483 (M-C$_2$H$_5$O), 201 (C$_{15}$H$_{21}$+). Anal. Calcd for C$_{34}$H$_{40}$O$_5$: C, 77.24; H, 7.63. Found: C, 76.97; H, 7.52.

3'-Carboethoxy-2-[5,6,7,8-tetrahydro-5,5,8,8-tetramethyl-2-naphthalenyl]methoxy-[1,1'-biphenyl]-6-[3-propanoic acid], methyl ester (36d) (0.548 g., 1.04 mmol) is hydrolyzed via the method of Example 7 to afford 3'-carboxy-2-[5,6,7,8-tetrahydro-5,5,8,8-tetramethyl-2-naphthalenyl]methoxy-[1,1'-biphenyl]-6-propanoic acid (37d) (0.306 g., 0.630 mmol, 61%) as a white solid: recrystallized from $CH_2Cl_2$/pentane; mp=160°-161° C.; $UV_{max}$ ($CHCl_3$) 242 nm ($\epsilon$=11222), 278 nm ($\epsilon$=3474); $^1H$ NMR (300 MHz, $CDCl_3$) $\delta$ 8.04 (m, 2H, ArH), 7.49 (m, 2H, ArH), 7.29 (dd, J=8, 8 Hz, 1H, ArH), 7.15 (d, J=8 Hz, 1H, ArH), 6.98 (d, J=2 Hz, t, ArH), 6.93 (d, J=8 Hz, 1H, ArH), 6.91 (d, J=8 Hz, 1H, ArH), 6.85 (dd, J=2, 8 Hz, 1H, ArH), 4.91 (s, 2H, $ArCH_2O$), 2.72 (m, 2H, $ArCH_2CH_2CO_2$), 2.49 (m, 2H, $ArCH_2CH_2CO_2$), 1.59 (s, 4H, $CH_2CH_2$), 1.20 (s, 6H, 2×$CH_3$), 1.08 (s, 6H, 2×$CH_3$); $^{13}C$ NMR (75 MHz, $CDCl_3$) $\delta$ 179.38 (C=O), 172.41 (C=O), 156.14, 145.85, 144.85, 144.05, 139.77, 137.49, 135.78, 133.87, 132.05, 130.40, 129.23, 128.90, 128.30, 126.37, 124.46, 123.66, 121.19, 110.61, 70.00, 35.13, 34.99, 34.13, 34.03, 31.79, 31.65, 27.87; IR (KBr) 3414, 2960, 2928, 1704, 1580, 1458, 1260, 1078 cm$^{-1}$; MS (DCI) m/e 487 (MH+), 469 (M-OH), 201 ($C_{15}H_{21}^+$). Anal. Calcd for $C_{31}H_{34}O_5.0.7 H_2O$: C, 74.58; H, 7.15. Found: C, 74.62; H, 6.89.

Example 25: Synthesis of Diacids 39a–c

A. Synthesis of Aldehydes 16a–c

2-Hydroxy-3'-carboethoxy-[1,1'-biphenyl]-6-carboxaldehyde (15a, from Example 6) is coupled to alcohols 12b, 12d, and 12c (see Example 8) via the method of Example 11 to afford ethers 16a, 16b, and 16c, respectively.

For 2-[3,4-bis (3-methyl-2-butenyloxy)phenyl]methoxy-3'-carboethoxy-[1,1'-biphenyl]-6-carboxaldehyde (16a): scale=0.980 mmol, yield=49%; chromatographed on silica gel using $CH_2Cl_2$/hexane to afford an oil; $^1H$ NMR (300 MHz, $CDCl_3$) $\delta$ 9.75 (s, 1H, CHO), 8.15-8.05 (m, 2H, ArH), 7.76-7.25 (m, 5H, ArH), 6.81-6.60 (m, 3H, ArH), 5.48 (m, 2H, 2×C=CH), 4.99 (s, 2H, $ArCH_2O$), 4.54 (q, J=7 Hz, 2H, $CO_2CH_2$), 4.39 (m, 4H, 2×$OCH_2C$=C), 1.70 (s, 6H, 2×$CH_3$), 1.69 (s, 3H, $CH_3$), 1.66 (s, 3H, $CH_3$), 1.38 (t, J=7 Hz, 3H, $CO_2CH_2CH_3$).

For 2-[(3,4-biscyclopentyloxy)phenyl]methoxy-3'-carboethoxy-[1,1'-biphenyl]-6-carboxaldehyde (16b): scale=2.00 mmol, yield=41%; chromatographed on silica gel using $CH_2Cl_2$/hexane, then $CH_2Cl_2$, then 5% EtOAc/$CH_2Cl_2$ to afford an oil; $^1H$ NMR (300 MHz, $CDCl_3$) $\delta$ 9.74 (s, 1H, CHO), 8.15-7.66 (m, 10H, ArH), 4.98 (s, 2H, $ArCH_2O$), 4.70 (b, 2H, 2x$R_2CHOR$), 4.35 (q, J=7 Hz, 2H, $CO_2CH_2$), 1.82-1.58 (m, 16H, cyclopentyl), 1.38 (t, J=7 Hz, 3H, $CO_2CH_2CH_3$).

For 2-[(3,4-bispentyloxy)phenyl]methoxy-3'-carboethoxy-[1,1'-biphenyl]-6-carboxaldehyde (16c): scale=3.00 mmol; chromatographed on silica gel using $CH_2Cl_2$/hexane to afford an oil: $^1H$ NMR (300 MHz, $CDCl_3$) $\delta$ 9.75 (s, 1H, CHO), 8.13-8.10 (m, 1H, ArH), 8.09 (s, 1H, ArH), 7.65 (dd, J=2, 8 Hz, 1H, ArH), 7.55-7.40 (m, 3H, ArH), 7.27 (dd, J=2, 8 Hz, 1H, ArH), 6.80-6.65 (m, 3H, ArH), 4.98 (s, 2H, $ArCH_2O$), 4.39 (q, J=7 Hz, 2H, $CO_2CH_2$), 3.92 (t, J=6 Hz, 2H, $OCH_2CH_2R$), 3.79 (t, J=6 Hz, 2H, $OCH_2CH_2R$), 1.82-1.75 (m, 4H, $OCH_2CH_2R$), 1.45-1.36 (m, 11H, 2x$RCH_2CH_2CH_3$ and $CO_2CH_2CH_3$), 0.94 (m, 6H, 2×$CH_3$); $^{13}C$ NMR (75 MHz, $CDCl_3$) 191.83 (C=O), 166.19 (C=O), 149.22, 148.50, 135.31, 134.44, 133.76, 132.01, 130.36, 129.13, 129.08, 129.00, 128.92, 127.99, 119.79, 119.18, 118.23, 113.56, 112.27, 70.66, 69.30, 69.01, 61.14, 28.98, 28.19, 22.47, 14.30, 14.03.

B. Synthesis of Esters 38a–c

Aldehydes 16a, 16b and 16c are converted to unsaturated esters 38a, 38b, and 38c, respectively, using the method of Example 23.

For (E)-2-[3,4-bis(3-methyl-2-butenyloxy)phenyl]methoxy-6-[methyl (3-propenoate)]-1,1'-biphenyl-3'-carboxylic acid, methyl ester (38a): scale=0.90 mmol, yield=36%; chromatographed on silica gel using $CH_2Cl_2$/hexane to afford an oil; $UV_{max}$ (EtOH) 206 nm ($\epsilon$=64456), 232 nm ($\epsilon$=38475), 284 nm ($\epsilon$=19713); $^1H$ NMR (300 MHz, $CDCl_3$) $\delta$ 8.05 (d, J=8 Hz, 1H, ArH), 8.00 (s, 1H, ArH), 7.51-7.06 (m, 5H, ArH and C=CH), 6.79 (d, J=8 Hz, 1H, ArH), 6.70-6.60 (m, 3H, ArH), 6.37 (d, J=16 Hz, 1H, C=CH), 5.49 (m, 2H, 2×$OCH_2CH$=C), 4.92 (s, 2H, $ArCH_2O$), 4.55 (d, J=6 Hz, 2H, $OCH_2CH$=C), 4.39 (d, J=6 Hz, 2H, $OCH_2CH$=C), 3.90 (s, 3H, $CO_2CH_3$), 3.69 (s, 3H, $CO_2CH_3$), 1.75 (s, 6H, 2×$CH_3$), 1.66 (s, 6H, 2×$CH_3$); $^{13}C$ NMR (75 MHz, $CDCl_3$) $\delta$ 167.02 (C=O), 166.87 (C=O), 156.09, 148.86, 148.27, 143.02, 137.56, 137.09, 136.00, 135.51, 134.56, 131.93, 131.55, 129.95, 129.29, 128.92, 128.66, 128.08, 120.27, 119.92, 119.45, 119.15, 119.08, 114.34, 113.66, 112.34, 70.28, 65.93, 65.64, 52.09, 51.59, 25.77, 18.19; IR (KBr) 2900, 1730 (C=O), 1663 (C=O), 1510, 1430, 1255, 1230 cm$^{-1}$; MS (DCI) m/e 571 (MH+), 539, 503, 471, 449, 435, 313, 259. Anal. Calcd for $C_{35}H_{36}O_7.0.1 CH_2Cl_2$: C, 72.60; H, 6.60. Found: C, 72.64; H, 6.91.

For (E)-2-[(3,4-biscyclopentyloxy)phenyl]methoxy-6-[methyl (3-propenoate)]-1,1'-biphenyl-3'-carboxylic acid, methyl ester (38b): scale=1.08 mmol, yield=57%; chromatographed on silica gel using $CH_2Cl_2$/hexane to afford an oil; $^1H$ NMR (300 MHz, $CDCl_3$) $\delta$ 8.09 (d, J=8 Hz, 1H, ArH), 7.99 (s, 1H, ArH), 7.46-7.04 (m, 6H, ArH and C=CH), 6.79 (d, J=8 Hz, 1H, ArH), 6.68 (d, J=8 Hz, 1H, ArH), 6.63 (s, 1H, ArH), 6.37 (d, J=13 Hz, 1H, C=CH), 3.93 (s, 2H, $ArCH_2O$), 4.69-4.52 (m, 2H, 2x$R_2CHOR$), 3.90 (s, 3H, $CO_2CH_3$), 3.70 (s, 3H, $CO_2CH_3$), 1.82-1.58 (m, 16H, cyclopentyl); $^{13}C$ NMR (75 MHz, $CDCl_3$) $\delta$ 167.03 (C=O), 166.88 (C=O), 156.91, 148.86, 148.36, 143.04, 136.03, 135.34, 134.59, 131.89, 131.52, 129.94, 129.47, 128.91, 128.64, 128.09, 119.44, 119.33, 119.03, 116.49, 115.18, 114.22, 81.06, 80.79, 70.29, 52.09, 51.59, 32.77, 23.90.

For (E)-2-[(3,4-bispentyloxy)phenyl]methoxy-6-[methyl (3-propenoate)]-1,1'-biphenyl-3'-carboxylic acid, methyl ester (38c): scale=1.73 mmol, yield=63%; chromatographed on silica gel using $CH_2Cl_2$/hexane to afford an oil; $UV_{max}$ (EtOH) 208 nm ($\epsilon$=47562), 232 nm ($\epsilon$=36190), 284 nm ($\epsilon$=19436); $^1H$ NMR (300 MHz, $CDCl_3$) $\delta$ 8.08 (d, J=8 Hz, 1H, ArH), 7.98 (s, 1H, ArH), 7.51-7.34 (m, 6H, ArH and C=CH), 7.06 (dd, J=5, 5 Hz, 1H, ArH), 6.61 (s, 1H, ArH), 6.37 (d, J=16 Hz, 1H, C=CH), 4.94 (s, 2H, $ArCH_2O$), 3.97 (t, J=7 Hz, 2H, $OCH_2R$), 3.95 (s, 3H, $OCH_3$), 3.77 (t, J=7 Hz, 2H, $OCH_2R$), 3.70 (s, 3H, $OCH_3$), 1.81-0.90 (m, 18 H, pentyl); $^{13}C$ NMR (300 MHz, $CDCl_3$) $\delta$ 167.02 (C=O), 166.88 (C=O), 156.10, 149.20, 149.04, 143.01, 136.05, 134.60, 132.46, 131.02, 131.59, 130.17, 129.96, 129.30, 128.91, 128.65, 128.09, 119.46, 119.07, 114.82, 113.76, 112.10, 70.34, 69.29, 68.92, 52.09, 51.59, 29.07, 28.99, 28.27, 28.22, 22.51, 22.48, 14.07; IR (KBr) 2960, 2870, 1750, 1690, 1510, 1280, 1200 cm$^{-1}$; MS (DCI) m/e 575 (MH+), 543, 295, 263. Anal. Calcd for $C_{35}H_{42}O_7.0.25 H_2O$: C, 73.17; H, 7.32. Found: C, 73.21; H, 7.63.

C. Synthesis of Diacids 39a-c from Diesters 38a-c

Diesters 38a, 38b, and 38c are hydrolyzed via the method of Example 7 to afford diacids 39a-c.

For 2-[3,4-bis (3-methyl-2-butenyloxy)phenyl]methoxy-3'-carboxy-[1,1'-biphenyl]-6-[(E)-3-propenoic acid] (39a): scale 0. 540 mmol, yield=70%; recrystallized using $CH_2Cl_2$/hexane; mp=175°-179° C.; $UV_{max}$ (EtOH) 208 nm ($\epsilon$=55237), 232 nm ($\epsilon$=36495), 282 nm ($\epsilon$=18975); $^1H$ NMR (300 MHz, $CDCl_3$) $\delta$ 7.96 (d, J=8 Hz, 1H, ArH), 7.83 (s, 1H, ArH), 7.44 (dd, J=8, 8 Hz, 1H, ArH), 7.35-7.24 (m, 4H, ArH and CH=CHCO$_2$H), 7.07 (d, J=8 Hz, 1H, ArH), 6.74-6.61 (m, 3H, ArH), 6.26 (d, J=16 Hz, 1H, C=CHCO$_2$H), 5.33 (m, 2H, 2×OCH$_2$CH=C), 4.86 (s, 2H, ArCH$_2$O), 4.47 (d, J=6 Hz, 2H, OCH$_2$CH=C), 4.34 (d, J=6 Hz, 2H, OC$_2$CH=C), 1.66 (s, 6H, 2×CH$_3$), 1.61 (s, 6H, 2×CH$_3$); $^{13}C$ NMR (75 MHz, $CDCl_3$) $\delta$ 169.82, (C=O), 169.51 (C=O), 156.68, 149.36, 148.70, 143.85, 138.52, 138.14, 136.76, 135.85, 132.79, 131.26, 130.46, 129.56, 129.33, 128.53, 120.68, 120.58, 120.25, 120.08, 119.74, 115.11, 114.77, 113.31, 70.91, 66.72, 66.36, 25.94, 25.92, 18.34, 18.30; IR (KBr) 3240 (OH), 2900, 1680 (C=O), 1630, 1510, 1250 cm$^{-1}$; MS (DCI) m/e 517, 267, 259. Anal. Calcd for $C_{33}H_{34}O_7$.0.75 $H_2O$: C, 71.46; H, 6.45. Found: C, 71.29; H, 6.31.

For 2-[(3,4-bis(cyclopentyloxy)phenyl]methoxy-3'-carboxy-[1,1'-biphenyl]-6-[(E)-3-propenoic acid] (39b): scale=0.753 mmol, yield=75%; recrystallized using ether/hexane; mp=215°-216° C.; $UV_{max}$ (EtOH) 208 nm ($\epsilon$=47271), 232 nm ($\epsilon$=35149), 282 nm ($\epsilon$=18855); $^1H$ NMR (300 MHz, $CDCl_3$) $\delta$ 8.05 (ddd, J=2, 2, 8 Hz, 1H, ArH), 7.91 (dd, J=2, 2 Hz, 1H, ArH), 7.51-7.31 (m, 5H, ArH and CH=CHCO$_2$H), 7.14 (dd, J=2, 8 Hz, 1H, ArH), 6.79 (d, J=6 Hz, 1H, ArH), 6.68 (dd, J=2, 6 Hz, 1H, ArH), 6.61 (d, J=2 Hz, 1H, ArH), 6.35 (d, J=16 Hz, 1H, C=CHCO$_2$H), 4.92 (s, 2H, ArCH$_2$O), 4.70-4.68 (m, 1H, R$_2$CHOAr) 4.52-4.49 (m, 1H, R$_2$CHOAr) 1.77-1.56 (m, 16H, cyclopentyl); $^{13}C$ NMR (75 MHz, $CDCl_3$) $\delta$ 172.70 (C=O), 172.33 (C=O), 159.92, 152.48, 151.80, 146.90, 140.24, 139.09, 138.22, 135.73, 135.35, 134.43, 133.94, 132.80, 132.33, 131.78, 123.57, 123.24, 122.65, 120.27, 118.65, 118.11, 84.95, 84.47, 73.72, 36.18, 27.42, 27.31; IR (KBr) 3420, 2960, 1685, 1630, 1250 cm$^{-1}$; MS (DCI) m/e 543 (MH+), 457 (M-C$_4$H$_8$O), 281, 267, 259. Anal. Calcd for $C_{33}H_{34}O_7$.0.75 $H_2O$: C, 71.46; H, 6.43. Found: C, 1.04; H, 6.03.

For 2-[(3,4-bis (pentyloxy)phenyl]methoxy-3'-carboxy-[1,1'-biphenyl]-6-[(E)-3-propenoic acid] (39c): scale=0.734 mmol, yield=73%; recrystallized using ether/hexane; mp=191°-193° C.; $UV_{max}$ (EtOH) 206 nm ($\epsilon$=49197), 232 nm ($\epsilon$=36853), 282 nm ($\epsilon$=20355); $^1H$ NMR (300 MHz, $CDCl_3$) $\delta$ 8.00 (ddd, J=2, 2, 8 Hz, 1H, ArH), 7.91 (dd, J=2, 2 Hz, 1H, ArH), 7.43-7.27 (m, 5H, ArH and CH=CHCO$_2$H), 7.01 (dd, J=4, 8 Hz, 1H, ArH), 6.69 (d, J=8 Hz, 1H, ArH), 6.61 (dd, J=2, 8 Hz, 1H, ArH), 6.55 (d, J=2 Hz, 1H, ArH), 6.22 (d, J=16 Hz, 1H, CH=CHCO$_2$H), 4.87 (s, 2H, ArCH$_2$O), 3.93-3.66 (m, 4H, 2xRCH$_2$O), 1.76-0.82 (m, 18H, pentyl); $^{13}C$ NMR (75 MHz, $CDCl_3$) $\delta$ 169.11 (C=O), 168.92 (C=O), 155.98, 149.05, 148.37, 143.69, 135.91, 135.43, 134.52, 132.26, 131.53, 130.05, 129.39, 128.87, 127.96, 119.74, 119.16, 119.09, 118.75, 114.35, 113.60, 112.15, 70.31, 69.35, 68.99, 28.87, 28.81, 28.16, 28.10, 22.40, 13.93; IR (KBr) 3400 (OH), 2950, 1685 (C=O), 1625, 1513, 1257, 1140 cm$^{-1}$; MS (DCI) m/e 547 (MH+), 529 (M-OH), 299, 281, 267. Anal. Calcd for $C_{33}H_{38}O_7$.0.5 $H_2O$: C, 71.33; H, 7.07. Found: C, 71.10, H, 6.87.

Experimental Procedures for Compounds Of Type IE

Example 26 Synthesis of Acids 44 and 48

For 44:

3,4-Dihydroxybenzaldehyde (0.580 g., 4.20 mmol, 1 equiv.) is dissolved in 4.2 mL of acetone. 2-Chloromethyl-(5,5,8,8-tetramethyl-5,6,7,8-tetrahydronaphthalene) (18a) (1.00 g., 4.20 mmol, 1 equiv.), sodium iodide (0.020 g., 0.133 mmol, 0.03 equiv.), and potassium carbonate (0.580 g., 4.20 mmol, 1 equiv.) are added, and the mixture is heated to reflux for 19 hours. The mixture is poured into water, and extracted twice with ether, and once with EtOAc. The combined extracts are washed with brine, dried (MgSO$_4$), and concentrated. The crude material is chromatographed on silica gel using EtOAc/hexane as the eluent to afford 3-hydroxy-4-[5,6,7,8-tetrahydro-5,5,8,8-tetramethyl-2-naphthalenyl]-methoxy benzaldehyde (41) (0.666 g., 1.97 mmol, 47%) as a white solid: $^1H$ NMR (300 MHz, $CDCl_3$) $\delta$ 9.87 (s, 1H, CHO), 7.48-7.35 (m, 4H, ArH), 7.22 (dd, J=2, 8 Hz, 1H, ArH), 7.09 (d, J=8 Hz, 1H, ArH), 5.14 (s, 2H, ArCH$_2$O), 1.72 (s, 4H, CH$_2$CH$_2$), 1.32 (s, 6H, 2×CH$_3$), 1.31 (s, 6H, 2×CH$_3$); $^{13}C$ NMR (75 MHz, $CDCl_3$) $\delta$ 191.00 (C=O), 151.20, 146.33, 145.79, 145.53, 132.11, 130.76, 127.17, 126.53, 125.51, 124.31, 114.28, 111.42, 71.60, 34.92, 34.26, 31.82; IR (KBr) 3342, 2962, 2932, 1682, 1608, 1582, 1512, 1278, 1112 cm$^{-1}$; MS (DCI) m/e 339 (MH+), 201 ($C_{15}H_{21}^+$).

3-Hydroxy-4-[5,6,7,8-tetrahydro-5,5,8,8-tetramethyl-2-naphthalenyl]methoxy-benzaldehyde (41) (0.654 g., 1.93 mmol) is converted by the method of Example 1 to 3-trifluoromethyl-sulphonyloxy-4-[5,6,7,8-tetrahydro-5,5,8,8-tetramethyl-2-naphthalenyl]methoxy benzaldehyde (42) (0.753 g., 1.60 mmol, 83%): chromatographed on silica gel using $CH_2Cl_2$/hexane; $^1H$ NMR (300 MHz, $CDCl_3$) $\delta$ 9.87 (s, 1H, CHO), 7.83 (dd, J=2, 8 Hz, 1H, ArH), 7.75 (d, J=2 Hz, 1H, ArH), 7.38 (d, J=2 Hz, 1H, ArH), 7.32 (d, J=8 Hz, 1H, ArH), 7.21 (d, J=8 Hz, 1H, ArH), 7.16 (dd, J=2, 8 Hz, 1H, ArH), 5.21 (s, 2H, ArCH$_2$O), 1.67 (s, 4H, CH$_2$CH$_2$), 1.26 (s, 6H, 2×CH$_3$), 1.26 (s, 6H, 2×CH$_3$); $^{13}C$ NMR (75 MHz, $CDCl_3$) $\delta$ 189.08 (C=O), 155.67, 155.00, 145.54, 145.41, 131.84, 131.44, 129.93, 126.98, 125.54, 124.47, 122.93, 114.24, 71.79, 35.02, 34.94, 34.33, 34.22, 31.83, 31.70; IR (film) 2962, 2930, 1700, 1608, 1510, 1426, 1280, 1210, 1140, 840 cm$^{-1}$; MS (DCI) m/e 471 (MH+), 201 ($C_{15}H_{21}^+$).

3-Trifluoromethylsulphonyloxy-4-[5,6,7,8-tetrahydro-5,5,8,8-tetramethyl-2-naphthalenyl]methoxy benzaldehyde (42) (0.745 g., 1.58 mmol) is coupled with phenyltributylstannane (0.870 g., 2.38 mmol) via the method of Example 3 to afford 2-[5,6,7,8-tetrahydro-5,5,8,8-tetramethyl-2-naphthalenyl]methoxy-[1,1'-biphenyl]-5-carboxaldehyde (43) (0.404 g., 1.02 mmol, 65%): chromatographed on silica gel using $CH_2Cl_2$/hexane; $^1H$ NMR (300 MHz, $CDCl_3$) $\delta$ 9.93 (s, 1H, CHO), 7.87 (d, J =2 Hz, 1H, ArH), 7.84 (dd, J=2, 8 Hz, 1H, ArH), 7.57 (m, 2H, ArH), 7.44-7.32 (m, 3H, ArH), 7.25 (m, 2H, ArH), 7.16 (d, J=8 Hz, 1H, ArH), 7.05 (dd, J=2, 8 Hz, 1H, ArH), 5.14 (s, 2H, ArCH$_2$O), 1.65 (s, 4H, CH$_2$CH$_2$), 1.25 (s, 6H, 2×CH$_3$), 1.20 (s, 6H, 2×CH$_3$); $^{13}C$ NMR (75 MHz, $CDCl_3$) $\delta$ 190.95 (C=O), 160.72, 145.19, 144.65, 137.22, 132.97, 132.59, 131.86, 131.20, 130.00, 129.54, 128.16, 127.48, 126.71, 124.89, 123.96, 112.57, 70.50, 34.99, 34.27, 34.13, 31.83, 31.80;

IR (film) 2960, 2926, 1692, 1596, 1504, 1264, 1182 cm$^{-1}$; MS (DCI) m/e 399 (MH+), 201 ($C_{15}H_{21}$+).

2-[5,6,7,8-Tetrahydro-5,5,8,8-tetramethyl-2-naphthalenyl]methoxy-[1,1'-biphenyl]-5-carboxaldehyde (43) (0.391 g., 0.98 mmol) is oxidized by the method of Example 4 to yield 2-[5,6,7,8-tetrahydro-5,5,8,8-tetramethyl-2-naphthalenyl]methoxy-[1,1'-biphenyl]-5-carboxylic acid (44) (0.391 g., 0.94 mmol, 96%) as a white solid: mp=195°–198° C.; UV$_{max}$ (MeOH) 204 nm ($\epsilon$=31402), 238 nm ($\epsilon$=30400), 260 nm ($\epsilon$=16769); $^1$H NMR (300 MHz, CD$_3$OD) δ 7.99 (dd, J=2, 8 Hz, 1H, ArH), 7.95 (d, J=2 Hz, 1H, ArH), 7.53 (m, 2H, ArH), 7.42–7.23 (m, 5H, ArH), 7.20 (d, J=8 Hz, 1H, ArH), 7.04 (dd, J=2, 8 Hz, 1H, ArH), 5.11 (s, 2H, ArCH$_2$O), 1.66 (s, 4H, CH$_2$CH$_2$), 1.23 (s, 6H, 2×CH$_3$), 1.18 (s, 6H, 2×CH$_3$); $^{13}$C NMR (75 MHz, CD$_3$OD) δ 169.78 (C=O), 160.87, 146.00, 145.41, 139.22, 134.94, 133.45, 132.42, 132.01, 130.61, 129.13, 128.26, 127.60, 126.18, 125.33, 124.34, 113.58, 71.39, 36.19, 35.20, 35.03, 32.29, 32.24; IR (KBr) 3430, 2958, 2926, 1688, 1604, 1258, 820 cm$^{-1}$; MS (DCI) m/e 415 (MH+), 201 ($C_{15}H_{21}$+). Anal. Calcd for $C_{28}H_{30}O_3$.0.1 $H_2O$: C, 80.77; H, 7.31. Found: C, 80.70; H, 7.30.

For 48:

Sodium hydride (0.139 g., 4.60 mmol, 1.1 equiv.; 80% in oil washed with pentane) is suspended in 6 mL of DMSO. 2,3-Dihydroxybenzaldehyde (0.580 g., 4.20 mmol, 1 equiv.) dissolved in 2.8 mL of DMSO is added dropwise via cannula, and the mixture is allowed to stir for 1 hour. 2-Chloromethyl-(5,5,8,8-tetramethyl-5,6,7,8-tetrahydronaphthalene) (18a) (1.00 g., 4.20 mmol, 1 equiv.) dissolved in 8 mL of DMSO is added dropwise via cannula, and the mixture allowed to stir 26.5 hours. The mixture is partitioned between saturated aqueous ammonium chloride solution and EtOAc. Salt is added to the aqueous phase, which is then extracted twice with EtOAc. The combined extracts are washed with brine, dried (MgSO$_4$), and treated with charcoal before filtering through a pad of silica gel. The filtrate is evaporated, and the crude material is chromatographed on silica gel using EtOAc/hexane to afford 3-hydroxy-2-[5,6,7,8-tetrahydro-5,5,8,8-tetramethyl-2-naphthalenyl]-methoxy benzaldehyde (45) (0.786 g., 2.33 mmol, 56%) as an oil: $^1$H NMR (300 MHz, CDCl$_3$) δ 10.14 (s, 1H, CHO), 7.35 (m, 2H, ArH), 7.22–7.09 (m, 4H, ArH), 5.77 (s, 1H, OH), 5.00 (s, 2H, ArCH$_2$O), 1.67 (s, 4H, CH$_2$CH$_2$), 1.27 (s, 6H, 2×CH$_3$), 1.22 (s, 6H, 2×CH$_3$); $^{13}$C NMR (75 MHz, CDCl$_3$) δ 189.40 (C=O), 149.74, 148.00, 146.20, 145.64, 132.58, 129.63, 127.36, 127.11, 126.00, 125.12, 121.64, 121.34, 79.18, 34.92, 34.90, 34.27, 31.80, 31.75; IR (KBr) 3226, 2958, 2926, 1662, 1604, 1580, 1470, 1294, 1284, 1222, 934, 786 cm$^{-1}$; MS (DCI) m/e 339 (MH+), 201 ($C_{15}H_{21}$+).

3-Hydroxy-2-[5,6,7,8-tetrahydro-5,5,8,8-tetramethyl-2-naphthalenyl]methoxy benzaldehyde (45) (0.730 g., 2.16 mmol) is converted by the method of Example 1 to 3-trifluoromethyl-sulphonyloxy-2-5,6,7,8-tetrahydro-5,5,8,8-tetramethyl-2-naphthalenyl]methoxy benzaldehyde (46) (0. 819 g., 1.74 mmol, 80%): chromatographed on silica gel using CH$_2$Cl$_2$/hexane to afford a yellow oil; $^1$H NMR (300 MHz, CDCl$_3$) δ 9.89 (s, 1H, CHO), 7.77 (dd, J=2, 8 Hz, 1H, ArH), 7.52 (dd, J=2, 8 Hz, 1H, ArH), 7.27 (m, 2H, ArH), 7.13 (d, J=2 Hz, 1H, ArH), 7.07 (dd, J=2, 8 Hz, 1H, ArH), 5.09 (s, 2H, ArCH$_2$O), 1.65 (s, 4H, CH$_2$CH$_2$), 1.25 (s, 6H, 2×CH$_3$), 1.17 (s, 6H, 2×CH$_3$); $^{13}$C NMR (75 MHz, CDCl$_3$) δ 187.63 (C=O), 146.43, 145.42, 132.23, 131.03, 128.11, 127.89, 127.85, 127.18, 126.68, 125.00, 78.99, 34.87, 34.25, 34.19, 31.77, 31.65; IR (film) 2962, 2930, 1698, 1604, 1468, 1426, 1242, 1220, 1178, 1140, 954, 832, 796 cm$^{-1}$; MS (DCI) m/e 471 (MH+), 201 ($C_{15}H_{21}$+).

3-Trifluoromethylsulphonyloxy-2-[5,6,7,8-tetrahydro-5,5,8,8-tetramethyl-2-naphthalenyl]methoxy benzaldehyde (46) (0.844 g., 1.79 mmol) is coupled with phenyltributylstannane (0.760 g., 2.06 mmol) via the method of Example 3 to afford 2-[5,6,7,8-tetrahydro-5,5,8,8-tetramethyl-2-naphthalenyl]methoxy-[1,1'-biphenyl]-3-carboxaldehyde (47) (0.380 g., 0.96 mmol, 54%): chromatographed on silica gel using CH$_2$Cl$_2$/hexane to afford an oil; $^1$H NMR (300 MHz, CDCl$_3$) 10.32 (s, 1H, CHO), 7.81 (dd, J=2, 8 Hz, 1H, ArH), 7.61 (m, 3H, ArH), 7.44 (m, 3H, ArH), 7.28 (dd, J=8, 8 Hz, 1H, ArH), 7.20 (d, J=8 Hz, 1H, ArH), 6.88 (d, J=2 Hz, 1H, ArH), 6.84 (dd, J=2, 8 Hz, 1H, ArH), 4.46 (s, 2H, ArCH$_2$O), 1.67 (s, 4H, CH$_2$CH$_2$), 1.22 (s, 6H, 2×CH$_3$), 1.17 (s, 6H, 2×CH$_3$); $^{13}$C NMR (75 MHz, CDCl$_3$) δ 190.30 (C=O), 159.90, 145.01, 137.32, 137.23, 136.56, 132.38, 130.29, 129.23, 128.62, 127.86, 127.31, 127.18, 126.83, 126.18, 124.62, 34.96, 34.93, 34.15, 31.78, 31.75; IR (film) 2958, 2926, 1688, 1584, 1458, 1364, 1244, 1210, 764, 700 cm$^{-1}$; MS (DCI) m/e 398 (MH+), 201 ($C_{15}H_{21}$+).

2-[5,6,7,8-Tetrahydro-5,5,8,8-tetramethyl-2-naphthalenyl]methoxy-[1,1'-biphenyl]-3-carboxaldehyde (47) (0.369 g., 0.93 mmol) is oxidized by the method of Example 4 to yield 2-[5,6,7,8-tetrahydro-5,5,8,8-tetramethyl-2-naphthalenyl]methoxy-[1,1'-biphenyl]-3-carboxylic acid (48) (0.385 g., 0.93 mmol, 100%) as a white solid: mp=144°–146° C.; UV$_{max}$ (MeOH) 208 nm ($\epsilon$=34800), 290 nm ($\epsilon$=1700); $^1$H NMR (300 MHz, CD$_3$OD) δ 7.79 (dd, J=2, 8 Hz, 1H, ArH), 7.53 (m, 3H, ArH), 7.44 (m, 3H, ArH), 7.28 (dd, J=8, 8 Hz, 1H, ArH), 7.15 (d, J=8 Hz, 1H, ArH), 6.92 (d, J=2 Hz, 1H, ArH), 6.81 (dd, J=2, 8 Hz, 1H, ArH), 4.48 (s, 2H, ArCH$_2$O), 1.65 (s, 4H, CH$_2$CH$_2$), 1.22 (s, 6H, 2×CH$_3$), 1.18 (s, 6H, 2×CH$_3$); $^{13}$C NMR (75 MHz, CD$_3$OD) δ 169.72 (C=O), 156.45, 145.88, 145.61, 139.23, 138.62, 135.88, 134.59, 131.57, 130.60, 129.47, 128.68, 128.46, 128.09, 127.54, 127.39, 125.42, 77.36, 36.19, 35.09, 35.03, 32.27, 32.23; IR (KBr) 3448, 2966, 2922, 2858, 1698, 1680, 1586, 1466, 1448, 1378, 1284, 1218, 982 cm$^{-1}$; MS (DCI) m/e 414 (M+), 201 ($C_{15}H_{21}$+). Anal. Calcd for $C_{28}H_{30}O_3$.0.3 $H_2O$: C, 80.08; H, 7.35 Found: C 80.13; H, 7.35.

Experimental Procedures for Compounds of Type II

Example 27: Synthesis of Acids 52a–b

2-Bromophenol (1.50 g., 8.70 mmol) is alkylated with 2-chloromethyl-(5,5,8,8-tetramethyl-5,6,7,8-tetrahydronaphthalene) (18a) (2.05 g., 8.70 mmol) in a similar manner as described in Example 26 (for the synthesis of 44) to afford 2-[5,6,7,8-tetrahydro-5,5,8,8-tetramethyl-2-naphthalenyl]methoxy-bromobenzene (50) (2.88 g., 7.72 mmol, 89%): chromatographed on silica gel using EtOAc/hexane to afford a clear oil; $^1$H NMR (300 MHz, CDCl$_3$) δ 7.57 (dd, J=2, 8 Hz, 1H, ArH), 7.45 (d, J=2 Hz, 1H, ArH), 7.32 (d, J=8 Hz, 1H, ArH), 7.25 (m, 2H, ArH), 6.98 (dd, J=2, 8 Hz, 1H, ArH), 6.83 (dd, J=8, 8 Hz, 1H, ArH), 5.09 (s, 2H, ArCH$_2$O), 1.70 (s, 4H, CH$_2$CH$_2$), 1.29 (s, 6H, 2×CH$_3$), 1.28 (s, 6H, 2×CH$_3$).

Bromide 50 is coupled via the method of Example 3 to stannanes 3a and 3f (see Example 2) to afford esters 51a and 51b, respectively.

For 2-[5,6,7,8-tetrahydro-5,5,8,8-tetramethyl-2-naphthalenyl]methoxy-3'-carboethoxy-1,1'-biphenyl (51a):

scale=0.71 mmol, yield=59%; chromatographed on silica gel using EtOAc/hexane to afford a clear oil; $^1$H NMR (300 MHz, CDCl$_3$) δ 8.23 (dd, J=2, 2 Hz, 1H, ArH), 7.99 (ddd, J=2, 2, 8 Hz, 1H, ArH), 7.79 (ddd, J=2, 2, 8 Hz, 1H, ArH), 7.44 (dd, J=8, 8 Hz, 1H, ArH), 7.34 (m, 2H, ArH), 7.19 (m, 2H, ArH), 7.06 (m, 3H, ArH), 5.01 (s, 2H, ArCH$_2$O), 4.36 (q, J=7 Hz, 2H, CO$_2$CH$_2$), 1.64 (s, 4H, CH$_2$CH$_2$), 1.38 (t, J=7 Hz, 3H, CO$_2$CH$_2$CH$_3$), 1.23 (s, 6H, 2×CH$_3$), 1.17 (s, 6H, 2×CH$_3$); $^{13}$C NMR (75 MHz, CDCl$_3$) δ 166.71 (C=O), 155.73, 144.88, 144.24, 138.86, 134.21, 133.88, 130.90, 130.67, 130.37, 130.31, 129.05, 128.02, 127.88, 126.56, 124.93, 124.14, 121.22, 113.13, 70.45, 60.90, 35.02, 34.20, 34.09, 31.83, 31.75, 14.35; IR (film) 2960, 2926, 1718, 1456, 1306, 1282, 1246, 1108, 752 cm$^{-1}$; MS (FAB) m/e 481 (MK+), 465 (MNa+).

For 2-[5,6,7,8-tetrahydro-5,5,8,8-tetramethyl-2-naphthalenyl]methoxy-4′-carbomethoxy-1,1′-biphenyl (51b): scale=0.84 mmol, yield=70%; chromatographed on silica gel using EtOAc/hexane to afford a white solid; $^1$H NMR (300 MHz, CDCl$_3$) δ 8.07 (m, 2H, ArH), 7.64 (m, 2H, ArH), 7.33 (m, 2H, ArH), 7.23 (m, 2H, ArH), 7.05 (m, 3H, ArH), 5.02 (s, 2H, ArCH$_2$O), 3.92 (s, 3H, CO$_2$CH$_3$), 1.65 (s, 4H, CH$_2$CH$_2$), 1.25 (s, 6H, 2×CH$_3$), 1.19 (s, 6H, 2×CH$_3$); $^{13}$C NMR (75 MHz, CDCl$_3$) δ 167.17 (C=O), 155.75, 145.01, 144.37, 143.48, 133.77, 130.81, 130.21, 129.66, 129.37, 129.26, 128.37, 126.62, 125.00, 124.08, 121.24, 113.17, 70.45, 52.06, 35.00, 34.23, 34.11, 31.84, 31.75; IR (film) 2958, 2926, 1724, 1610, 1486, 1450, 1278, 1230, 1112, 1102, 752 cm$^{-1}$; MS (DCI) m/e 429 (MH+), 201 (C$_{15}$H$_{21}$+).

Esters 51a and 51b are hydrolyzed via the method of Example 7 to afford acids 52a and 52b, respectively.

For 2-[5,6,7,8-tetrahydro-5,5,8,8-tetramethyl-2-naphthalenyl]methoxy-[1,1′-biphenyl]-3′-carboxylic acid (52a): scale=0.66 mmol, yield=99%; mp=67.5°–69.5° C.; UV$_{max}$ (MeOH) 212 nm (ε=47464), 286 nm (ε=4428); $^1$H NMR (300 MHz, CD$_3$OD) δ 8.20 (dd, J=2, 8 Hz, 1H, ArH), 7.96 (ddd, J=2, 2, 8 Hz, 1H, ArH), 7.74 (ddd, J=2, 2, 8 Hz, 1H, ArH), 7.47 (dd, J=8, 8 Hz, 1H, ArH), 7.32 (m, 2H, ArH), 7.22 (d, J=8 Hz, 1H, ArH), 7.21 (bs, 1H, ArH), 7.15 (d, J=8 Hz, 1H, ArH), 7.04 (m, 2H, ArH), 5.03 (s, 2H, ArCH$_2$O), 1.65 (s, 4H, CH$_2$CH$_2$), 1.22 (s, 6H, 2×CH$_3$), 1.15 (s, 6H, 2×CH$_3$); $^{13}$C NMR (75 MHz, CD$_3$OD) δ 169.99 (C=O), 156.97, 145.86, 145.18, 140.56, 135.42, 135.27, 132.02, 131.68, 130.25, 130.05, 129.54, 129.13, 128.04, 127.52, 126.15, 125.46, 122.34, 114.63, 71.48, 36.21, 35.13, 35.00, 32.25; IR (KBr) 2960, 2924, 1690, 1286, 1256, 1230, 750 cm$^{-1}$. Anal. Calcd for C$_{30}$H$_{30}$O$_3$.0.22 H$_2$O: C, 80.36; H, 7.33. Found: C, 80.36; H, 7.30.

For 2-[5,6,7,8-tetrahydro-5,5,8,8-tetramethyl-2-naphthalenyl]methoxy-[1,1′-biphenyl]-4′-carboxylic acid (52b): scale=0.69 mmol, yield=87%; chromatographed on silica gel using methanol/CH$_2$Cl$_2$ to yield a white solid; mp=170°–171° C.; UV$_{max}$ (MeOH) 206 nm (ε=35151), 264 nm (ε=13272); $^1$H NMR (300 MHz, CD$_3$OD) δ 8.03 (m, 2H, ArH), 7.62 (m, 2H, ArH), 7.34 (m, 2H, ArH), 7.23 (d, J=8 Hz, 1H, ArH), 7.22 (bs, 1H, ArH), 7.16 (dd, J=2, 8 Hz, 1H, ArH), 7.03 (m, 2H, ArH), 5.02 (s, 2H, ArCH$_2$O), 1.65 (s, 4H, CH$_2$CH$_2$), 1.23 (s, 6H, 2×CH$_3$), 1.15 (s, 6H, 2×CH$_3$); $^{13}$C NMR (75 MHz, CD$_3$OD) δ 169.90 (C=O), 157.06, 145.91, 145.26, 145.13, 135.38, 131.64, 130.75, 130.55, 130.45, 130.14, 127.51, 126.23, 125.37, 122.36, 114.69, 71.55, 36.21, 35.16, 35.02, 32.25; IR (KBr) 3422, 2960, 2924, 2666, 2544, 1688, 1610, 1450, 1418, 1288, 1264, 1230, 752 cm$^{-1}$; MS (DCI) m/e 415 (MH+), 201 (C$_{15}$H$_{21}$+).

Anal. Calcd for C$_{28}$H$_{30}$O$_3$: C, 81.13; H, 7.29. Found: C, 80.91; H, 7.38.

Example 28: Synthesis of Acid 52c

2-[5,6,7,8-Tetrahydro-5,5,8,8-tetramethyl-2-naphthalenyl]methoxy-bromobenzene (50) (1.304 g., 3.49 mmol) is converted by the method of Example 2 (Procedure A) to 2-[5,6,7,8-tetrahydro-5,5,8,8-tetramethyl-2-naphthalenyl]methoxyphenyltributylstannane (53) (1.907 g., 3.27 mmol, 94%): chromatographed on silica gel using hexane to afford a clear oil; $^1$H NMR (300 MHz, CDCl$_3$) 7.36 (dd, J=2, 8 Hz, 1H, ArH), 7.27 (m, 3H, ArH), 7.13 (dd, J=2, 8 Hz, 1H, ArH), 6.92 (m, 1H, ArH), 6.86 (d, J=8 Hz, 1H, ArH), 4.93 (s, 2H, ArCH$_2$O), 1.62 (s, 4H, CH$_2$CH$_2$), 1.61–0.85 (m, 39H, 4xCH$_3$ and 3xC$_4$H$_9$); IR (film) 2956, 2924, 1460, 1434, 1218 cm$^{-1}$; MS (DCI) m/e 585 (MH+), 527 (M-C$_4$H$_9$).

Methyl salicylate (2.50 g., 16.4 mmol) is converted via the method of Example 1 to 2-(trifluoromethylsulphonyloxy)-benzoic acid, methyl ester (54) (4.44 g., 15.6 mmol, 95%) as a clear oil: $^1$H NMR (300 MHz, CDCl$_3$) δ 8.09 (dd, J=2, 8 Hz, 1H, ArH), 7.60 (ddd, J=2, 8, 8 Hz, 1H, ArH), 7.43 (ddd, J=2, 8, 8 Hz, 1H, ArH), 7.25 (d, J=8 Hz, 1H, ArH), 3.96 (s, 3H, CO$_2$CH$_3$).

2-(Trifluoromethylsulphonyloxy)-benzoic acid, methyl ester (54) (0.486 g., 1.71 mmol, 1 equiv.) is dissolved in 3 mL of N-methylpyrrolidone and the solution is degassed. Tris(dibenzylideneacetone)dipalladium (0.156 g., 0.17 mmol, 0.10 equiv.) and triphenylarsine (0.080 g., 0.26 mmol, 0.15 equiv.) are added, followed by a solution of 2-[5,6,7,8-tetrahydro-5,5,8,8-tetramethyl-2-naphthalenyl]methoxyphenyl-tributylstannane (53) (1.00 g., 1.71 mmol, 1 equiv.) in 4 mL of N-methylpyrrolidone. The solution is heated to 67° C. for 5.5 hours with little conversion to product. More tris(dibenzylideneacetone)dipalladium (0.020 mg, 0.022 mmol, 0.01 equiv.) is added and heating continued 22 hours. More tris(dibenzylideneacetone)dipalladium 0.100 g., 0.11 mmol, 0.06 equiv.) and triphenylarsine (0.070 g., 0.23 mmol, 0.13 equiv.) are added along with lithium chloride (0.217 g., 5.10 mmol, 3 equiv.), and heating is continued. After 29 hours, more tris (dibenzylideneacetone) dipalladium (0. 060 g., 0.07 mmol, 0.04 equiv.) and triphenylarsine (0.030 g., 0.10 mmol, 0.06 equiv.) are added, and heating continued for 46 hours. The mixture is allowed to cool to room temperature, and 2 mL of ether is added, followed by 3 mL of saturated aqueous KF solution. After stirring for 30 minutes, the mixture is diluted with water and EtOAc and then filtered. The brown solids are washed with EtOAc, and the filtrate placed in a separatory funnel. The phases are separated, and the aqueous phase is extracted twice with EtOAc. The combined organic phase is washed with 3% aqueous ammonia, and then brine. The extracts are dried (MgSO$_4$) and concentrated. The crude material is chromatographed on silica gel using EtOAc/hexane to afford 2-[5,6,7,8-tetrahydro-5,5,8,8-tetramethyl-2-naphthalenyl]methoxy-[1,1′-biphenyl]-2′-carboxylic acid, methyl ester (55) (0.290 g., 0.68 mmol, 40%) as an oil: $^1$H NMR (300 MHz, CDCl$_3$) δ 7.93 (dd, J=2, 8 Hz, 1H, ArH), 7.51 (ddd, J=2, 8, 8 Hz, 1H, ArH), 7.39–7.31 (m, 3H, ArH), 7.24–7.20 (m, 2H, ArH), 7.11 (d, J=2 Hz, 1H, ArH), 7.04 (m, 2H, ArH), 6.98 (dd, J=2, 8 Hz, 1H, ArH), 4.93 (s, 2H, ArCH$_2$O), 3.55 (s, 3H, CO$_2$CH$_3$), 1.63 (s, 4H, CH$_2$CH$_2$), 1.23 (s, 6H, 2×CH$_3$), 1.17 (s, 6H, 2×CH$_3$); $^{13}$C NMR (75 MHz, CDCl$_3$) δ 168.15 (C=O), 155.52, 144.81, 144.02, 139.54, 134.01, 131.54, 131.47, 131.20, 129.94, 129.71, 128.70, 127.02, 126.34, 124.79, 123.89, 120.92, 112.28, 70.25, 51.62, 35.14, 35.05, 34.24, 34.07, 31.84, 31.67; IR (film) 2958, 2926, 1732, 1598, 1500, 1482, 1456, 1446, 1290, 1252, 1222, 1120, 1086, 740 cm$^{-1}$; MS (DCI) m/e 429 (MH+), 397 (M-CH$_3$O), 201 (C$_{15}$H$_{21}$+).

2-[5,6,7,8-Tetrahydro-5,5,8,8-tetramethyl-2-naphthalenyl]methoxy-[1,1'-biphenyl]-2'-carboxylic acid, methyl ester (55) (0.290 g., 0.68 mmol) is hydrolyzed via the method of Example 7 to afford 2-[5,6,7,8-tetrahydro-5,5,8,8-tetramethyl-2-naphthalenyl]methoxy-[1,1'-biphenyl]-2'-carboxylic acid (52c) (0.282 g., 0.68 mmol, 100%) as a pale yellow foam: mp=75°-76° C.; UV$_{max}$ (MeOH) 208 nm ($\epsilon$=40837), 290 nm ($\epsilon$=3766); $^1$H NMR (300 MHz, CD$_3$OD) $\delta$ 7.92 (dd, J=2, 8 Hz, 1H, ArH), 7.55 (ddd, J=2, 8, 8 Hz, 1H, ArH), 7.40 (ddd, J=2, 8, 8 Hz, 1H, ArH), 7.28 (m, 2H, ArH), 7.17 (m, 3H, ArH), 6.99 (m, 2H, ArH), 6.94 (dd, J=2, 8 Hz 1H, ArH), 4.92 (s, 2H, ArCH$_2$O), 1.64 (s, 4H, CH$_2$CH$_2$), 1.21 (s, 6H, 2×CH$_3$), 1.16 (s, 6H, 2×CH$_3$); $^{13}$C NMR (75 MHz, CD$_3$OD) $\delta$ 171.36 (C=O), 157.03, 145.78, 144.95, 141.04, 135.59, 133.20, 133.06, 132.63, 132.56, 130.96, 130.74, 129.67, 128.05, 127.34, 126.09, 125.23, 121.86, 113.59, 71.21, 36.32, 36.23, 35.20, 34.98, 32.26, 32.22; IR (KBr) 3432, 2960, 2924, 1694, 1484, 1294, 1280, 1262, 1222, 750 cm$^{-1}$; MS (DCI) m/e 415 (MH+), 397 (M-OH), 201 (C$_{15}$H$_{21}$+). Anal. Calcd for C$_{28}$H$_{30}$O$_3$.0.25 H$_2$O: C, 80.25; H, 7.34. Found: C, 80.18; H, 7.17.

Example 29: Synthesis of Acid 57

2-[5,6,7,8-Tetrahydro-5,5,8,8-tetramethyl-2-naphthalenyl]methoxy-bromobenzene (50) (0.366 g., 0.98 mmol; see Example 27) is coupled to stannane 3 g (0.663 g., 1.46 mmol; see Example 2) via the method of Example 3 to yield 2-[5,6,7,8-tetrahydro-5,5,8,8-tetramethyl-2-naphthalenyl]methoxy-[1,1'-biphenyl]-3'-acetic acid, ethyl ester (56) (0.278 g., 0.63 mmol, 64%): chromatographed on silica gel using EtOAc/hexane to afford a colorless oil; $^1$H NMR (300 MHz, CDCl$_3$) $\delta$ 7.59–7.36 (m, 3H, ArH), 7.35–7.22 (m, 5H, ArH), 7.05 (m, 3H, ArH), 5.01 (s, 2H, ArCH$_2$O), 4.12 (q, J=7 Hz, 2H, CO$_2$CH$_2$), 3.62 (s, 2H, ArCH$_2$CO$_2$), 1.65 (s, 4H, CH$_2$CH$_2$), 1.25 (s, 6H, 2×CH$_3$), 1.23 (t, J=7 Hz, 3H, CO$_2$CH$_2$CH$_3$), 1.20 (s, 6H, 2×CH$_3$); $^{13}$C NMR (75 MHz, CDCl$_3$) $\delta$ 171.63 (C=O), 155.78, 144.86, 144.21, 138.85, 134.06, 133.74, 131.05, 130.99, 130.48, 128.63, 128.58, 128.04, 127.66, 126.58, 125.03, 124.24, 121.16, 113.25, 70.51, 60.80, 41.51, 35.04, 34.22, 34.09, 31.85, 31.80, 14.20; IR (film) 2960, 2926, 1736, 1500, 1458, 1364, 1266, 1248, 1154, 1032, 752 cm$^{-1}$; MS (DCI) m/e 457 (MH+), 411 (M-C$_2$H$_5$O), 201 (C$_{15}$H$_{21}$+).

2-[5,6,7,8-Tetrahydro-5,5,8,8-tetramethyl-2-naphthalenyl]methoxy-[1,1'-biphenyl]-3'-acetic acid, ethyl ester (56) (0.260 g., 0.59 mmol) is hydrolyzed via the method of Example 7 to afford 2-[5,6,7,8-tetrahydro-5,5,8,8-tetramethyl-2-naphthalenyl]methoxy-[1,1'-biphenyl]-3'-acetic acid (57) (0.218 g., 0.51 mmol, 86%): chromatographed on silica gel using methanol/CH$_2$C$_{12}$ to afford a white solid; UV$_{max}$ (MeOH) 210 nm ($\epsilon$=42212), 248 nm ($\epsilon$=10087), 284 nm ($\epsilon$=4241); $^1$H NMR (300 MHz, CD$_3$OD) $\delta$ 7.42 (m, 2H, ArH), 7.34–7.21 (m, 6H, ArH), 7.10 (d, J=8 Hz, 1H, ArH), 7.02 (m, 2H, ArH), 4.98 (s, 2H, ArCH$_2$O), 3.60 (s, 2H, ArCH$_2$CO$_2$), 1.66 (s, 4H, CH$_2$CH$_2$), 1.23 (s, 6H, 2×CH$_3$), 1.18 (s, 6H, 2×CH$_3$); $^{13}$C NMR (75 MHz, CD$_3$OD) $\delta$ 175.64 (C=O), 157.03, 145.83, 145.20, 140.39, 135.61, 135.59, 132.52, 131.78, 131.66, 129.77, 129.35, 129.01, 128.79, 127.56, 126.30, 125.57, 122.27, 114.75, 71.56, 42.05, 36.23, 35.17, 35.02, 32.30, 32.28; IR (KBr) 2960, 2924, 1710, 1500, 1458, 1266, 1230, 752 cm$^{-1}$; MS (DCI) m/e 429 (MH+), 428 (M+), 201 (C$_{15}$H$_{21}$+). Anal. Calcd for C$_{29}$H$_{32}$O$_3$: C, 81.28; H, 7.53. Found: C, 81.37; H, 7.62.

Reasonable variations, such as those which would occur to a skilled artisan, can be made herein without departing from the scope of the invention.

We claim:

1. Compounds of Formulas I and II:

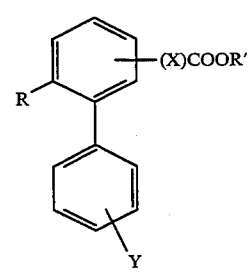

(I)

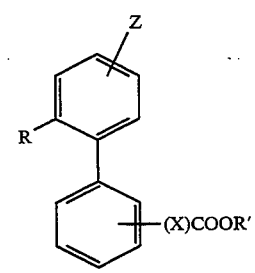

(II)

wherein:

Y=COOH, CH$_2$CO$_2$H, H, F, Cl, Br, I, COOR', CH$_2$CO$_2$R', CONH$_2$, COR'', CHO, CH$_2$OH, CH$_2$OR'', OH, OR'', CF$_3$, C$_{1-6}$ alkyl, C$_{1-6}$ alkenyl, C$_{1-6}$ haloalkyl, NO$_2$, P(O)(OH)$_2$, SO$_2$H, or SO$_3$H;

Z=H, F, Cl, Br, I, CONH$_2$, COR'', CHO, CH$_2$OH, CH$_2$OR'', OH, OR'', CF$_3$, C$_{1-6}$ alkyl, C$_{1-6}$ alkenyl, C$_{1-6}$ haloalkyl, NO$_2$, P(O)(OH)$_2$, SO$_2$H, or SO$_3$H;

X=(CH$_2$)$_n$ n=0, 1, or 2; or a cis or trans CH=CH;

R=substituted or unsubstituted alkyl, aryl, arylalkyl, alkyloxy, arylalkyloxy, alkenyl, or arylalkenyl groups with the proviso that R must have 8 or more carbons;

R'=H, C$_{1-6}$ alkyl, C(R$^1$)$_2$OC(O)R$^2$, CH$_2$CH$_2$NR$^3$R$^4$, CH$_2$CH$_2$CH$_2$NR$^3$R$^4$, or other groups yielding physiologically hydrolyzable esters;

R''=C$_{1-6}$ alkyl;

R$^1$=H, CH$_3$, C$_2$H$_5$, CH$_2$CH$_2$CH$_3$;

R$^2$=C$_{6-12}$ aryl, C$_{1-7}$ linear, branched or cyclic alkyl, or C$_{1-7}$ linear branched or cyclic alkoxy;

R$^3$=R$^4$, or, it may be linked with R$^4$, to form a C$_3$–C$_6$ cycloalkyl or a —CH$_2$CH$_2$OCH$_2$CH$_2$— group; and R$^4$=C$_{1-3}$ alkyl; or salts thereof.

2. The compounds of claim 1 having structures selected from the group consisting of structure types IA, IB, IC, ID, IE, and II:

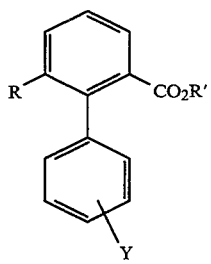
(IA)

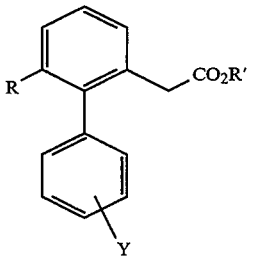
(IB)

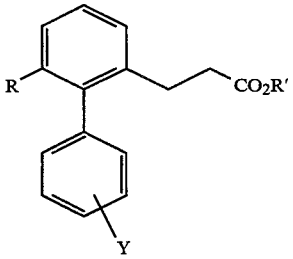
(IC)

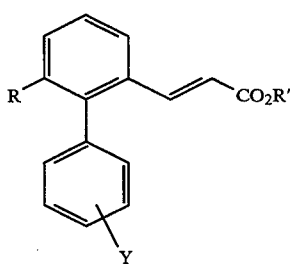
(ID)

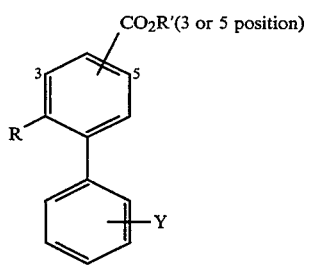
(IE)

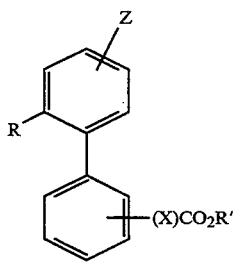
(II)

3. A compound of claim 2 conforming to structure IA.

4. A compound of claim 3 selected from the group consisting of:
(E)-[2-(5,6,7,8-tetrahydro-5,5,8,8-tetramethyl-2-naphthalenyl)-1-propenyl]-[1,1'-biphenyl]-6,3'-dicarboxylic acid;
2-[(3,4-bisdecyloxy)phenyl]methoxy-[1,1'-biphenyl]-6,3'-dicarboxylic acid;
2-[(3,4-bispentyloxy)phenyl]methoxy-[1,1'-biphenyl]-6,3'-dicarboxylic acid;
2-[(3,4-biscyclopentyloxy)phenyl]methoxy-[1,1'-biphenyl]-6,3'-dicarboxylic acid;
2-[4-(1-adamantyl)-3-methoxyphenyl]methoxy-[1,1'-biphenyl]-6,3'-dicarboxylic acid;
2-[(3,4-bispentyloxy)phenyl]methoxy-[1,1'-biphenyl]-6-carboxylic acid;
2-[(3,4-bispentyloxy)phenyl]methoxy-[1,1'-biphenyl]-3'-trifluoromethyl-6-carboxylic acid;
2-[(4-decyloxy)phenyl]methoxy-[1,1'-biphenyl]-6-carboxylic acid;
2-[(5,6,7,8-tetrahydro-5,5,8,8-tetramethyl-2-naphthalenyl)methoxy-[1,1'-biphenyl]-6,3'-dicarboxylic acid, 3'-ethyl ester;
2-(5,6,7,8-tetrahydro-5,5,8,8-tetramethyl-2-naphthalenyl)methoxy-[1,1'-biphenyl]-6,3'-dicarboxylic acid;
2-(5,6,7,8-tetrahydro-5,5,8,8-tetramethyl-2-naphthalenyl)methoxy-[1,1'-biphenyl]-6-carboxylic acid;
2-(5,6,7,8-tetrahydro-5,5,8,8-tetramethyl-2-naphthalenyl)methoxy-4'-(1,1-dimethylethyl)-[1,1'-biphenyl]-6-carboxylic acid;
2-(5,6,7,8-tetrahydro-5,5,8,8-tetramethyl-2-naphthalenyl)methoxy-4'-(2-hydroxy-1-ethyl)-[1,1'-biphenyl]-6-carboxylic acid; and
6-carboxy-2-[5,6,7,8-tetrahydro-5,5,8,8-tetramethyl-2-naphthalenyl]methoxy-[1,1'-biphenyl]-3'-acetic acid.

5. A compound of claim 2 conforming to structure IB.

6. A compound of claim 5 selected from the group consisting of:
3'-carboxy-(E)-2-[(5,6,7,8-tetrahydro-5,5,8,8,-tetramethyl-2-naphthalenyl)-1-propenyl]-[1,1'-biphenyl]-6-acetic acid;
3'-carboxy-2-[(1,2,3,4-tetrahydro-1,1,4,4-tetramethyl)-6-anthracenyl]-[1,1'-biphenyl]-6-acetic acid;
2-[(3,4-bispentyloxy)phenyl]methoxy-3'-carboxy-[1,1'-biphenyl]-6-acetic acid;
2-[(3,4-biscyclopentyloxy)phenyl]methoxy-3'-carboxy-[1,1'-biphenyl]-6-acetic acid;
3'-carboxy-2-[4-decyloxyphenyl]methoxy-[1,1'biphenyl]-6-acetic acid;
3'-carboxy-2-[4-(1-adamantyl)-3-methoxyphenyl]methoxy-[1,1'-biphenyl]-6-acetic acid;
2-(5,6,7,8-tetrahydro-5,5,8,8-tetramethyl-2-naphthalenyl)methoxy-[1,1'-biphenyl]-6-acetic acid; and
3'-carboxy-2-(5,6,7,8-tetrahydro-5,5,8,8-tetramethyl-2-naphthalenyl)methoxy-[1,1'-biphenyl]-6-acetic acid.

7. A compound of claim 2 conforming to structure IC.

8. A compound of claim 7 selected from the group consisting of:
2-[3,4-bis(3-methyl-2-butenyloxy)phenyl]methoxy-3'-carboxy-[1,1'-biphenyl]-6-propanoic acid;

2-[3,4-bis(cyclopentyloxy)phenyl]methoxy-3'-carboxy-[1,1'-biphenyl]-6-propanoic acid;
2-[3,4-bis(pentyloxy)phenyl]methoxy-3'-carboxy-[1,1'-biphenyl]-6-propanoic acid; and
3'-carboxy-2-[5,6,7,8-tetrahydro-5,5,8,8-tetramethyl-2-naphthalenyl]methoxy-[1,1'-biphenyl]-6-propanoic acid.

9. A compound of claim 2 conforming to structure ID.

10. A compound of claim 9 selected from the group consisting of:
2-[3,4-bis(3-methyl-2-butenyloxy)phenyl]methoxy-3'-carboxy-[1,1'-biphenyl]-6-[(E)-3-propenoic acid];
2-[3,4-bis(cyclopentyloxy)phenyl]methoxy-3'-carboxy-[1,1'-biphenyl]-6-[(E)-3-propenoic acid];
2-[3,4-bis(pentyloxy)phenyl]methoxy-3'-carboxy-[1,1'-biphenyl]-6-[(E)-3-propenoic acid]; and
3'-carboxy-2-[5,6,7,8-tetrahydro-5,5,8,8-tetramethyl-2-naphthalenyl]methoxy-[1,1'-biphenyl]-6-[(E)-3-propenoic acid].

11. A compound of claim 2 conforming to structure IE.

12. A compound of claim 11 selected from the group consisting of:
2-[5,6,7,8-tetrahydro-5,5,8,8-tetramethyl-2-naphthalenyl]methoxy-[1,1'-biphenyl]-5-carboxylic acid; and
2-[5,6,7,8-tetrahydro-5,5,8,8-tetramethyl-2-naphthalenyl]methoxy-[1,1'-biphenyl]-3-carboxylic acid.

13. A compound of claim 2 conforming to structure II.

14. A compound of claim 13 selected from the group consisting of:
2-[5,6,7,8-tetrahydro-5,5,8,8-tetramethyl-2-naphthalenyl]methoxy-[1,1'-biphenyl]-3'-carboxylic acid;
2-[5,6,7,8-tetrahydro-5,5,8,8-tetramethyl-2-naphthalenyl]methoxy-[1,1'-biphenyl]-4'-carboxylic acid;
2-[5,6,7,8-tetrahydro-5,5,8,8-tetramethyl-2-naphthalenyl]methoxy-[1,1'-biphenyl]-2'-carboxylic acid; and
2-[5,6,7,8-tetrahydro-5,5,8,8-tetramethyl-2-naphthalenyl]methoxy-[1,1'-biphenyl]-3'-acetic acid.

15. A pharmaceutical composition containing an anti-inflammatory effective amount of at least one compound of claim 1 and a suitable amount of at least one pharmaceutically acceptable carrier.

16. The composition of claim 15 wherein the compound of claim 1 is present in an amount of about 0.005 to about 10.0 wt %.

17. The composition of claim 16 in a topical dosage form.

18. The composition of claim 16 in an oral dosage form.

19. A method of treating inflammation comprising the step of administering to a subject an anti-inflammatory effective amount of a compound of claim 1.

20. A method of treating inflammation comprising the step of administering to a subject an anti-inflammatory effective amount of a compound of claim 2.

21. The method of claim 19 wherein the compound is administered via a topical formulation.

22. The method of claim 19 wherein the compound is administered via an oral formulation.

23. The composition of claim 15 in a topical dosage form.

24. The composition of claim 15 in an oral dosage form.

25. The method of claim 20 wherein the compound is administered via a topical formulation.

26. The method of claim 20 wherein the compound is administered via an oral formulation.

* * * * *